United States Patent
Qiu et al.

(10) Patent No.: US 9,708,407 B2
(45) Date of Patent: Jul. 18, 2017

(54) ANTI-CD52 ANTIBODIES

(71) Applicant: Genzyme Corporation, Cambridge, MA (US)

(72) Inventors: Huawei Qiu, Cambridge, MA (US); Ronnie Rong Wei, Cambridge, MA (US); Clark Qun Pan, Cambridge, MA (US); Rebecca Sendak, Cambridge, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 14/774,911

(22) PCT Filed: Mar. 13, 2014

(86) PCT No.: PCT/US2014/026159
§ 371 (c)(1),
(2) Date: Sep. 11, 2015

(87) PCT Pub. No.: WO2014/151644
PCT Pub. Date: Sep. 25, 2014

(65) Prior Publication Data
US 2016/0024219 A1    Jan. 28, 2016

Related U.S. Application Data

(60) Provisional application No. 61/794,576, filed on Mar. 15, 2013.

(51) Int. Cl.
*C07K 16/00* (2006.01)
*C07K 16/28* (2006.01)

(52) U.S. Cl.
CPC ...... *C07K 16/2893* (2013.01); *C07K 2317/21* (2013.01); *C07K 2317/24* (2013.01); *C07K 2317/31* (2013.01); *C07K 2317/515* (2013.01); *C07K 2317/56* (2013.01); *C07K 2317/565* (2013.01); *C07K 2317/622* (2013.01); *C07K 2317/73* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,494,999 A | 2/1996 | Hale et al. | |
| 5,545,404 A | 8/1996 | Page | |
| 6,054,561 A | 4/2000 | Ring | |
| 6,172,213 B1 | 1/2001 | Lowman et al. | |
| 7,119,248 B1 | 10/2006 | Rajewsky et al. | |
| 7,465,790 B2 | 12/2008 | Waldmann et al. | |
| 8,084,584 B2 | 12/2011 | Sugo et al. | |
| 8,617,554 B2 * | 12/2013 | Roberts | C07K 16/2893 424/130.1 |
| 2002/0132983 A1 | 9/2002 | Junghans | |
| 2004/0110226 A1 | 6/2004 | Lazar et al. | |
| 2004/0219156 A1 | 11/2004 | Goldenberg et al. | |
| 2005/0118172 A1 | 6/2005 | Hale et al. | |
| 2005/0191632 A1 | 9/2005 | Byrd et al. | |
| 2006/0204496 A1 | 9/2006 | Kojima et al. | |
| 2006/0228351 A1 | 10/2006 | Masuyama et al. | |
| 2007/0178098 A1 | 8/2007 | Way et al. | |
| 2007/0253948 A1 | 11/2007 | Chan et al. | |
| 2008/0248529 A1 | 10/2008 | Carr et al. | |
| 2012/0058082 A1 | 3/2012 | Kaplan et al. | |
| 2012/0070408 A1 | 3/2012 | Kaplan et al. | |
| 2014/0341910 A1 | 11/2014 | Roberts et al. | |

FOREIGN PATENT DOCUMENTS

| | | |
|---|---|---|
| CN | 1508155 | 6/2004 |
| EP | 0120694 | 10/1984 |
| EP | 0125023 | 11/1984 |
| EP | 0239400 | 9/1987 |
| EP | 0519596 | 12/1992 |
| EP | 0194276 | 8/1993 |
| EP | 0616537 | 3/1999 |
| EP | 1618891 | 1/2006 |
| WO | WO-8601533 | 3/1986 |
| WO | WO-8807089 | 9/1988 |
| WO | WO-8907142 | 8/1989 |
| WO | WO-9203918 | 3/1992 |
| WO | WO 9207084 | 4/1992 |
| WO | WO-9310423 | 5/1993 |
| WO | WO-9404679 | 3/1994 |

(Continued)

OTHER PUBLICATIONS

Agarwal et al., "The role of alemtuzumab in facilitating maintenance immunosuppression minimization following solid organ transplantation," Transplant Immunol., 20:6-11 (2008).

Alexander et al., "Development of high potency universal DR-restricted helper epitopes by modification of high affinity DR-blocking peptides," Immunity, 1:751-761 (1994).

Bach et al., "Regulatory T cells under scrutiny," Nature Reviews Immunology, 3(3):189-98 (2003).

Barrat et al., "In vitro generation of interleukin 10-producing regulatory CD4(+) T cells is induced by immunosuppressive drugs and inhibited by T helper type 1 (Th1)- and Th2-inducing cytokines," Journal of Experimental Medicine, 195(5):603-616 (2002).

Battaglia et al., "Rapamycin promotes expansion of functional CD4+CD25+FOXP3+ regulatory T cells of both healthy subjects and type 1 diabetic patients," Journal of Immunology, 177(12):8338-8347 (2006).

Battaglia et al., "Rapamycin selectively expands CD4+CD25+FoxP3+ regulatory T cells," Blood, 105:4743-4748 (2005).

(Continued)

*Primary Examiner* — Laura B Goddard
*Assistant Examiner* — Meera Natarajan
(74) *Attorney, Agent, or Firm* — Steptoe & Johnson LLP; Z. Ying Li; Wyan-Ching M. Lee

(57) ABSTRACT

Anti-human CD52 antibodies and antigen-binding fragments thereof are provided. Also provided are isolated nucleic acids, recombinant vectors and host cells for making the antibodies and fragments. The antibodies and fragments can be used in therapeutic applications to treat, for example, autoimmune diseases, cancer, and graft rejection.

45 Claims, 48 Drawing Sheets

(56) References Cited

FOREIGN PATENT DOCUMENTS

| | | |
|---|---|---|
| WO | WO-9426087 | 11/1994 |
| WO | WO-9429351 | 12/1994 |
| WO | WO-9806248 | 2/1998 |
| WO | WO-9852976 | 11/1998 |
| WO | WO-0034317 | 6/2000 |
| WO | WO-0138318 | 5/2001 |
| WO | WO 2004087210 | 10/2004 |
| WO | WO 2005042581 | 5/2005 |
| WO | 2006/126068 | 11/2006 |
| WO | WO-2007121233 | 10/2007 |
| WO | WO-2008031626 | 3/2008 |
| WO | 2009/000406 | 12/2008 |
| WO | WO/2010/132659 | * 11/2010 |
| WO | WO-2010132659 | 11/2010 |

OTHER PUBLICATIONS

Bloom et al., "CD4+ CD25+ FoxP3+ regulatory T cells increase de novo in kidney transplant patients after immunodepletion with Campath-1H," Am. J. Transplant, 8(4):793-802 (2008).

Coles et al. "Alemtuzumab vs. interferon Beta-la in early multiple sclerosis," The CAMMS223 Trial Investigators, New England Journal of Medicine, 359:1786-1801 (2008).

Dick et al., "Campath-1H therapy in refractory ocular inflammatory disease," British Journal of Ophthalmology, 84(1):107-109 (2000).

Elsner et al., "Surface and mRNA expression of the CD52 antigen by human eosinophils but not by neutrophils," Blood, 88:4684-4693 (1996).

Ewert et al., "Biophysical properties of camelid VHH domains compared to those of human VH3 Domains," Biochemistry, 41:3628-3636 (2002).

Gilleece et al., "Effect of Campath-1H antibody on human hematopoietic progenitors in vitro," Blood, 82:807-812 (1993).

Gilliland et al., "Elimination of the immunogenicity of therapeutic antibodies," Journal of Immunology, 162:3663-3671 (1999).

Ginaldi et al., "Levels of expression of CD52 in normal and leukemic B and T cells: correlation with in vivo therapeutic responses to Campath-1H," Leukemia Research, 22(2):185-191 (1998).

Gregori et al., "Regulatory T cells induced by 1 alpha,25-dihydroxyvitamin D3 and mycophenolate mofetil treatment mediate transplantation tolerance ," Journal of Immunology, 167:1945-1953 (2001).

Gribben et al., "Rediscovering alemtuzumab: current and emerging therapeutic roles," British Journal of Haematology, 144:818-831 (2009).

Hale et al., "CD52 (CAMPATH1)," Journal of Biological Regulators and Homeostatic Agents, 15:386-391 (2001).

Hale, "Synthetic peptide mimotype of the CAMPATH-1 (CD52) antigen, a small glycosylphosphatidylinositol-anchored glycoprotein," Immunotechnology, 1:175-187 (1995).

Hasegawa et al., "Epitope analysis for human sperm-immobilizing monoclonal antibodies, MAb H6-3C4, 1G12 and campath-1," Molecular Human Reproduction, 9:337-343 (2003).

Hederer et al., "The CD45 tyrosine phosphatase regulates Campath-1H (CD52)-induced TCR-dependent signal transduction in human T cells," International Immunology, 12(4):505-516 (2000).

Hirst et al., "Campath 1-H treatment in patients with aggressive relapsing remitting multiple sclerosis," Journal of Neurology, 255(2):231-238 (2008).

Hu et al., "Investigation of the mechanism of action of alemtuzumab in a human CD52 transgenic mouse model," Immunology, 128:260-270 (2009).

Isaacs et al., "Humanized monoclonal antibody therapy for rheumatoid arthritis" Lancet, 340:748-752 (1992).

Jia et al., "A novel method of Multiplexed Competitive Antibody Binning for the characterization of monoclonal antibodies," Journal of Immunological Methods, 288:91-98 (2004).

Jilani et al., "Alemtuzumab: validation of a sensitive and simple enzyme-linked immunosorbent assay," Leukemia Research, 28(12):1255-1262 (2004).

Kenanova et al., "Tailoring the Pharmacokinetics and Positron Emission Tomography Imaging Properties of Anti—Carcinoembryonic Antigen Single-Chain Fv-Fc Antibody Fragments," Cancer Research, 65:622-631 (2005).

Lim et al., "Effect of anti-CD52 antibody alemtuzumab on ex-vivo culture of umbilical cord blood stem cells," Journal of Hematology & Oncology 1:19 (2008).

Loh et al., "Development of a secondary autoimmune disorder after hematopoietic stem cell transplantation for autoimmune diseases: role of conditioning regimen used," Blood, 109(6):2643-2648 (2007).

Lundin et al., "Phase 2 study of alemtuzumab (anti-CD52 monoclonal antibody) in patients with advanced mycosis fungoides/Sezary syndrome," Blood, 101:4267-4272 (2003).

Majidi et al., "Target therapy of cancer: implementation of monoclonal antibodies and nanobodies," Human Antibodies, 18(3):81-100 (2009).

Moreton et al., "Alemtuzumab therapy in B-cell lymphoproliferative disorders," Semin. Oncol., 30(4):493-501 (2003).

Muyldermans et al., "Unique single-domain antigen binding fragments derived from naturally occurring camel heavy chain antibodies," Journal of Molecular Recognition, 12(2):131-140 (1999).

Nguyen et al., "Campath-1H activates multiple pathways and transcription factors (CREB, ATF-1, Egr1&2 and Stat3) upon binding to CD52 on B-cells," Abstract #4431 (Apr. 21, 2009) (2 pages).

Noris et al., "Regulatory T cells and T cell depletion: role of immunosuppressive drugs," J. Am. Soc. Nephrol., 18:1007-1018 (2007).

Pascual et al., "Alemtuzumab induction and recurrence of glomerular disease after kidney transplantation," Transplantation, 83(11):1429-1434 (2007).

Pereira et al., "Cardiolipin binding a light chain from lupus-prone mice," Biochemistry, 37:1430-1437 (1998).

Pulaski et al., "Identifying alemtuzumab as an anti-myeloid cell antiangiogenic therapy for the treatment of ovarian cancer," Journal of Translational Medicine, 7:49 (2009) (14 pages).

Ravandi et al., "Alemtuzumab," Expert Reviews, 5(1):39-51 (2005).

Rawstron et al., The PHN phenotype cells that emerge in most patients after CAMPATH-1H therapy are present prior to treatment, British Journal of Haematology, 107:148-153 (1999).

Reiff, "A review of Campath in autoimmune disease: biologic therapy in the gray zone between immunosuppression and immunoablation," Hematology, 10:79-93 (2005).

Rodig et al., "Heterogeneous CD52 expression among hematologic neoplasms: implications for the use of alemtuzumab (CAMPATH-1H)," Clinical Cancer Research, 12:7174-7179 (2006).

Rowan et al., "Cross-linking of the CAMPATH-1 antigen (CD52) triggers activation of normal human T lymphocytes," Int. Immunol , 7.69-77 (1995).

Sato et al., "Reshaping a human antibody to inhibit the interleukin 6-dependent tumor cell growth," Cancer Research, 53:851-856 (1993).

Siders et al., "Involvement of neutrophils and natural killer cells in the anti-tumor activity of alemtuzumab in xenograft tumor models," Leukemia & Lymphoma, 51(7):1293-1304 (2010).

Sportes et al., "Perspective on potential clinical applications of recombinant human interleukin-7," Cytokine Therapies: Annals of the New York Academy of Science, 1182:28-38 (2009).

Stebbings et al., "Mechanisms of protection induced by attenuated simian immunodeficiency virus: II. Lymphocyte depletion does not abrogate protection," AIDS Research Human Retroviruses 14:1187-1198 (1998).

Treumann et al., "Primary structure of CD52," Journal of Biological Chemistry, 270(11):6088-6099 (1995).

Vivas et al., "Alemtuzumab for refractory celiac disease in a patient at risk for enteropathy-associated T-cell lymphoma," New England Journal of Medicine, 354:2514-2515 (2006).

Walsh et al., "Long-term follow-up of relapsing/refractory anti-neutrophil cytoplasm antibody associated vasculitis treated with the

(56) References Cited

OTHER PUBLICATIONS lymphocyte depleting antibody alemtuzumab (CAMPATH-1H)," Annals of Rheumatic Disease, 67:1322-1327 (2008).

Ward et al., "Binding activities of a repertoire of single immunoglobulin variable domains secreted from *Escherichia coli*," Nature 341:544-546 (1989).

Watanabe et al., "CD52 is a novel costimulatory molecule for induction of CD4+ regulatory T cells," Clinical Immunology, 120(3):247-259 (2006).

Xia et al., "Efficient complement-mediated lysis of cells containing the CAMPATH-1 (CDw52) antigen," Molecular Immunology, 30(12):1089-1096 (1993).

Yoshio et al., "Expression of CD52 on peripheral blood T lymphocytes closely correlates with disease activity in patients with systemic lupus erythematosus (SLE)," Arthritis and Rheumatism, 54(9):S459-S459 (2006).

Chelius et al., "Identification and characterization of deamidation sites in the conserved regions of human immunoglobulin gamma antibodies," Anal Chem. 77(18):6004-11 (2005).

Vlasak et al., "Identification and characterization of asparagine deamidation in the light chain CDR1 of a humanized IgG1 antibody," Anal Biochem. 392(2):145-54 (2009).

Muyldermans et al., "Single domain camel antibodies: current status," J. Biotechnology 74:277-302 (2001).

Chen et al., "Enhancement and destruction of antibody function by somatic mutation: unequal occurrence is controlled by V gene combinatorial associations," EMBO J 14:2784-2794 (1995).

Colman et al., "Effects of amino acid sequence changes on antibody-antigen interactions," Res Immunol 145:33-36 (1994).

Kussie et al., "A single engineered amino acid substitution changes antibody fine specificity," J Immunol 152:146-152 (1994).

Lederman et al., "A single amino acid substitution in a common African allele of the CD4 molecule ablates binding of the monoclonal antibody, OKT4," Molecular Immunology 28:1171-1181 (1991).

Li et al., "beta-Endorphin omission analogs: dissociation of immunoreactivity from other biological activities," Proc Natl Acad Sci USA 77:3211-3214 (1980).

Rudikoff et al., "Single amino acid substitution altering antigen-binding specificity," Proc Natl Acad Sci USA 79:1979-1983 (1982).

\* cited by examiner

FIG. 5
| Tier | Sample | Octet Conc (µg/ml) |
|---|---|---|
| 2 | Ab2 | 0.32 |
| 2 | KGN | 0.405 |
| 2 | Ab22 | 0.327 |
| 2 | Ab6 | 0.41 |
| 2 | Ab7 | 0.328 |
| 2 | Ab23 | 0.328 |
| 2 | Ab5 | 0.347 |
|   | CTL | 0.907 |
| Tier | Sample | Octet Conc (µg/ml) |
|---|---|---|
| 3 | Ab13 | 0.254 |
| 3 | Ab15 | 0.233 |
| 3 | Ab11 | 0.655 |
| 3 | Ab20 | 0.674 |
| 3 | Ab19 | 2.085 |
| 3 | Ab16 | 0.42 |
| 3 | Ab18 | 0.149 |
| 3 | Ab21 | 0.35 |
| 3 | Ab17 | 0.207 |
| 3 | Ab14 | 0.657 |
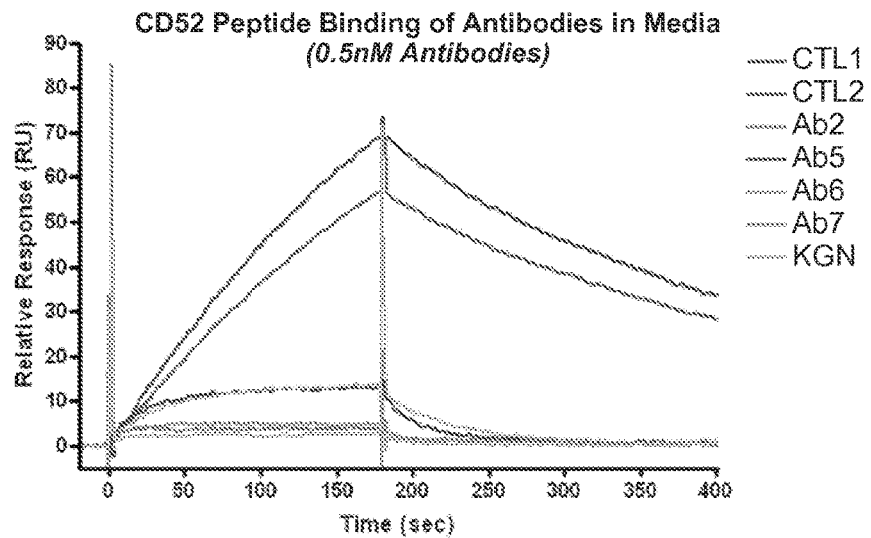
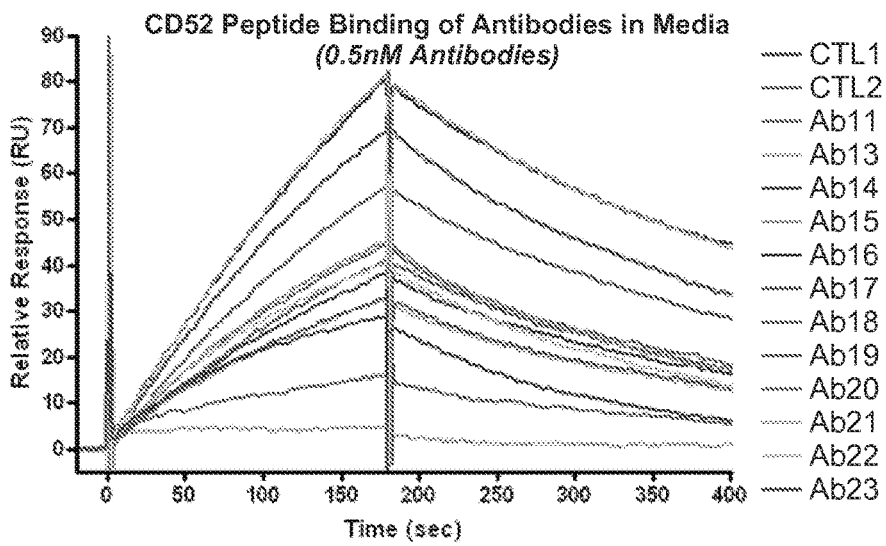

FIG. 9

Human CD52 protein

MKRFLFLLLTISLLVMVQIQTGLSGQNDTSQTSSPSASSSMSGGIFLFFVANAIIHLF
CFS (SEQ ID NO: 1)

FIG. 10

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN full-length heavy chain amino acid sequence

*MEAPAQLLFLLLLWLPDTTG*EVQLVESGGGLVQPGGSLRLSCAASGFPFSNYWM
NWVRQAPGKGLEWVGQIRLKSNNYATHYAESVKGRFTISRDDSKNSLYLQMNS
LKTEDTAVYYCTPIDYWGQGTTVTVSSASTKGPSVFPLAPSSKSTSGGTAALGCL
VKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQ
GNVFSCSVMHEALHNHYTQKSLSLSPGK (SEQ ID NO: 3)

Ab26 full-length light chain amino acid sequence

*MEAPAQLLFLLLLWLPDTTG*DIVMTQTPLSLSVTPGQPASISCKSSQSLLYSNGKT
YLNWVLQKPGQSPQRLIYLVSKLDSGVPDRFSGSGSGTDFTLKISRVEAEDVGVY
YCVQGSHFHTFGQGTKLEIKRTVAAPSVFIFPPSDEQLKSGTASVVCLLNNFYPRE
AKVQWKVDNALQSGNSQESVTEQDSKDSTYSLSSTLTLSKADYEKHKVYACEV
THQGLSSPVTKSFNRGEC (SEQ ID NO: 4)

FIG. 11

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN full-length heavy chain nucleic acid sequence CCCACCATGGAAGCCCCAGCGCAGCTTCTCTTCCTCCTGCTACTCTGGCTCCC
TGATACCACCGGAGAGGTACAGCTGGTGGAGTCGGGAGGAGGCTTGGTA
CAGCCTGGGGGTTCTCTGAGACTCTCCTGTGCAGCTTCTGGATTCCCATT
CAGTAACTACTGGATGAACTGGGTCCGCCAGGCTCCAGGGAAGGGACTT
GAGTGGGTGGGTCAAATTAGATTGAAATCTAATAATTATGCAACACATTA
TGCGGAGTCTGTGAAGGGCGGTTCACCATCTCCAGAGATGATTCCAAA
AACAGCCTCTATCTTCAAATGAATTCCCTGAAAACTGAAGACACTGCCGT
TTATTACTGTACCCCAATTGACTATTGGGGCCAAGGCACCACTGTCACAG
TCTCCTCAGCCTCCACCAAGGGCCCATCGGTCTTCCCCCTGGCACCCTCC
TCCAAGAGCACCTCTGGGGGTACAGCGGCCCTGGGCTGCCTGGTCAAGG
ACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT
CCCTCAGCAGCGTGGTGACCGTGCCCTCAGCAGCTTGGGCACCCAGAC
CTACATCTGCAACGTGAATCACAAGCCCAGCAACACCAAGGTGGACAAG
AAAGTTGAGCCCAAATCTTGTGACAAAACTCACACATGCCCACCGTGCCC
AGCACCTGAACTCCTGGGGGGACCGTCAGTCTTCCTCTTCCCCCCAAAAC
CCAAGGACACCCTCATGATCTCCCGGACCCCTGAGGTCACATGCGTGGT
GGTGGACGTGAGCCACGAAGACCCTGAGGTCAAGTTCAACTGGTACGTG
GACGGCGTGGAGGTGCATAATGCCAAGACAAAGCCGCGGGAGGAGCAG
TACAACAGCACGTACCGTGTGGTCAGCGTCCTCACCGTCCTGCACCAGG
ACTGGCTGAATGGCAAGGAGTACAAGTGCAAGGTCTCCAACAAAGCCCT
CCCAGCCCCCATCGAGAAAACCATCTCCAAAGCCAAAGGGCAGCCCCGA
GAACCACAGGTGTACACCCTGCCCCCATCCCGGGATGAGCTGACCAAGA
ACCAGGTCAGCCTGACATGCCTGGTCAAAGGCTTCTATCCCAGCGACAT
CGCCGTGGAGTGGGAGAGCAATGGGCAGCCGGAGAACAACTACAAGAC
CACGCCTCCCGTGCTGGACTCCGACGGCTCCTTCTTCCTCTACAGCAAGC
TCACCGTGGACAAGTCCAGGTGGCAGCAGGGGAACGTCTTCTCATGCTC
CGTGATGCATGAGGCTCTGCACAACCACTACACGCAGAAGAGCCTCTCC
CTGTCTCCGGGTAAATGATGA (SEQ ID NO: 5)

FIG. 11 (cont'd)

Ab26 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 6)

Ab1 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTGATGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 112)

FIG. 11 (cont'd)

Ab2 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTCACGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 113)

Ab3 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAAAGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 114)

FIG. 11 (cont'd)

Ab4 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTCAAGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 115)

Ab5 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTCGCGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 116)

FIG. 11 (cont'd)

Ab6 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTACCGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 117)

Ab7 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTTATGGAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 118)

FIG. 11 (cont'd)

Ab10 full-length light chain nucleic acid sequence
CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATGCAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 119)

Ab11 full-length light chain nucleic acid sequence
CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATGATAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 120)

FIG. 11 (cont'd)

Ab12 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATGAAAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 121)

Ab13 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATTTTAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 122)

FIG. 11 (cont'd)

Ab14 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATCATAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 123)

Ab15 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATATTAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 124)

FIG. 11 (cont'd)

Ab16 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATAAGAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 125)

Ab17 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATTTGAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 126)

FIG. 11 (cont'd)

Ab18 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATGATAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 127)

Ab19 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATAATAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 128)

FIG. 11 (cont'd)

Ab20 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATCAGAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 129)

Ab21 full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATCGTAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 130)

FIG. 11 (cont'd)

Ab22 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATAGTAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 131)

Ab23 full-length light chain nucleic acid sequence

CCCACC<u>ATGGAAGCCCCAGCGCAGCTTCTCTTCCTCCTGCTACTCTGGCTCCC
TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAATACCAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 132)

FIG. 11 (cont'd)

Ab24 full-length light chain nucleic acid sequence

CCCACCATGGAAGCCCCAGCGCAGCTTCTCTTCCTCCTGCTACTCTGGCTCCC
TGATACCACCGGAGACATTGTGATGACCCAGACTCCACTCAGTTTGTCAG
TTACCCCTGGGCAACCAGCCTCTATCTCTTGCAAGTCAAGTCAGAGCCTC
TTATATAGTAATTTGAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 133)

Ab25 full-length light chain nucleic acid sequence

CCCACCATGGAAGCCCCAGCGCAGCTTCTCTTCCTCCTGCTACTCTGGCTCCC
TGATACCACCGGAGACATTGTGATGACCCAGACTCCACTCAGTTTGTCAG
TTACCCCTGGGCAACCAGCCTCTATCTCTTGCAAGTCAAGTCAGAGCCTC
TTATATAGTAATGTTAAAACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 134)

FIG. 11 (cont'd)

KGN full-length light chain nucleic acid sequence

CCCACC<u>ATGGAAGCCCCAGCGCAGCTTCTCTTCCTCCTGCTACTCTGGCTCCC</u>
<u>TGATACCACCGGA</u>GACATTGTGATGACCCAGACTCCACTCAGTTTGTCAG
TTACCCCTGGGCAACCAGCCTCTATCTCTTGCAAGTCAAGTCAGAGCCTC
TTATATAGTAAAGGAAATACCTATTTGAACTGGGTTTTACAGAAGCCAGG
CCAGTCTCCACAGCGCCTAATCTATCTGGTGTCTAAACTGGACTCTGGAG
TCCCTGACAGGTTCTCTGGCAGTGGATCAGGAACAGATTTTACACTGAAA
ATCAGCAGAGTGGAGGCTGAGGATGTGGGAGTTTATTACTGCGTGCAAG
GTTCACATTTTCACACGTTCGGTCAAGGGACCAAGCTGGAGATTAAACGA
ACTGTGGCAGCACCAAGCGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAGC
CTCAGCAGCACCCTGACGCTGAGCAAAGCAGACTACGAGAAACACAAAG
TCTACGCCTGCGAAGTCACCCATCAGGGCCTGAGCTCGCCCGTCACAAA
GAGCTTCAACAGGGGAGAGTGTTAGTGA (SEQ ID NO: 135)

FIG. 12

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 H-CDR1 amino acid sequence

GFPFSNYWMN (SEQ ID NO: 7)

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 H-CDR2 amino acid sequence

QIRLKSNNYATHYAESVKG (SEQ ID NO: 8)

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 H-CDR3 amino acid sequence

TPIDY (SEQ ID NO: 9)

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 L-CDR2 amino acid sequence

LVSKLDS (SEQ ID NO: 34)

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 L-CDR3 amino acid sequence

VQGSHFHT (SEQ ID NO: 35)

FIG. 13

| Antibody | L-CDR1 | SEQ ID NO |
|---|---|---|
| Ab1 | KSSQSLLYSDGKTYLN | 11 |
| Ab2 | KSSQSLLYSHGKTYLN | 12 |
| Ab3 | KSSQSLLYSKGKTYLN | 13 |
| Ab4 | KSSQSLLYSQGKTYLN | 14 |
| Ab5 | KSSQSLLYSRGKTYLN | 15 |
| Ab6 | KSSQSLLYSTGKTYLN | 16 |
| Ab7 | KSSQSLLYSYGKTYLN | 17 |
| Ab10 | KSSQSLLYSNAKTYLN | 18 |
| Ab11 | KSSQSLLYSNDKTYLN | 19 |
| Ab12 | KSSQSLLYSNEKTYLN | 20 |
| Ab13 | KSSQSLLYSNFKTYLN | 21 |
| Ab14 | KSSQSLLYSNHKTYLN | 22 |
| Ab15 | KSSQSLLYSNIKTYLN | 23 |
| Ab16 | KSSQSLLYSNKKTYLN | 24 |
| Ab17 | KSSQSLLYSNLKTYLN | 25 |
| Ab18 | KSSQSLLYSNMKTYLN | 26 |
| Ab19 | KSSQSLLYSNNKTYLN | 27 |
| Ab20 | KSSQSLLYSNQKTYLN | 28 |
| Ab21 | KSSQSLLYSNRKTYLN | 29 |
| Ab22 | KSSQSLLYSNSKTYLN | 30 |
| Ab23 | KSSQSLLYSNTKTYLN | 31 |
| Ab24 | KSSQSLLYSNVKTYLN | 32 |
| Ab25 | KSSQSLLYSNYKTYLN | 33 |
| Ab26 | KSSQSLLYSNGKTYLN | 10 |

FIG. 14

Ab1 full-length light chain amino acid sequence

DIVMTQTPLSLSVTPGQPASISC<u>KSSQSLLYSDGKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 36)

Ab2 full-length light chain amino acid sequence

DIVMTQTPLSLSVTPGQPASISC<u>KSSQSLLYSHGKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 37)

Ab3 full-length light chain amino acid sequence

DIVMTQTPLSLSVTPGQPASISC<u>KSSQSLLYSKGKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 38)

Ab4 full-length light chain amino acid sequence

DIVMTQTPLSLSVTPGQPASISC<u>KSSQSLLYSQGKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 39)

Ab5 full-length light chain amino acid sequence

DIVMTQTPLSLSVTPGQPASISC<u>KSSQSLLYSRGKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 40)

FIG. 14 (cont'd)

Ab6 full-length light chain amino acid sequence

DIVMTQTPLSLSVTPGQPASISC<u>KSSQSLLYSTGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 41)

Ab7 full-length light chain amino acid sequence

DIVMTQTPLSLSVTPGQPASISC<u>KSSQSLLYSYGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 42)

Ab10 full-length light chain amino acid sequence

DIVMTQTPLSLSVTPGQPASISC<u>KSSQSLLYSNAKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 43)

Ab11 full-length light chain amino acid sequence

DIVMTQTPLSLSVTPGQPASISC<u>KSSQSLLYSNDKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 44)

Ab12 full-length light chain amino acid sequence

DIVMTQTPLSLSVTPGQPASISC<u>KSSQSLLYSNEKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 45)

FIG. 14 (cont'd)

Ab13 full-length light chain amino acid sequence

DIVMTQTPLSLSVTPGQPASISC<u>KSSQSLLYSNFKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 46)

Ab14 full-length light chain amino acid sequence

DIVMTQTPLSLSVTPGQPASISC<u>KSSQSLLYSNHKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 47)

Ab15 full-length light chain amino acid sequence

DIVMTQTPLSLSVTPGQPASISC<u>KSSQSLLYSNIKTYLN</u>WVLQKPGQSPQRLIY<u>LVS
KLDS</u>GVPDRFSGSGSGTDFTLKISRVEAEDVGVYYC<u>VQGSHFHT</u>FGQGTKLEIKR
TVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ
ID NO: 48)

Ab16 full-length light chain amino acid sequence

DIVMTQTPLSLSVTPGQPASISC<u>KSSQSLLYSNKKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 49)

Ab17 full-length light chain amino acid sequence

DIVMTQTPLSLSVTPGQPASISC<u>KSSQSLLYSNLKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 50)

FIG. 14 (cont'd)

Ab18 full-length light chain amino acid sequence

DIVMTQTPLSLSVTPGQPASISC<u>KSSQSLLYSNMKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 51)

Ab19 full-length light chain amino acid sequence

DIVMTQTPLSLSVTPGQPASISC<u>KSSQSLLYSNNKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 52)

Ab20 full-length light chain amino acid sequence

DIVMTQTPLSLSVTPGQPASISC<u>KSSQSLLYSNQKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 53)

Ab21 full-length light chain amino acid sequence

DIVMTQTPLSLSVTPGQPASISC<u>KSSQSLLYSNRKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 54)

Ab22 full-length light chain amino acid sequence

DIVMTQTPLSLSVTPGQPASISC<u>KSSQSLLYSNSKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 55)

FIG. 14 (cont'd)

Ab23 full-length light chain amino acid sequence

DIVMTQTPLSLSVTPGQPASISC<u>KSSQSLLYSNTKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 56)

Ab24 full-length light chain amino acid sequence

DIVMTQTPLSLSVTPGQPASISC<u>KSSQSLLYSNVKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 57)

Ab25 full-length light chain amino acid sequence

DIVMTQTPLSLSVTPGQPASISC<u>KSSQSLLYSNYKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 58)

KGN full-length light chain amino acid sequence

DIVMTQTPLSLSVTPGQPASISC<u>KSSQSLLYSKGNTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC
(SEQ ID NO: 2)

FIG. 15

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 heavy chain variable domain amino acid sequence

EVQLVESGGGLVQPGGSLRLSCAAS<u>GFPFSNY</u>WMNWVRQAPGKGLEWVG<u>QIRL
KSNNYATHYAESVKG</u>RFTISRDDSKNSLYLQMNSLKTEDTAVYYC<u>TPIDY</u>WGQG
TTVTVSS (SEQ ID NO: 59)

Ab26 light chain variable domain amino acid sequence

DIVMTQTPLSLSVTPGQPASISC<u>KSSQSLLYSNGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 60)

Ab1 light chain variable domain amino acid sequence

DIVMTQTPLSLSVTPGQPASISC<u>KSSQSLLYSDGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 61)

Ab2 light chain variable domain amino acid sequence

DIVMTQTPLSLSVTPGQPASISC<u>KSSQSLLYSHGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 62)

Ab3 light chain variable domain amino acid sequence

DIVMTQTPLSLSVTPGQPASISC<u>KSSQSLLYSKGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 63)

Ab4 light chain variable domain amino acid sequence

DIVMTQTPLSLSVTPGQPASISC<u>KSSQSLLYSQGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 64)

FIG. 15 (cont'd)

Ab5 light chain variable domain amino acid sequence

DIVMTQTPLSLSVTPGQPASISC<u>KSSQSLLYSRGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 65)

Ab6 light chain variable domain amino acid sequence

DIVMTQTPLSLSVTPGQPASISC<u>KSSQSLLYSTGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 66)

Ab7 light chain variable domain amino acid sequence

DIVMTQTPLSLSVTPGQPASISC<u>KSSQSLLYSYGKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 67)

Ab10 light chain variable domain amino acid sequence

DIVMTQTPLSLSVTPGQPASISC<u>KSSQSLLYSNAKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 68)

Ab11 light chain variable domain amino acid sequence

DIVMTQTPLSLSVTPGQPASISC<u>KSSQSLLYSNDKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 69)

Ab12 light chain variable domain amino acid sequence

DIVMTQTPLSLSVTPGQPASISC<u>KSSQSLLYSNEKTYLN</u>WVLQKPGQSPQRLIY<u>LV
SKLDS</u>GVPDRFSGSGSGTDFTLKISRVEAEDVGVYYC<u>VQGSHFHT</u>FGQGTKLEIK
(SEQ ID NO: 70)

FIG. 15 (cont'd)

Ab13 light chain variable domain amino acid sequence

DIVMTQTPLSLSVTPGQPASISC<u>KSSQSLLYSNFKTYLN</u>WVLQKPGQSPQRLIY<u>LVSKLDS</u>GVPDRFSGSGSGTDFTLKISRVEAEDVGVYYC<u>VQGSHFHT</u>FGQGTKLEIK (SEQ ID NO: 71)

Ab14 light chain variable domain amino acid sequence

DIVMTQTPLSLSVTPGQPASISC<u>KSSQSLLYSNHKTYLN</u>WVLQKPGQSPQRLIY<u>LVSKLDS</u>GVPDRFSGSGSGTDFTLKISRVEAEDVGVYYC<u>VQGSHFHT</u>FGQGTKLEIK (SEQ ID NO: 72)

Ab15 light chain variable domain amino acid sequence

DIVMTQTPLSLSVTPGQPASISC<u>KSSQSLLYSNIKTYLN</u>WVLQKPGQSPQRLIY<u>LVSKLDS</u>GVPDRFSGSGSGTDFTLKISRVEAEDVGVYYC<u>VQGSHFHT</u>FGQGTKLEIK (SEQ ID NO: 73)

Ab16 light chain variable domain amino acid sequence

DIVMTQTPLSLSVTPGQPASISC<u>KSSQSLLYSNKKTYLN</u>WVLQKPGQSPQRLIY<u>LVSKLDS</u>GVPDRFSGSGSGTDFTLKISRVEAEDVGVYYC<u>VQGSHFHT</u>FGQGTKLEIK (SEQ ID NO: 74)

Ab17 light chain variable domain amino acid sequence

DIVMTQTPLSLSVTPGQPASISC<u>KSSQSLLYSNLKTYLN</u>WVLQKPGQSPQRLIY<u>LVSKLDS</u>GVPDRFSGSGSGTDFTLKISRVEAEDVGVYYC<u>VQGSHFHT</u>FGQGTKLEIK (SEQ ID NO: 75)

Ab18 light chain variable domain amino acid sequence

DIVMTQTPLSLSVTPGQPASISC<u>KSSQSLLYSNMKTYLN</u>WVLQKPGQSPQRLIY<u>LVSKLDS</u>GVPDRFSGSGSGTDFTLKISRVEAEDVGVYYC<u>VQGSHFHT</u>FGQGTKLEIK (SEQ ID NO: 76)

Ab19 light chain variable domain amino acid sequence

DIVMTQTPLSLSVTPGQPASISC<u>KSSQSLLYSNNKTYLN</u>WVLQKPGQSPQRLIY<u>LVSKLDS</u>GVPDRFSGSGSGTDFTLKISRVEAEDVGVYYC<u>VQGSHFHT</u>FGQGTKLEIK (SEQ ID NO: 77)

FIG. 15 (cont'd)

Ab20 light chain variable domain amino acid sequence

DIVMTQTPLSLSVTPGQPASISC<u>KSSQSLLYSNQKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
(SEQ ID NO: 78)

Ab21 light chain variable domain amino acid sequence

DIVMTQTPLSLSVTPGQPASISC<u>KSSQSLLYSNRKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
(SEQ ID NO: 79)

Ab22 light chain variable domain amino acid sequence

DIVMTQTPLSLSVTPGQPASISC<u>KSSQSLLYSNSKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
(SEQ ID NO: 80)

Ab23 light chain variable domain amino acid sequence

DIVMTQTPLSLSVTPGQPASISC<u>KSSQSLLYSNTKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
(SEQ ID NO: 81)

Ab24 light chain variable domain amino acid sequence

DIVMTQTPLSLSVTPGQPASISC<u>KSSQSLLYSNVKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
(SEQ ID NO: 82)

Ab25 light chain variable domain amino acid sequence

DIVMTQTPLSLSVTPGQPASISC<u>KSSQSLLYSNYKTYLN</u>WVLQKPGQSPQRLIY<u>LV</u>
<u>SKLDS</u>GVPDRFSGSGSGTDFTLKISRVEAEDVGVYYC<u>VQGSHFHT</u>FGQGTKLEIK
(SEQ ID NO: 83)

FIG. 16

Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN heavy chain variable domain nucleic acid sequence

GAGGTACAGCTGGTGGAGTCGGGAGGAGGCTTGGTACAGCCTGGGGGTTCTC
TGAGACTCTCCTGTGCAGCTTCTGGATTCCCATTCAGTAACTACTGGATGAAC
TGGGTCCGCCAGGCTCCAGGGAAGGGACTTGAGTGGGTGGGTCAAATTAGAT
TGAAATCTAATAATTATGCAACACATTATGCGGAGTCTGTGAAAGGGCGGTT
CACCATCTCCAGAGATGATTCCAAAAACAGCCTCTATCTTCAAATGAATTCCC
TGAAAACTGAAGACACTGCCGTTTATTACTGTACCCCAATTGACTATTGGGC
CAAGGCACCACTGTCACAGTCTCCTCA (SEQ ID NO: 84)

Ab26 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 85)

Ab1 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTGATGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 88)

Ab2 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTCACGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 89)

FIG. 16 (cont'd)

Ab3 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAAAGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 90)

Ab4 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTCAAGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 91)

Ab5 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTCGCGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 92)

Ab6 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTACCGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 93)

FIG. 16 (cont'd)

Ab7 light chain variable domain nucleic acid sequence

GACATTGTGATGACCCAGACTCCACTCAGTTTGTCAGTTACCCTGGGCAACC
AGCCTCTATCTCTTGCAAGTCAAGTCAGAGCCTCTTATATAGTTATGGAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 94)

Ab10 light chain variable domain nucleic acid sequence

GACATTGTGATGACCCAGACTCCACTCAGTTTGTCAGTTACCCTGGGCAACC
AGCCTCTATCTCTTGCAAGTCAAGTCAGAGCCTCTTATATAGTAATGCAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 95)

Ab11 light chain variable domain nucleic acid sequence

GACATTGTGATGACCCAGACTCCACTCAGTTTGTCAGTTACCCTGGGCAACC
AGCCTCTATCTCTTGCAAGTCAAGTCAGAGCCTCTTATATAGTAATGATAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 96)

Ab12 light chain variable domain nucleic acid sequence

GACATTGTGATGACCCAGACTCCACTCAGTTTGTCAGTTACCCTGGGCAACC
AGCCTCTATCTCTTGCAAGTCAAGTCAGAGCCTCTTATATAGTAATGAAAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 97)

FIG. 16 (cont'd)

Ab13 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATTTTAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 98)

Ab14 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATCATAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 99)

Ab15 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATATTAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 100)

Ab16 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATAAGAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 101)

FIG. 16 (cont'd)

Ab17 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATTTGAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 102)

Ab18 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATGATAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 103)

Ab19 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATAATAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 104)

Ab20 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATCAGAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 105)

FIG. 16 (cont'd)

Ab21 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATCGTAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 106)

Ab22 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATAGTAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 107)

Ab23 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATACCAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 108)

Ab24 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATTTGAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 109)

FIG. 16 (cont'd)

Ab25 light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAATGTTAAAA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 110)

KGN light chain variable domain nucleic acid sequence

GACATTGTGATGACCCAGACTCCACTCAGTTTGTCAGTTACCCCTGGGCAACC
AGCCTCTATCTCTTGCAAGTCAAGTCAGAGCCTCTTATATAGTAAAGGAAATA
CCTATTTGAACTGGGTTTTACAGAAGCCAGGCCAGTCTCCACAGCGCCTAATC
TATCTGGTGTCTAAACTGGACTCTGGAGTCCCTGACAGGTTCTCTGGCAGTGG
ATCAGGAACAGATTTTACACTGAAAATCAGCAGAGTGGAGGCTGAGGATGTG
GGAGTTTATTACTGCGTGCAAGGTTCACATTTTCACACGTTCGGTCAAGGGAC
CAAGCTGGAGATTAAA (SEQ ID NO: 111)

FIG. 18
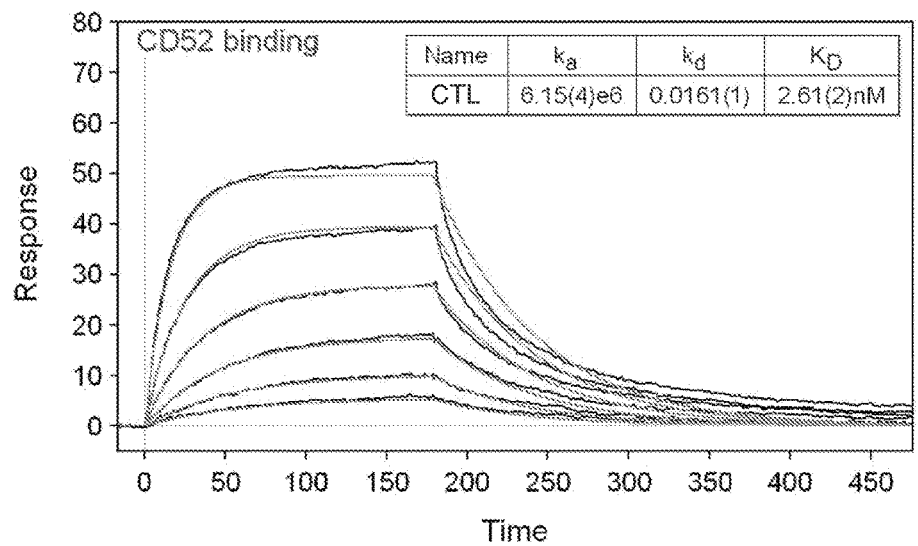
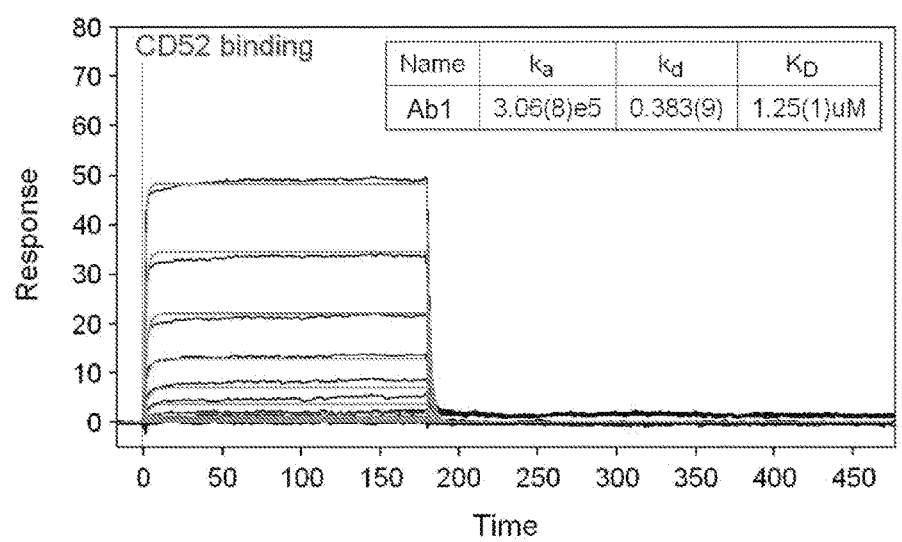

ANTI-CD52 ANTIBODIES

CROSS REFERENCE TO RELATED APPLICATIONS

This application is a United States National Stage under 35 U.S.C. §371 of International Application No. PCT/US14/26159, filed Mar. 13, 2014 (pending), which claims priority from U.S. provisional application 61/794,576, filed on Mar. 15, 2013 (expired). The disclosure of each of these applications is incorporated by reference in its entirety.

SEQUENCE LISTING

The instant application contains a Sequence Listing that has been submitted electronically as a text file in ASCII format and is hereby incorporated by reference in its entirety. Said text file, created on Sep. 11, 2015, is named 001662-0041-301-SL and is 142,624 bytes in size

FIELD OF THE INVENTION

This invention relates generally to antibodies, and more specifically to antibodies having binding specificity for human CD52.

BACKGROUND OF THE INVENTION

CD52 is a glycosylated, glycosylphosphatidylinositol (GPI)-anchored cell surface protein found in abundance (500,000 molecules/cell) on a variety of normal and malignant lymphoid cells (e.g., T and B cells). See, e.g., Hale et al., *J Biol Regul Homeost Agents* 15:386-391 (2001); Huh et al., *Blood* 92: Abstract 4199 (1998); Elsner et al., *Blood* 88:4684-4693 (1996); Gilleece et al., *Blood* 82:807-812 (1993); Rodig et al., *Clin Cancer Res* 12:7174-7179 (2006); Ginaldi et al., *Leuk Res* 22:185-191 (1998). CD52 is expressed at lower levels on myeloid cells such as monocytes, macrophages, and dendritic cells, with little expression found on mature natural killer (NK) cells, neutrophils, and hematological stem cells. Id. In all, CD52 is present on at least 95% of all human peripheral blood lymphocytes and monocytes/macrophages (Hale G, et al., "The CAMPATH-1 antigen (CD52)," Tissue Antigens, 35:178-327 (1990)). CD52 is also produced by epithelial cells in the epididymis and duct deferens, and is acquired by sperm during passage through the genital tract (Hale et al., 2001, supra; Domagala et al., *Med Sci Monit* 7:325-331 (2001)). The exact biological function of CD52 remains unclear but some evidence suggests that it may be involved in T cell migration and co-stimulation (Rowan et al., *Int Immunol* 7:69-77 (1995); Masuyama et al., *J Exp Med* 189:979-989 (1999); Watanabe et al., *Clin Immunol* 120:247-259 (2006)).

Several anti-CD52 monoclonal antibodies have been developed. Campath-1H® (also known as alemtuzumab, Campath®, MabCampath®) is a humanized anti-human CD52 monoclonal antibody that exhibits potent in vitro cytotoxic effects (antibody-dependent cell mediated cytotoxicity (ADCC) and complement-dependent cytotoxicity (CDC)). Alemtuzumab recognizes an epitope that consists of the carboxy terminal four amino acids of the mature CD52 protein and a portion of the negatively charged GPI anchor. Additional anti-human CD52 monoclonal antibodies have been generated. However, the binding affinity of some of these antibodies decreases in storage and under certain pH and temperature conditions. Thus, a need exists for anti-CD52 antibodies that have a reduced propensity to undergo this change.

SUMMARY OF THE INVENTION

The invention features anti-human CD52 antibodies that have been engineered to retain binding affinity over time and under high pH and temperature conditions. The terms "antibody" and "immunoglobulin" are used interchangeably herein. Isolated nucleic acids, recombinant vectors and host cells comprising a sequence that encodes an anti-CD52 antibody light chain or heavy chain, and a method of preparing an anti-CD52 antibody are also provided.

Ab26 is a humanized anti-human CD52 monoclonal antibody having a heavy chain amino acid sequence of SEQ ID NO: 3 minus the signal sequence and a light chain amino acid sequence of SEQ ID NO: 4 minus the signal sequence. Ab26 has reduced CD52 binding affinity and potency over time in storage. We have unexpectedly discovered that variants of Ab26 with certain single amino acid substitutions at position 11 of the light chain CDR1 (e.g., monoclonal antibodies Ab21, Ab16, and Ab20) not only retain or surpass Ab26's human CD52-binding affinity, but also demonstrate significantly improved stability compared to Ab26. The variant antibodies such as Ab21, Ab16, and Ab20 have demonstrated comparable or improved biological potency in vitro and in vivo as compared to Ab26. These variants are useful for therapeutic and diagnostic applications.

In some embodiments, the anti-human CD52 antibody or antigen-binding fragment of the invention comprises a heavy chain variable region and a light chain variable region, wherein said heavy chain variable region comprises: the heavy chain CDR1 of SEQ ID NO: 7; the heavy chain CDR2 of SEQ ID NO: 8; and the heavy chain CDR3 of SEQ ID NO: 9, and wherein said light chain variable region comprises the light chain CDR1 of SEQ ID NO: 86; the light chain CDR2 of SEQ ID NO: 34; and the light chain CDR3 of SEQ ID NO: 35. In further embodiments, residue 11 in SEQ ID NO: 86 may be K, R, Q, H, S, Y, A, D, E, F, I, L, M, N, T, or V. In one embodiment, residue 11 in SEQ ID NO: 86 is K. In another embodiment, residue 11 in SEQ ID NO: 86 is R. In yet another embodiment, residue 11 in SEQ ID NO: 86 is Q.

In some embodiments, the heavy chain variable region of the anti-CD52 antibody or fragment comprises SEQ ID NO: 59. In additional embodiments, the light chain variable region of the anti-CD52 antibody or fragment comprises a sequence selected from the group consisting of SEQ ID NOs: 68, 69, 70, 71, 72, 73, 74, 75, 76, 77, 78, 79, 80, 81, 82, and 83. For example, the heavy and light chains of the antibody or fragment of the invention may comprise: a) SEQ ID NOs: 59 and 68, respectively; b) SEQ ID NOs: 59 and 69, respectively; c) SEQ ID NOs: 59 and 70, respectively; d) SEQ ID NOs: 59 and 71, respectively; e) SEQ ID NOs: 59 and 72, respectively; f) SEQ ID NOs: 59 and 73, respectively; g) SEQ ID NOs: 59 and 74, respectively; h) SEQ ID NOs: 59 and 75, respectively; i) SEQ ID NOs: 59 and 76, respectively; j) SEQ ID NOs: 59 and 77, respectively; k) SEQ ID NOs: 59 and 78, respectively; l) SEQ ID NOs: 59 and 79, respectively; m) SEQ ID NOs: 59 and 80, respectively; n) SEQ ID NOs: 59 and 81, respectively; o) SEQ ID NOs: 59 and 82, respectively; or p) SEQ ID NOs: 59 and 83, respectively.

In some embodiments, the antibody or fragment comprises a heavy chain amino acid sequence of SEQ ID NO: 3 without the signal sequence. In additional embodiments, the antibody or fragment comprises a light chain amino acid sequence selected from the group consisting of SEQ ID NOs: 43, 44, 45, 46, 47, 48, 49, 50, 51, 52, 53, 54, 55, 56, 57, and 58. For example, the antibody or fragment may comprise (a) a heavy chain amino acid sequence of SEQ ID NO: 3 without the signal sequence and a light chain amino acid sequence of SEQ ID NO: 49; (b) a heavy chain amino acid sequence of SEQ ID NO: 3 without the signal sequence and a light chain amino acid sequence of SEQ ID NO: 53; or (c) a heavy chain amino acid sequence of SEQ ID NO: 3 without the signal sequence and a light chain amino acid sequence of SEQ ID NO: 54.

In some embodiments, the antibody of the invention is an immunoglobulin G (IgG). In additional embodiments, the antibody comprises a human Fc region (e.g., a human IgG1, IgG2, IgG3, or IgG4 Fc region). The invention also encompasses an antigen-binding fragment of any of the antibodies of the invention, wherein said fragment is selected from the group consisting of an scFv fragment, an Fv fragment, an Fab fragment, an F(ab')2 fragment, a minibody, a diabody, a triabody, and a tetrabody.

In some embodiments, the antibody of the invention is monoclonal. In further embodiments the antibody and antigen-binding fragment is humanized. The heavy chain C-terminal lysine of an antibody or fragment of the invention may optionally be cleaved.

The invention also relates to an isolated nucleic acid molecule comprising a nucleotide sequence that encodes the heavy chain or an antigen-binding fragment thereof, or the light chain or an antigen-binding fragment thereof, or both, of an antibody. In some embodiments, the isolated nucleic acid molecule comprises the nucleotide sequence of SEQ ID NO: 95, 96, 97, 98, 99, 100, 101, 102, 103, 104, 105, 106, 107, 108, 109, 110, 119, 120, 121, 122, 123, 124, 125, 126, 127, 128, 129, 130, 131, 132, 133, or 134. The invention also encompasses a recombinant vector (e.g., an expression vector) comprising said nucleic acid molecule. In some embodiments, the invention encompasses an isolated host cell comprising said vector.

The invention also encompasses an isolated cell line that produces an anti-CD52 antibody or fragment described herein or the heavy or light chain of said antibody or fragment. In some embodiments, the invention relates to a method of making an anti-human CD52 antibody or an antigen-binding fragment thereof, comprising (1) maintaining the host cell or the cell line described herein under conditions appropriate for expression of the antibody or fragment; and (2) recovering the antibody or fragment.

The invention encompasses a composition comprising the antibody or antigen-binding fragment described herein and a pharmaceutically acceptable vehicle or carrier.

The invention relates to a method for treating a patient in need thereof, comprising administering to the patient an effective amount of the antibody or an antigen-binding fragment described herein. In some embodiments, the invention encompasses a method for treating an autoimmune disease (e.g., multiple sclerosis) in a patient in need thereof, comprising administering to the patient an antibody or an antigen-binding fragment described herein. In some embodiments, the invention encompasses a method for treating cancer (e.g., chronic lymphocytic leukemia) in a patient in need thereof, comprising administering to the patient an antibody or an antigen-binding fragment described herein. The invention also relates to a method of inhibiting angiogenesis in a patient in need thereof, comprising administering to the patient an antibody or an antigen-binding fragment described herein.

In some embodiments, the invention relates to use of the antibody or antigen-binding fragment described herein for the treatment of, or the preparation of a medicament for treating, an autoimmune disease (e.g., multiple sclerosis) in a patient in need thereof. The invention also relates to use of the antibody or antigen-binding fragment described herein for the treatment of, or the preparation of a medicament for treating, cancer (e.g., chronic lymphocytic leukemia) in a patient in need thereof. The invention further relates to use of the antibody or antigen-binding fragment described herein for the treatment of excessive angiogenesis, or for the preparation of a medicament for inhibiting angiogenesis, in a patient in need thereof.

BRIEF DESCRIPTION OF THE DRAWINGS

FIG. 5 depicts results from experiments characterizing additional anti-CD52 antibodies. The table and graphs show the results of BIACORE™ binding assays and Octet expression level measurements. "KGN" refers to an anti-CD52 antibody with the heavy chain sequence of SEQ ID NO: 3 and the light chain sequence of SEQ ID NO: 2.

FIG. 9 shows the amino acid sequence of a wild-type human CD52 protein (GenBank Accession No. AAH00644.1) (SEQ ID NO: 1).

FIG. 10 shows the full-length heavy chain amino acid sequence of antibodies Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN (SEQ ID NO: 3) and the full-length light chain amino acid sequence of antibody Ab26 (SEQ ID NO: 4). The signal sequences are boldfaced and italicized and the CDRs are underlined.

FIG. 11 shows the full-length heavy chain nucleic acid sequence of antibodies Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN (SEQ ID NO: 5) and the full-length light chain nucleic acid sequences of antibodies Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN. The signal sequences are underlined, and the open reading frames are in boldface.

FIG. 12 shows the amino acid sequences of the H-CDR1 (SEQ ID NO: 7), H-CDR2 (SEQ ID NO: 8), H-CDR3 (SEQ ID NO: 9), L-CDR2 (SEQ ID NO: 34), and L-CDR3 (SEQ ID NO: 35) of antibodies Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25.

FIG. 13 shows the amino acid sequences of the L-CDR1 of antibodies Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and Ab26.

FIG. 14 shows the full-length light chain amino acid sequences of antibodies Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25. The CDRs are underlined.

FIG. 15 shows the heavy and light chain variable domain amino acid sequences of antibodies Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25. The CDRs are underlined.

FIG. 16 shows the nucleic acid sequences of the heavy chain variable domain and the light chain variable domains of antibodies Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN.

FIG. 18 depicts results from experiments characterizing the Ab1 antibody purified from CHO cells. The graphs show results of BIACORE™ assays measuring affinity of the Ab1 antibody (lower panel) and Ab26 antibody (CTL) (upper panel) for a CD52 peptide.

DETAILED DESCRIPTION OF THE INVENTION

Figure 1:
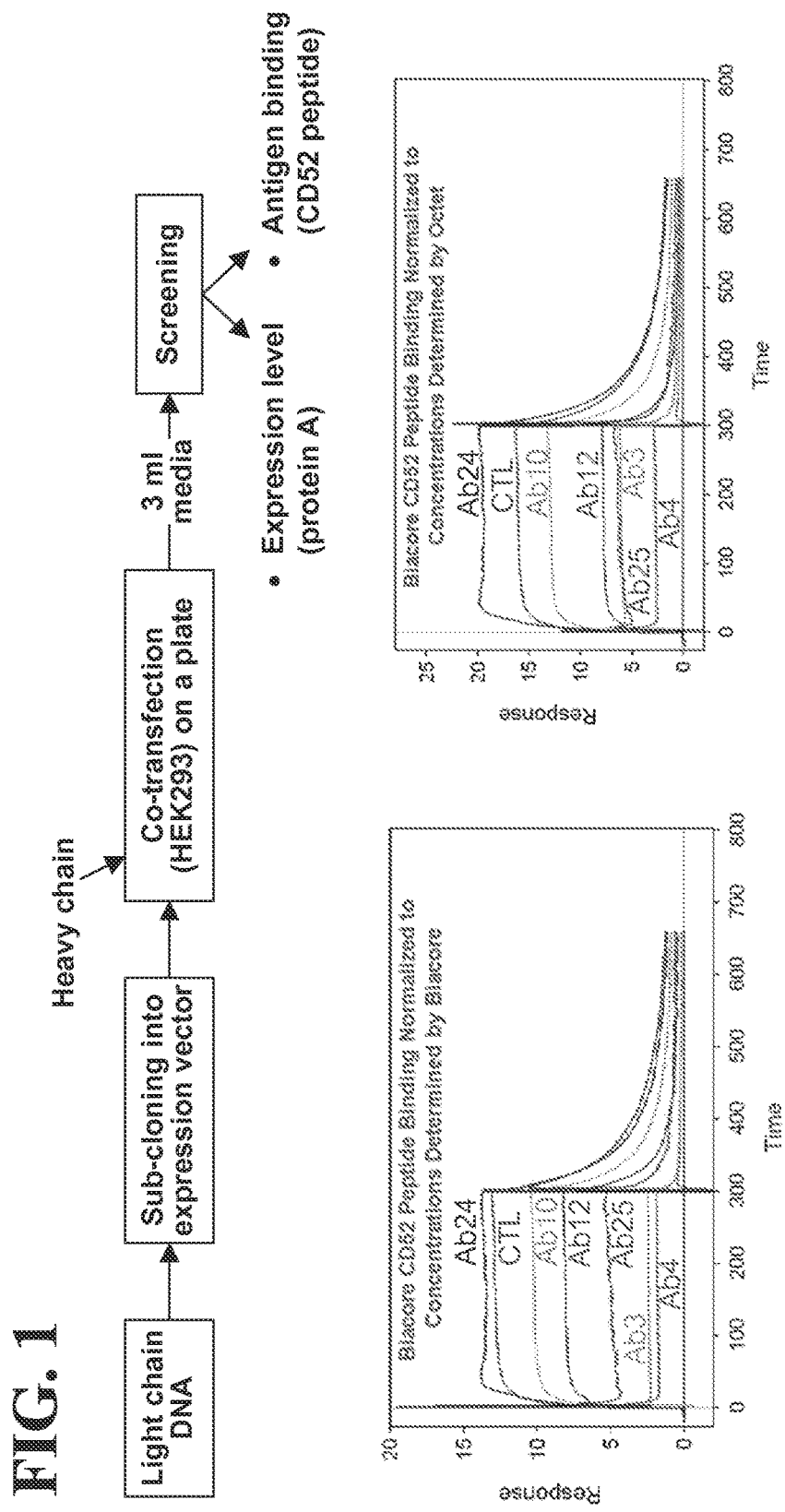
FIG. 1 depicts results from quick affinity screening of anti-CD52 antibodies. The upper panel is a flow chart of the preparation of the antibodies. The middle panel graphs and lower panel tables show the results of BIACORE™ binding assays and Octet expression level measurements.

This invention is based on our discovery that certain anti-CD52 antibodies lose stability and demonstrate reduced binding affinity over time in storage or under certain pH and temperature conditions. We have generated variant antibodies comprising amino acid substitutions at a single position (position 11) in the light chain CDR1 (L-CDR1) of the parent antibodies. We have discovered that some of these variant antibodies demonstrate not only similar or improved antigen-binding characteristics and biological activity, including in vivo potency, but also enhanced stability, as compared to the parent antibody.

Included in the present invention are anti-human CD52 antibodies, antigen-binding fragments (i.e., portions) of the antibodies, the light chains of the antibodies, the heavy chains of the antibodies, and fragments of these light chains or heavy chains. The invention relates to mature antibodies or chains thereof, such as glycosylated antibodies, as well as immature or precursor antibody protein. The invention also relates to nucleic acid molecules (e.g., vectors) that encode both these immature or mature proteins, to host cells that comprise such nucleic acids, to methods of producing immature and mature proteins, and to methods of using the antibodies.

The antibodies and antigen-binding portions of this invention can be used to treat a subject in need thereof, e.g., a human patient, for a variety of diseases and conditions mediated or caused by CD52-bearing cells, such as certain immune-mediated disease (IMD) indications. A mechanism of action may be that the anti-CD52 antibodies deplete those cells (e.g., lymphocytes or cancerous CD52$^+$ cells) by causing cell death. For example, the antibodies can be used to treat auto-immune diseases (e.g., multiple sclerosis (MS), rheumatoid arthritis, systemic lupus erythematosus, vasculitis, myositis, and Wegener's disease) through lymphocyte depletion—a type of immunosuppression achieved by reducing the population of circulating lymphocytes, e.g., T cells and/or B cells, resulting in lymphopenia. The antibodies of the invention also can be used to treat cancer, for example, leukemias (e.g., chronic lymphocytic leukemia) and lymphomas (e.g., non-Hodgkin's lymphoma) or used in tissue transplantation (e.g., solid organ transplants (e.g., kidney transplant) and stem cell transplants). The antibodies of this invention also can be used to enrich hematopoietic stem cells, for example, in ex vivo applications (See, e.g., Lim et al., J. Hematology & Oncology 1:19 (2008)).

Antigen-Binding Properties of the Present Antibodies

The antibodies of this invention have binding specificity (e.g., epitopic specificity) for, or are selective for binding to, human CD52 or a portion thereof. These antibodies bind specifically to a CD52 molecule, and do not bind specifically to non-CD52 molecules. Specific binding between an anti-CD52 antibody and CD52 can be determined, for example, by measuring $EC_{50}$ of the antibody's binding to CD52$^+$ cells by flow cytometry. Specific binding can be indicated by an $EC_{50}$ of less than 10 µg/ml (e.g., as determined by flow cytometry). The antibodies described herein can have binding specificity for a human CD52 or a fragment thereof.

Binding assays can be performed with an isolated or recombinant human CD52; peptides derived from human CD52; or cells expressing human CD52 (e.g., human T and/or B cells, recombinant host cells expressing a nucleic acid encoding human CD52, or cell membrane fractions of such cells). In addition, the antibodies can have binding specificity for one or more forms of human CD52 (e.g., glycosylated human CD52; de-glycosylated human CD52; non-glycosylated human CD52; and allelic variants). In one embodiment, the antibodies have binding specificity for a naturally occurring, endogenous or wild-type human CD52. The amino acid sequence of a wild-type human CD52 is set out in FIG. 9 (SEQ ID NO: 1).

"Antigen-binding affinity" is a term of art that describes the strength of a binding interaction and typically refers to the overall strength of binding of an antibody to its antigen. In some embodiments, the present antibody binds to human CD52 with an affinity indicated by, e.g., (1) a $K_D$ ($K_D=K_{off}$ (kd)/$K_{on}$ (ka)) of $1\times10^{-7}$ M or less, preferably $1\times10^{-8}$ M or less, more preferably $1\times10^{-9}$ M or less, advantageously $1\times10^{-10}$ M or less, and most preferably $1\times10^{-11}$ M or $1\times10^{-12}$. For example, the $K_D$ ranges from 100 nM to 1 pM (i.e., $1\times10^{-7}$ to $1\times10^{-12}$ M), from 50 nM to 1 pM, from 5 nM to 1 pM, or from 1 nM to 1 pM. A desired antigen-binding affinity may also be indicated by a $K_{off}$ rate constant of $5\times10^{-1}$ s$^{-1}$ or less, preferably $1\times10^{-2}$ s$^{-1}$ or less, advantageously $1\times10^{-3}$ s$^{-1}$ or less, more preferably $1\times10^{4}$ s$^{-1}$ or less, still more preferably $1\times10^{-5}$ s$^{-1}$ or less, and most preferably $1\times10^{-6}$ s$^{-1}$ or less, as determined by surface plasmon resonance. For example, the $K_{off}$ rate constant may range from $5\times10^{-1}$ s$^{-1}$ to $1\times10^{-7}$ s$^{-1}$, from $1\times10^{-2}$ s$^{-1}$ to $1\times10^{-6}$ s$^{-1}$, or from $5\times10^{-3}$ s$^{-1}$ to $1\times10^{-5}$ s$^{-1}$. A desired antigen-binding strength in a particular assay or setting may also be indicated by an $EC_{50}$ of no more than 10 µg/ml, e.g., an $EC_{50}$ of 0.1-10 µg/ml.

The antibodies of this invention include those that bind to an epitope on CD52 that is the same as, or overlaps with, the CD52 epitope bound by antibody Ab26, or any of its variants exemplified herein. Epitope binding can be readily determined using a variety of techniques such as competitive binding assays. An "epitope" as used herein includes any protein determinant capable of specific binding to an antibody. Epitopic determinants generally consist of chemically active surface groupings of molecules such as amino acids and/or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another in the primary polypeptide sequence.

In one embodiment, to determine if a test antibody binds to the same or overlapping epitope of a particular anti-CD52 antibody of this invention, one allows the anti-CD52 antibody of the invention to bind to CD52 under saturating conditions and then measures the ability of the test antibody to bind to CD52. If the test antibody is able to bind to CD52 at the same time as the reference anti-CD52 antibody, then one can infer that the test antibody binds to a different epitope than the reference anti-CD52 antibody. However, if the test antibody is not able to bind to CD52 at the same time, then one can infer that the test antibody binds to an epitope that is the same as, or overlaps with, the epitope bound by the reference anti-CD52 antibody, or to an epitope that is in close proximity to the epitope bound by the reference antibody. This experiment can be performed using ELISA, RIA, BIACORE™, or flow cytometry. To test whether an anti-CD52 antibody cross-competes with another anti-CD52 antibody, one may use the competition method described above in two directions, i.e., determining if the reference antibody blocks the test antibody and vice versa.

Epitope binning can also be useful to characterize the antibodies of this invention. The term "binning" refers to a method to group antibodies based on their antigen-binding characteristics. A high throughput process for "binning" antibodies based upon their cross-competition is described in International Patent Application Publication No. WO 03/48731. "Epitope binning" can be investigated by allowing an unlabeled form of an anti-CD52 antibody "A" to bind to a synthetic peptide corresponding to the sequence of CD52 or to CD52-positive cells. Subsequently a labeled second anti-CD52 antibody "B" is added and one can assess the amount of labeled antibody that can bind relative to a control sample where the cells or synthetic peptide have not been exposed previously to anti-CD52 antibody "A." Alternatively, anti-CD52 antibodies "A" and "B" can be labeled with different fluorochromes or chemicals enabling detection, and one can measure the quantities of both labeled antibodies that can engage the CD52 antigen at the same time using a device capable of detecting the labels, or measure the amounts of both antibodies that simultaneously engage CD52-positive cells by flow cytometry. BIACORE™ and Octet technologies enable one to investigate the competitive binding of unlabelled forms of antibodies. This use of unlabelled forms of antibodies is desired as the chemical modification of some antibodies can compromise the binding activity. See also the technology described in Jia et al., J. Immunol. Methods 288:91-98 (2004), which is useful in performing epitope binning.

In some embodiments, the antibodies of the invention bind human CD52 with an affinity similar to or better than that of antibody Ab26. In a particular embodiment, the antibodies of the invention have the same or similar epitopic specificity and biological function (e.g., lymphocyte-depleting function) of antibody Ab26. In one embodiment, the present antibodies bind to an epitope comprising the QTSS amino acid residues of human CD52.

Structures of the Present Antibodies and Antigen-Binding Fragments

Naturally occurring antibodies have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain (also called the $V_L$ domain) is a C-terminal portion known as the J region. Within the variable region of the heavy chain (also called the $V_H$ domain), there is a D region in addition to the J region. Most of the amino acid sequence variation in antibodies is confined to three separate locations in the V regions known as hypervariable regions or complementarity determining regions (CDRs), which are directly involved in antigen-binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3 and FR4, respectively. The locations of CDR and FR regions and a numbering system have been defined by Kabat et al. See, Kabat, E. A., et al., Sequences of Proteins of Immunological Interest, Fifth Edition, U.S. Department of Health and Human Services, U.S. Government Printing Office (1991); Chothia & Lesk, Canonical Structures for the Hypervariable Regions of Immunoglobulins, J. Mol. Biol., 196: 901-917 (1987); and the IMGT® numbering system (The International ImMunoGeneTics Iinformation System®; Lefranc, M.-P., The Immunologist 7, 132-136 (1999)). Visual inspection and sequence analysis can be carried out to identify the CDR boundaries. For this invention, the CDR sequences are defined by using both the Kabat system and the IMGT system; that is, when the CDRs defined by the two systems do not entirely overlap, all the residues from the sequences defined by both systems are included.

This invention features variants of parent antibody Ab26. The heavy and light chain amino acid and nucleic acid sequences of Ab26 are shown in FIGS. 10 and 11, respectively. Ab26 comprises the heavy chain amino acid sequence of SEQ ID NO: 3 without the signal sequence and the light chain amino acid sequence of SEQ ID NO: 4 without the signal sequence.

In some embodiments of the invention, the CDRs of the present antibody differ from Ab26 in the light chain CDR1 amino sequence at residue 34 of the mature Ab26 protein. Some of these changes greatly improve the variant antibody's stability without affecting its antigen-binding characteristics. If the residue 34 mutation reduces both antigen-binding affinity of the variant antibody, one or more additional mutations may be made in the antibody sequence (for example, in the L-CDR1, L-CDR2, L-CDR2, H-CDR1, H-CDR2, or H-CDR3) to restore the affinity. In some embodiments, residue 34 is changed from G to K, R, Q, H, S, Y, A, D, E, F, I, L, M, N, T, or V. In some embodiments of the invention, the L-CDR1 sequence of the anti-CD52 antibody is selected from the group consisting of SEQ ID NOs: 24, 29, 28, 22, 30, 33, 18, 19, 20, 21, 23, 25, 26, 27, 31, and 32.

CDR sequences of the antibodies specifically illustrated herein are listed in Table 1 below by their SEQ ID NOs.

TABLE 1

SEQ ID NOs of Anti-CD52 Antibodies

| Antibody | H-CDR1 | H-CDR2 | H-CDR3 | L-CDR1 | L-CDR2 | L-CDR3 |
|---|---|---|---|---|---|---|
| Ab1 | 7 | 8 | 9 | 11 | 34 | 35 |
| Ab2 | 7 | 8 | 9 | 12 | 34 | 35 |
| Ab3 | 7 | 8 | 9 | 13 | 34 | 35 |
| Ab4 | 7 | 8 | 9 | 14 | 34 | 35 |
| Ab5 | 7 | 8 | 9 | 15 | 34 | 35 |
| Ab6 | 7 | 8 | 9 | 16 | 34 | 35 |
| Ab7 | 7 | 8 | 9 | 17 | 34 | 35 |
| Ab10 | 7 | 8 | 9 | 18 | 34 | 35 |
| Ab11 | 7 | 8 | 9 | 19 | 34 | 35 |
| Ab12 | 7 | 8 | 9 | 20 | 34 | 35 |
| Ab13 | 7 | 8 | 9 | 21 | 34 | 35 |
| Ab14 | 7 | 8 | 9 | 22 | 34 | 35 |
| Ab15 | 7 | 8 | 9 | 23 | 34 | 35 |
| Ab16 | 7 | 8 | 9 | 24 | 34 | 35 |
| Ab17 | 7 | 8 | 9 | 25 | 34 | 35 |
| Ab18 | 7 | 8 | 9 | 26 | 34 | 35 |
| Ab19 | 7 | 8 | 9 | 27 | 34 | 35 |
| Ab20 | 7 | 8 | 9 | 28 | 34 | 35 |
| Ab21 | 7 | 8 | 9 | 29 | 34 | 35 |
| Ab22 | 7 | 8 | 9 | 30 | 34 | 35 |
| Ab23 | 7 | 8 | 9 | 31 | 34 | 35 |
| Ab24 | 7 | 8 | 9 | 32 | 34 | 35 |
| Ab25 | 7 | 8 | 9 | 33 | 34 | 35 |

In some embodiments, the antibodies of the invention are humanized. The term "anti-CD52 humanized antibody" as used herein refers to an antibody comprising one or more light chain CDRs (CDR1, CDR2 and CDR3) and/or one or more heavy chain CDRs (CDR1, CDR2 and CDR3) of an anti-CD52 antibody of non-human origin, also referred to as the donor antibody (e.g., a murine anti-CD52 antibody); and at least a portion of an antibody of human origin (e.g., framework regions, or framework and constant regions, derived from a light chain and/or a heavy chain of human origin). For example, a humanized antibody is a CDR-grafted antibody with or without framework changes. In some embodiments, humanized antibodies are de-immunized antibodies. See, e.g., Carr U.S. Pat. No. 7,264,806, regarding de-immunized antibodies that have been modified to reduce the number of potential T-cell epitopes, thereby reducing the propensity for the antibody to elicit an immune response upon administration to a human.

Changes in the framework region, such as those that substitute a residue of the framework region of human origin with a residue from the corresponding position of the donor antibody, can be made. See Queen U.S. Pat. No. 5,530,101. One or more mutations, including deletions, insertions and substitutions of one or more amino acids in the framework region, can be made. If desired, framework mutations can be included in a humanized antibody, and sites for mutation can be selected using any suitable method, for example as described in WO 98/06248 and U.S. Pat. No. 6,407,213, the entire disclosures of which are incorporated by reference. In some cases, one or more amino acids flanking one or more CDRs (e.g., 1, 2, 3, 4, 5, 6, 7, 8, 9, 10, 11, or 12 flanking amino acids) in the parental framework are also included in the humanized antibody to enhance antigen-binding affinity. Back mutations may optionally be made in the framework regions at one or more of the residues to improve CD52-binding affinity of the humanized antibody.

The antibodies of this invention may differ from antibody Ab26 by the addition, deletion or substitution (e.g., conservative substitution) of one or more residues, e.g., differing by up to 1, 2, 3, 4, 5, 6, 7, 8, 9, 10, 11, or 12 residues from the parental sequences.

By way of examples, the present invention includes antibodies having a heavy chain comprising one or more CDRs (e.g., all three CDRs) of SEQ ID NO: 59 and a light chain comprising one or more CDRs (e.g., all three CDRs) of SEQ ID NO: 68; a heavy chain comprising one or more CDRs (e.g., all three CDRs) of SEQ ID NO: 59 and a light chain comprising one or more CDRs (e.g., all three CDRs) of SEQ ID NO: 69; a heavy chain comprising one or more CDRs (e.g., all three CDRs) of SEQ ID NO: 59 and a light chain comprising one or more CDRs (e.g., all three CDRs) of SEQ ID NO: 70; a heavy chain comprising one or more CDRs (e.g., all three CDRs) of SEQ ID NO: 59 and a light chain comprising one or more CDRs (e.g., all three CDRs) of SEQ ID NO: 71; a heavy chain comprising one or more CDRs (e.g., all three CDRs) of SEQ ID NO: 59 and a light chain comprising one or more CDRs (e.g., all three CDRs) of SEQ ID NO: 72; a heavy chain comprising one or more CDRs (e.g., all three CDRs) of SEQ ID NO: 59 and a light chain comprising one or more CDRs (e.g., all three CDRs) of SEQ ID NO: 73; a heavy chain comprising one or more CDRs (e.g., all three CDRs) of SEQ ID NO: 59 and a light chain comprising one or more CDRs (e.g., all three CDRs) of SEQ ID NO: 74; a heavy chain comprising one or more CDRs (e.g., all three CDRs) of SEQ ID NO: 59 and a light chain comprising one or more CDRs (e.g., all three CDRs) of SEQ ID NO: 75; a heavy chain comprising one or more CDRs (e.g., all three CDRs) of SEQ ID NO: 59 and a light chain comprising one or more CDRs (e.g., all three CDRs) of SEQ ID NO: 76; a heavy chain comprising one or more CDRs (e.g., all three CDRs) of SEQ ID NO: 59 and a light chain comprising one or more CDRs (e.g., all three CDRs) of SEQ ID NO: 77; a heavy chain comprising one or more CDRs (e.g., all three CDRs) of SEQ ID NO: 59 and a light chain comprising one or more CDRs (e.g., all three CDRs) of SEQ ID NO: 78; a heavy chain comprising one or more CDRs (e.g., all three CDRs) of SEQ ID NO: 59 and a light chain comprising one or more CDRs (e.g., all three CDRs) of SEQ ID NO: 79; a heavy chain comprising one or more CDRs (e.g., all three CDRs) of SEQ ID NO: 59 and a light chain comprising one or more CDRs (e.g., all three CDRs) of SEQ ID NO: 80; a heavy chain comprising one or more CDRs (e.g., all three CDRs) of SEQ ID NO: 59 and a light chain comprising one or more CDRs (e.g., all three CDRs) of SEQ ID NO: 81; a heavy chain comprising one or more CDRs (e.g., all three CDRs) of SEQ ID NO: 59 and a light chain comprising one or more CDRs (e.g., all three CDRs) of SEQ ID NO: 82; or a heavy chain comprising one or more CDRs (e.g., all three CDRs) of SEQ ID NO: 59 and a light chain comprising one or more CDRs (e.g., all three CDRs) of SEQ ID NO: 83.

In one embodiment, an antibody of the invention has binding specificity for human CD52 and comprises heavy chain (H)-CDR1, H-CDR2, H-CDR3, light chain (L)-CDR1, L-CDR2, and L-CDR3 whose amino acid sequences are: a) SEQ ID NOs: 7, 8, 9, 18, 34, and 35, respectively; b) SEQ ID NOs: 7, 8, 9, 19, 34, and 35, respectively; c) SEQ ID NOs: 7, 8, 9, 20, 34, and 35, respectively; d) SEQ ID NOs: 7, 8, 9, 21, 34, and 35, respectively; e) SEQ ID NOs: 7, 8, 9, 22, 34, and 35, respectively; f) SEQ ID NOs: 7, 8, 9, 23, 34, and 35, respectively; g) SEQ ID NOs: 7, 8, 9, 24, 34, and 35, respectively; h) SEQ ID NOs: 7, 8, 9, 25, 34, and 35, respectively; i) SEQ ID NOs: 7, 8, 9, 26, 34, and 35, respectively; j) SEQ ID NOs: 7, 8, 9, 27, 34, and 35, respectively; k) SEQ ID NOs: 7, 8, 9, 28, 34, and 35, respectively; l) SEQ ID NOs: 7, 8, 9, 29, 34, and 35, respectively; m) SEQ ID NOs: 7, 8, 9, 30, 34, and 35, respectively; n) SEQ ID NOs: 7, 8, 9, 31, 34, and 35, respectively; o) SEQ ID NOs: 7, 8, 9, 32, 34, and 35, respectively; or p) SEQ ID NOs: 7, 8, 9, 33, 34, and 35, respectively.

In some embodiments, an antibody of the invention comprises the L-CDR1 of SEQ ID NO: 86 (KSSQSLLYSNXKTYLN), wherein X is a naturally occurring amino acid selected from D, E, K, R, H, Y, C, N, Q, S, T, A, V, L, I, M, P, F, or W or a non-standard (e.g., unnatural) amino acid.

The invention also relates to an antibody light chain of an antibody described herein. In one embodiment, the antibody light chain comprises an L-CDR1 selected from the group consisting of SEQ ID NOs: 18, 19, 20, 21, 22, 23, 24, 25, 26, 27, 28, 29, 30, 31, 32, and 33. For example, the antibody has L-CDR1, L-CDR2, and L-CDR3 whose amino acid sequences are: a) SEQ ID NOs: 18, 34, and 35, respectively; b) SEQ ID NOs: 19, 34, and 35, respectively; c) SEQ ID NOs: 20, 34, and 35, respectively; d) SEQ ID NOs: 21, 34, and 35, respectively; e) SEQ ID NOs: 22, 34, and 35, respectively; f) SEQ ID NOs: 23, 34, and 35, respectively; g) SEQ ID NOs: 24, 34, and 35, respectively; h) SEQ ID NOs: 25, 34, and 35, respectively; i) SEQ ID NOs: 26, 34, and 35, respectively; j) SEQ ID NOs: 27, 34, and 35, respectively; k) SEQ ID NOs: 28, 34, and 35, respectively; l) SEQ ID NOs: 29, 34, and 35, respectively; m) SEQ ID NOs: 30, 34, and 35, respectively; n) SEQ ID NOs: 31, 34, and 35, respectively; o) SEQ ID NOs: 32, 34, and 35, respectively; or p) SEQ ID NOs: 33, 34, and 35, respectively.

Table 2 lists the sequence identifiers (SEQ ID NOs) of the amino acid sequences of the full-length heavy and light chains and variable domains of antibodies that are specifically illustrated herein, as well as the nucleotide sequences encoding the heavy and light chains and variable domains.

TABLE 2

| | SEQ ID NOs of Anti-CD52 Antibodies | | | | | | | |
|---|---|---|---|---|---|---|---|---|
| | FULL LENGTH | | | | VARIABLE DOMAIN | | | |
| | Heavy | | Light | | Heavy | | Light | |
| Antibody | DNA | Amino Acid | DNA | Amino Acid | DNA | Amino Acid | DNA | Amino Acid |
| Ab1 | 5 | 3 | 112 | 36 | 84 | 59 | 88 | 61 |
| Ab2 | 5 | 3 | 113 | 37 | 84 | 59 | 89 | 62 |
| Ab3 | 5 | 3 | 114 | 38 | 84 | 59 | 90 | 63 |
| Ab4 | 5 | 3 | 115 | 39 | 84 | 59 | 91 | 64 |
| Ab5 | 5 | 3 | 116 | 40 | 84 | 59 | 92 | 65 |
| Ab6 | 5 | 3 | 117 | 41 | 84 | 59 | 93 | 66 |
| Ab7 | 5 | 3 | 118 | 42 | 84 | 59 | 94 | 67 |
| Ab10 | 5 | 3 | 119 | 43 | 84 | 59 | 95 | 68 |
| Ab11 | 5 | 3 | 120 | 44 | 84 | 59 | 96 | 69 |
| Ab12 | 5 | 3 | 121 | 45 | 84 | 59 | 97 | 70 |
| Ab13 | 5 | 3 | 122 | 46 | 84 | 59 | 98 | 71 |
| Ab14 | 5 | 3 | 123 | 47 | 84 | 59 | 99 | 72 |
| Ab15 | 5 | 3 | 124 | 48 | 84 | 59 | 100 | 73 |
| Ab16 | 5 | 3 | 125 | 49 | 84 | 59 | 101 | 74 |
| Ab17 | 5 | 3 | 126 | 50 | 84 | 59 | 102 | 75 |
| Ab18 | 5 | 3 | 127 | 51 | 84 | 59 | 103 | 76 |
| Ab19 | 5 | 3 | 128 | 52 | 84 | 59 | 104 | 77 |
| Ab20 | 5 | 3 | 129 | 53 | 84 | 59 | 105 | 78 |
| Ab21 | 5 | 3 | 130 | 54 | 84 | 59 | 106 | 79 |
| Ab22 | 5 | 3 | 131 | 55 | 84 | 59 | 107 | 80 |
| Ab23 | 5 | 3 | 132 | 56 | 84 | 59 | 108 | 81 |
| Ab24 | 5 | 3 | 133 | 57 | 84 | 59 | 109 | 82 |
| Ab25 | 5 | 3 | 134 | 58 | 84 | 59 | 110 | 83 |

In one embodiment, an antibody of this invention comprises a light chain comprising a variable domain ($V_L$) sequence of SEQ ID NO: 68, 69, 70, 71, 72, 73, 74, 75, 76, 77, 78, 79, 80, 81, 82, or 83. In another embodiment, the antibody comprises a light chain whose amino acid sequence comprises or consists of SEQ ID NO: 43, 44, 45, 46, 47, 48, 49, 50, 51, 52, 53, 54, 55, 56, 57, or 58.

In some embodiments, an antibody of this invention comprises a $V_H$ and a $V_L$ whose amino acid sequences comprise or consist of a) SEQ ID NOs: 59 and 68, respectively; b) SEQ ID NOs: 59 and 69, respectively; c) SEQ ID NOs: 59 and 70, respectively; d) SEQ ID NOs: 59 and 71, respectively; e) SEQ ID NOs: 59 and 72, respectively; f) SEQ ID NOs: 59 and 73, respectively; g) SEQ ID NOs: 59 and 74, respectively; h) SEQ ID NOs: 59 and 75, respectively; i) SEQ ID NOs: 59 and 76, respectively; j) SEQ ID NOs: 59 and 77, respectively; k) SEQ ID NOs: 59 and 78, respectively; l) SEQ ID NOs: 59 and 79, respectively; m) SEQ ID NOs: 59 and 80, respectively; n) SEQ ID NOs: 59 and 81, respectively; o) SEQ ID NOs: 59 and 82, respectively; or p) SEQ ID NOs: 59 and 83, respectively.

In one embodiment, an antibody of this invention comprises a heavy chain (HC) and a light chain (LC) whose amino acid sequences comprise or consist of a) SEQ ID NOs: 3 and 43, respectively; b) SEQ ID NOs: 3 and 44, respectively; c) SEQ ID NOs: 3 and 45, respectively; d) SEQ ID NOs: 3 and 46, respectively; e) SEQ ID NOs: 3 and 47, respectively; f) SEQ ID NOs: 3 and 48, respectively; g) SEQ ID NOs: 3 and 49, respectively; h) SEQ ID NOs: 3 and 50, respectively; i) SEQ ID NOs: 3 and 51, respectively; j) SEQ ID NOs: 3 and 52, respectively; k) SEQ ID NOs: 3 and 53, respectively; l) SEQ ID NOs: 3 and 54, respectively; m) SEQ ID NOs: 3 and 55, respectively; n) SEQ ID NOs: 3 and 56, respectively; o) SEQ ID NOs: 3 and 57, respectively; or p) SEQ ID NOs: 3 and 58, respectively; each sequence with or without the signal sequence, if present.

Also provided herein are portions of whole antibodies, such as light chains or heavy chains of the antibodies, or a portion of the light and/or heavy chains. Portions of whole antibodies include antigen-binding portions of the whole antibodies. The terms of "antigen-binding fragment" and "antigen-binding portion" are used interchangeably herein. Antibody-binding fragments of antibodies include, for example, single chain antibodies, Fv fragments, Fab fragments, Fab' fragments, F(ab')$_2$ fragments, Fd fragments, single chain Fv molecules (scFv), scFv-Fc fusions, bispecific single chain Fv dimers, minibodies, diabodies, triabodies, tetrabodies, domain-deleted antibodies and single domain antibodies (dAbs). See e.g., Nature Biotechnology 22(9):1161-1165 (2004)). Also within the invention are antigen-binding molecules comprising a V$_H$ and/or a V$_L$. In the case of a V$_H$, the molecule may also comprise one or more of the CH1, hinge, CH2 and CH3 regions.

Antibody portion or fragments can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the CH$_1$ domain and hinge region of the heavy chain. An antigen-binding fragment retains the binding specificity of its parent antibody. Preferred antigen-binding fragments have binding specificity for a wild-type human CD52. Nucleic acid (e.g., DNA) sequences coding for humanized variable regions can be constructed using PCR mutagenesis methods to alter existing DNA sequences (See e.g., Kamman, M., et al., Nucl. Acids Res. 17:5404 (1989)). PCR primers coding for the new CDRs can be hybridized to a DNA template of a previously humanized variable region which is based on the same, or a very similar, human variable region (Sato, K., et al., Cancer Research 53:851-856 (1993)). If a similar DNA sequence is not available for use as a template, a nucleic acid comprising a sequence encoding a variable region sequence can be constructed from synthetic oligonucleotides (See e.g., Kolbinger, F., Protein Engineering 8:971-980 (1993)). A sequence encoding a signal peptide can also be incorporated into the nucleic acid (e.g., on synthesis, upon insertion into a vector). If a signal peptide sequence is unavailable (e.g., not typically present), a signal peptide sequence from another antibody can be used (See, e.g., Kettleborough, C. A., Protein Engineering 4:773-783 (1991)). Using these methods, methods described herein or other suitable methods, variants can readily be produced. Unless otherwise indicated, discussions of the making and using of the antibodies of this invention are applicable to the antigen-binding fragments of these antibodies.

The antibodies of the present invention can be of any isotype or subtype, including IgG (e.g., IgG1, IgG2, IgG3, or IgG4), IgM, IgA (e.g., IgA1 and IgA2), IgD and IgE. The antibodies may comprise a light chain derived from either human kappa or lambda light chain.

In another aspect, the invention provides a variant of an antibody or portion thereof as described herein, wherein said variant binds to human CD52 specifically but differs from the reference antibody or portion thereof by 1, 2, 3, 4, 5, 6, 7, 8, 9 or 10 amino acid substitutions (for example, in a CDR region, a FR region, or a constant domain). For example, the variant antibody is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the reference antibody in the heavy chain, the heavy chain variable domain, the light chain, or the light chain variable domain.

Sequence similarity or identity for polypeptides is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., J. Mol. Biol. 215:403-410 (1990); Altschul et al., Nucleic Acids Res. 25:3389-402 (1997); herein incorporated by reference.

As used herein, "amino acids" are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

According to the invention, one type of amino acid substitution that may be made is to change one or more cysteines in the antibody, which may be chemically reactive, to another residue, such as, without limitation, alanine or serine. In one embodiment, there is a substitution of a non-canonical cysteine. The substitution can be made in a CDR or framework region of a variable domain or in the constant domain of an antibody. In some embodiments, the cysteine is canonical. Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another aspect of the invention, the antibody may be deimmunized to reduce its immunogenicity using the techniques described in, e.g., International Patent Application Publications WO 98/52976 and WO 00/34317.

Another type of amino acid substitution that may be made in one of the variants according to the invention is a conservative amino acid substitution. A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g., Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., Science 256:1443-45 (1992). A "moderately conservative" replacement is any change having a nonnegative value in the PAM250 log-likelihood matrix.

In certain embodiments, amino acid substitutions to an antibody or antigen-binding portion of the invention are those which: (1) reduce susceptibility to proteolysis, (2) reduce susceptibility to oxidation, (3) alter binding affinity for forming protein complexes, for example, to enhance ADCC and CDC activity of the antibody, (4) confer or modify other physicochemical or functional properties of such analogs, but still retain specific binding to human CD52, (5) remove C-terminal lysine, and (6) add or remove glycosylation sites. In some embodiments, the C-terminal lysine of the heavy chain of the anti-CD52 antibody of the invention is not present (Lewis et al., Anal. Chem, 66(5): 585-595 (1994)).

In an aspect, the invention provides a new and novel polypeptide that is the light (or heavy) chain of an antibody of this invention, or that is a variable domain-containing portion of the light (or heavy) chain. Such a polypeptide is useful because it can partner with an opposite heavy (or light) antibody chain to form a CD52-binding molecule. Once an initial $V_L$ or $V_H$ domain of an antibody of the invention is selected, "mix and match" experiments may be performed, in which different pairs comprising the initially selected $V_L$ or $V_H$ segment are screened for CD52 binding to select preferred $V_L/V_H$ pair combinations. One defined variable domain sequence may be used to engineer functional antibodies to CD52 by screening variable domain libraries for a repertoire of functional partner variable domains. See, for example, Clackson et al., Nature, 352:624-628 (1991); Portolano et al., J. Immunol., 150:880-887 (1993); Beiboer et al., J. Mol. Biol., 296:833-849 (2000); Klimka et al., British Journal of Cancer, 83:252-260 (2000).

For diagnostic or assay purposes (e.g., imaging to allow, for example, monitoring of therapies), the antibody (e.g., antigen-binding fragment thereof) can comprise a detectable label. Suitable detectable labels and methods for labeling an antibody or antigen-binding fragment thereof are well known in the art. Suitable detectable labels include, for example, a radioisotope (e.g., as Indium-111, Technetium-99m or Iodine-131), positron emitting labels (e.g., Fluorine-19), paramagnetic ions (e.g., Gadlinium (III), Manganese (II)), an epitope label (tag), an affinity label (e.g., biotin, avidin), a spin label, an enzyme, a fluorescent group or a chemiluminescent group. When labels are not employed, complex formation (e.g., between humanized antibody and human CD52) can be determined by surface plasmon resonance, ELISA, FACS, or other suitable methods.

Anti-CD52 antibodies and antigen-binding fragments used in the invention also may be conjugated, via, for example, chemical reactions or genetic modifications, to other moieties (e.g., pegylation moieties) that improve the antibodies' pharmacokinetics such as half-life. In some embodiments, the anti-CD52 antibodies and antigen-binding fragments used in this invention can be linked to a suitable cytokine via, e.g., chemical conjugation or genetic modifications (e.g., appending the coding sequence of the cytokine in frame to an antibody coding sequence, thereby creating an antibody:cytokine fusion protein).

The invention also relates to immunoconjugates in which the antibody or antigen-binding fragment of the invention is coupled to another therapeutic agent, such as a bioactive compound (e.g., cytokines, superantigens, cytotoxic agents and toxins). For example, the antibody or fragment can be coupled to a molecule of plant or bacterial origin (or derivative thereof), an interleukin-2 antibody, or diptheria toxin antibodies.

Stability of the Present Antibodies

The antibodies of the invention are stable in storage. The antibodies of the invention may have increased stability compared to the stability demonstrated by Ab26. The stability may be shown by measuring the binding affinity of an antibody to CD52 after a period in storage. To demonstrate stability, the antibody may be incubated at 37° C. or 45° C. and at pH 7.0, 7.5, or 8.0. The antibody may be incubated in buffer containing 10 mM succinate, 10 mM histidine, and 10 mM sodium phosphate, pH 7.5. The increased stability may extend for at least 1 week, for at least 2 weeks, for at least 3 weeks, for at least 4 weeks, for at least 5 weeks, for at least 6 weeks, for at least 7 weeks, for at least 8 weeks, for at least 9 weeks, or for at least 10 weeks.

Nucleic Acids and Recombinant Vectors

The present invention also relates to isolated and/or recombinant (including, e.g., essentially pure) nucleic acid molecules comprising sequences that encode an antibody, antigen-binding fragment, light chain, heavy chain, or variable domain of the present invention.

Nucleic acids referred to herein as "isolated" or "purified" are nucleic acids which have been separated away from the nucleic acids of the genomic DNA or cellular RNA of their source of origin (e.g., as they exist in cells or in a mixture of nucleic acids such as a library), and include nucleic acids obtained by methods described herein or other suitable methods, including essentially pure nucleic acids, nucleic acids produced by chemical synthesis, by combinations of biological and chemical methods, and recombinant nucleic acids which are isolated (See e.g., Daugherty, B. L. et al., Nucleic Acids Res., 19(9): 2471-2476 (1991); Lewis, A. P. and J. S. Crowe, Gene, 101: 297-302 (1991)).

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

The present invention also relates more specifically to isolated and/or recombinant nucleic acids comprising a nucleotide sequence which encodes an antibody that has binding specificity for human CD52, or a heavy or light chain, or a heavy chain variable region, or light chain variable region of said antibody.

In some embodiments, the nucleic acid molecule comprises a nucleotide sequence selected from the group consisting of SEQ ID NOs: 95, 96, 97, 98, 99, 100, 101, 102, 103, 104, 105, 106, 107, 108, 109, or 110, which encodes the $V_L$ amino acid sequence of an anti-CD52 antibody. In some embodiments, the nucleic acid molecule encodes a $V_L$ amino acid sequence of SEQ ID NO: 68, 69, 70, 71, 72, 73, 74, 75, 76, 77, 78, 79, 80, 81, 82, or 83. In some embodiments, the nucleic acid molecule encodes a $V_L$ amino acid sequence that is at least 70%, 75%, 80%, 85%, 90%, 95%, 96%, 97%, 98% or 99% identical to the $V_L$ amino acid sequence of a reference anti-CD52 antibody (for example, Ab26). The nucleotide sequence encoding the $V_L$ amino acid sequence of Ab26 may be SEQ ID NO: 85. In some embodiments, the nucleic acid molecule encodes a $V_L$ amino acid sequence comprising 1, 2, 3, 4, 5, 6, 7, 8, 9, 10, 11, or 12 mutations compared to the $V_L$ amino acid sequence of a reference anti-CD52 antibody (for example, Ab26). The mutations may be in CDRs or in FRs.

In some embodiments, the nucleic acid molecule comprises a nucleotide sequence selected from the group consisting of SEQ ID NOs: 119, 120, 121, 122, 123, 124, 125, 126, 127, 128, 129, 130, 131, 132, 133, or 134, which encodes the light chain amino acid sequence of an anti-CD52 antibody, either with or without a signal sequence. In some embodiments, the nucleic acid molecule encodes a light chain amino acid sequence of SEQ ID NO: 43, 44, 45, 46, 47, 48, 49, 50, 51, 52, 53, 54, 55, 56, 57, or 58, either with or without a signal sequence. In some embodiments, the nucleic acid molecule encodes a light chain amino acid sequence that is at least 70%, 75%, 80%, 85%, 90%, 95%, 96%, 97%, 98% or 99% identical to the light chain amino acid sequence of a reference anti-CD52 antibody (for example, Ab26). The nucleotide sequence encoding the light chain amino acid sequence of Ab26 may be SEQ ID NO: 6, with or without the signal sequence. In some embodiments, the nucleic acid molecule encodes a light chain amino acid sequence comprising 1, 2, 3, 4, 5, 6, 7, 8, 9, 10, 11, or 12 mutations compared to the light chain amino acid sequence of a reference anti-CD52 antibody (for example, Ab26). The mutations may be in CDRs, in FRs, or in constant domains.

In some embodiments, the nucleic acid molecule comprises a nucleotide sequence that encodes the $V_H$ amino acid sequence of an anti-CD52 antibody. For example, this nucleotide sequence may be SEQ ID NO: 84. In some embodiments, the nucleic acid molecule encodes a $V_H$ amino acid sequence that is at least 70%, 75%, 80%, 85%, 90%, 95%, 96%, 97%, 98% or 99% identical to the $V_H$ amino acid sequence of a reference anti-CD52 antibody (for example, Ab26). The nucleotide sequence encoding the $V_H$ amino acid sequence of Ab26 may be SEQ ID NO: 84. In some embodiments, the nucleic acid molecule encodes a $V_H$ amino acid sequence comprising 1, 2, 3, 4, 5, 6, 7, 8, 9, 10 or 11 mutations compared to the $V_H$ amino acid sequence of a reference anti-CD52 antibody (for example, Ab26). The mutations may be in CDRs or in FRs.

In some embodiments, the nucleic acid molecule comprises a nucleotide sequence that encodes the heavy chain amino acid sequence of an anti-CD52 antibody, either with or without a signal sequence. For example, this nucleotide sequence may be SEQ ID NO: 5, with or without the signal sequence. In some embodiments, the nucleic acid molecule encodes a heavy chain amino acid sequence that is at least 70%, 75%, 80%, 85%, 90%, 95%, 96%, 97%, 98% or 99% identical to the heavy chain amino acid sequence of a reference anti-CD52 antibody (for example, Ab26). The nucleotide sequence encoding the heavy chain amino acid sequence of Ab26 may be SEQ ID NO: 5, with or without the signal sequence. In some embodiments, the nucleic acid molecule encodes a heavy chain amino acid sequence comprising 1, 2, 3, 4, 5, 6, 7, 8, 9, 10 or 11 mutations compared to the heavy chain amino acid sequence of a reference anti-CD52 antibody (for example, Ab26). The mutations may be in CDRs, in FRs, or in constant domains.

Nucleic acids of the present invention can be used to produce humanized antibodies having binding specificity for human CD52. For example, a nucleic acid (e.g., DNA (such as cDNA), or RNA) or one or more nucleic acids encoding a humanized antibody of the present invention can be incorporated into a suitable construct (e.g., a recombinant vector) for further manipulation of sequences or for production of the encoded antibodies in suitable host cells.

Constructs or vectors (e.g., expression vectors) suitable for the expression of a humanized antibody having binding specificity for human CD52 are also provided. A variety of vectors are available, including vectors which are maintained in single copy or multiple copies in a host cell, or which become integrated into the host cell's chromosome(s). The constructs or vectors can be introduced into a suitable host cell, and cells which express a humanized antibody of the present invention, can be produced and maintained in culture. A single vector or multiple vectors can be used for the expression of a humanized antibody having binding specificity for human CD52.

Suitable expression vectors, for example mammalian cell expression vectors, can also contain a number of components, including, but not limited to one or more of the following: an origin of replication; a selectable marker gene; one or more expression control elements, such as a transcriptional control element (e.g., a promoter, an enhancer, a terminator), and/or one or more translation signals; a signal sequence or leader sequence for membrane targeting or secretion. In a construct or vector, a signal peptide sequence can be provided by the construct or vector or other source. For example, the transcriptional and/or translational signals of an antibody can be used to direct expression.

A promoter can be provided for expression in a suitable host cell. Promoters can be constitutive or inducible. For example, a promoter can be operably linked to a nucleic acid encoding a humanized antibody or antibody chain, such that it directs expression of the encoded polypeptide. A variety of suitable promoters for prokaryotic (e.g., lac, tac, T3, T7 promoters for *E. coli*) and eukaryotic (e.g., yeast alcohol dehydrogenase (ADH1), SV40, CMV) hosts are available. Those of skill in the art will be able to select the appropriate promoter for expressing an anti-CD52 antibody or portion thereof of the invention.

In addition, the vectors (e.g., expression vectors) typically comprise a selectable marker for selection of host cells carrying the vector, and, in the case of a replicable vector, an origin of replication. Genes encoding products which confer antibiotic or drug resistance are common selectable markers and may be used in prokaryotic (e.g., β-lactamase gene (ampicillin resistance), Tet gene (tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

The invention thus relates to isolated nucleic acid molecules that encode the humanized antibody, humanized light chain, humanized heavy chain of this invention. The invention also relates to isolated nucleic acid molecules that encode an antigen-binding portion of the antibodies and their chains. Polypeptide sequences encoded by the nucleic acids of this invention are described above and in the following Examples.

In some embodiments, a nucleic acid or vector of this invention encodes a heavy chain (or an antigen-binding portion thereof) or a light chain (or an antigen-binding portion thereof) of this invention. In other embodiments, a nucleic acid or vector of this invention encodes both a heavy and a light chain (or antigen-binding portions thereof) of this invention. A host cell containing both the heavy chain-encoding nucleic acid and the light chain-encoding nucleic acid, or one nucleic acid encoding both the heavy and light chains, can be used to make an antibody comprising the heavy and light chain (or an antigen-binding portion of the antibody). The heavy chain-encoding nucleic acid and the light chain-encoding nucleic acid can be placed on separate expression vectors. They can also be placed on a single expression vector under the same or different expression control. See, e.g., Cabilly U.S. Pat. No. 6,331,415; Fang U.S. Pat. No. 7,662,623.

Method of Producing Antibodies Having Specificity for Human CD52

Another aspect of the invention relates to a method of making an anti-human CD52 antibody of this invention. The antibody of this invention can be produced, for example, by the expression of one or more recombinant nucleic acids encoding the antibody in a suitable host cell. The host cell can be produced using any suitable method. For example, the expression constructs (e.g., the one or more vectors, e.g., a mammalian cell expression vector) described herein can be introduced into a suitable host cell, and the resulting cell can be maintained (e.g., in culture, in an animal, in a plant) under conditions suitable for expression of the construct(s) or vector(s). Suitable host cells can be prokaryotic, including bacterial cells such as *E. coli* (e.g., strain DH5α™ (Invitrogen, Carlsbad, Calif.)), *B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells (WO 94/26087 (O'Connor), TN5B1-4 (HIGH 5) insect cells (Invitrogen), mammals (e.g., COS cells, such as COS-1 (ATCC Accession No. CRL-1650) and COS-7 (ATCC Accession No. CRL-1651), CHO (e.g., ATCC Accession No. CRL-9096), CHO DG44 (Urlaub, G. and Chasin, L A., Proc. Natl. Acad. Sci. USA, 77(7):4216-4220 (1980)), 293 (ATCC Accession No. CRL-1573), HeLa (ATCC Accession No. CCL-2), CV1 (ATCC Accession No. CCL-70), WOP (Dailey, L., et al., J. Virol., 54:739-749 (1985)), 3T3, 293T (Pear, W. S., et al., Proc. Natl. Acad. Sci. U.S.A., 90:8392-8396 (1993)), NS0 cells, SP2/0 cells, HuT 78 cells and the like)), or plants (e.g., tobacco, lemna (duckweed), and algae). (See, for example, Ausubel, F. M. et al., eds. Current Protocols in Molecular Biology, Greene Publishing Associates and John Wiley & Sons Inc. (1993)). In some embodiments, the host cell is not part of a multicellular organism (e.g., plant or animal), e.g., it is an isolated host cell or is part of a cell culture.

The present invention also relates to cells comprising a nucleic acid, e.g., a vector, of the invention (e.g., an expression vector). For example, a nucleic acid (i.e., one or more nucleic acids) encoding the heavy and light chains of a humanized antibody, said antibody having binding specificity for human CD52, or a construct (i.e., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded protein (e.g., humanized antibody, mouse antibody, chimeric antibody) can be isolated, for example, from the host cells, culture medium, or milk. This process encompasses expression in a host cell (e.g., a mammary gland cell) of a transgenic animal or plant (e.g., tobacco) (See e.g., WO 92/03918).

Fusion proteins can be produced in which an antibody portion (e.g., an antigen-binding fragment; antibody chain) is linked to a non-antibody moiety (i.e., a moiety which does not occur in antibodies as found in nature) in an N-terminal location, C-terminal location or internal to the fusion protein. For example, some embodiments can be produced by the insertion of a nucleic acid encoding an antibody sequence(s) into a suitable expression vector, such as a pET vector (e.g., pET-15b, Novagen), a phage vector (e.g., pCANTAB 5 E, Pharmacia), or other vector (e.g., pRIT2T Protein A fusion vector, Pharmacia). The resulting construct can be introduced into a suitable host cell for expression. Upon expression, some fusion proteins can be isolated or purified from a cell lysate by means of a suitable affinity matrix (See, e.g., Current Protocols in Molecular Biology (Ausubel, F. M. et al., Eds., Vol. 2, Suppl. 26, pp. 16.4.1-16.7.8 (1991)).

The invention relates to a host cell that comprises recombinant nucleic acid(s) encoding an antibody provided herein (e.g., an antibody, a light chain or a heavy chain, a light chain variable region or a heavy chain variable regions). The invention also relates to a host cell that comprises recombinant nucleic acid(s) encoding an antigen-binding portion of the antibody or their chains. In some embodiments, the host cell comprises a recombinant vector (e.g., expression vector, mammalian cell expression vector) of the invention as referred to herein.

The invention also relates to a method of preparing an antibody or an antibody polypeptide chain of this invention. In one embodiment, the method comprises maintaining a host cell of the invention as described herein (e.g., a host cell that contains one or more isolated nucleic acids that encode the antibody or polypeptide chain (e.g., a light chain and a heavy chain, a light chain only, or a heavy chain only, of the invention) under conditions appropriate for expression of the antibody or polypeptide chain. For example a host cell can be cultured on a substrate or in suspension. In some embodiments, the method further comprises the step of purifying or isolating the antibody or polypeptide chain.

Selections can be performed using CD52 coupled to DYNABEADS M-270 amine (Dynal) according to the manufacturer's recommendations. Alternatively, selections using biotinylated CD52 can be prepared using the primary amine specific reagent succinimidyl-6-(biotinamido) hexanoate following the manufacturer's instructions (EZ link NHS LC Biotin, Pierce).

Outputs from selections can be tested as periplasmic preparations in high throughput screens based on competition assays which measure the ability of the scFvs or IgGs to compete for binding to CD52.

Samples that are able to compete in the high throughput screens may be subjected to DNA sequencing as described in Vaughan et al. (1996) and Osburn et al. (1996). Clones would then be expressed and purified as scFvs or IgGs and assessed for their ability to bind CD52, neutralize CD52 or a combination thereof, e.g., using assays such as antibody-dependent cell mediated cytotoxicity (ADCC) assay and complement dependent cytotoxicity (CDC) assay. Purified scFv preparations can then be prepared as described in Example 3 of WO 01/66754. Protein concentrations of purified scFv or IgG preparations may be determined using the BCA method (Pierce). Similar approaches can be used to screen for an optimal partner (the opposite chain) of a fixed antibody heavy or light chain (or $V_H$ or $V_L$).

The antibodies of the invention can be in a purified or isolated form (e.g., having been separated away from molecules (e.g., peptides) of their source of origin (e.g., the supernatant of cells; in a mixture such as in a mixture of antibodies in a library), and include antibodies obtained by methods described herein or other suitable methods. Isolated antibodies include substantially pure (essentially pure) antibodies, and antibodies produced by chemical synthesis, recombinant techniques and a combination thereof.

Antibodies Containing a Toxin Moiety or Toxin

The invention also relates to antibodies that comprise a toxin moiety or toxin. Suitable toxin moieties comprise a toxin (e.g., surface active toxin, cytotoxin). The toxin moiety or toxin can be linked or conjugated to the antibody using any suitable method. For example, the toxin moiety or toxin can be covalently bonded to the antibody directly or through a suitable linker. Suitable linkers can include noncleavable or cleavable linkers, for example, pH cleavable linkers or linkers that comprise a cleavage site for a cellular enzyme. Such cleavable linkers can be used to prepare an antibody that can release a toxin moiety or toxin after the antibody is internalized.

A variety of methods for linking or conjugating a toxin moiety or toxin to an antibody can be used. The particular method selected will depend on the toxin moiety or toxin and antibody to be linked or conjugated. If desired, linkers that contain terminal functional groups can be used to link the antibody and toxin moiety or toxin. Generally, conjugation is accomplished by reacting toxin moiety or toxin that contains a reactive functional group (or is modified to contain a reactive functional group) with a linker or directly with an antibody. Covalent bonds are formed by reacting a toxin moiety or toxin that contains (or is modified to contain) a chemical moiety or functional group that can, under appropriate conditions, react with a second chemical group thereby forming a covalent bond. If desired, a suitable reactive chemical group can be added to an antibody or to a linker using any suitable method. (See, e.g., Hermanson, G. T., Bioconjugate Techniques, Academic Press: San Diego, Calif. (1996).) Many suitable reactive chemical group combinations are known in the art, for example an amine group can react with an electrophilic group such as tosylate, mesylate, halo, N-hydroxysuccinimidyl ester (NHS), and the like. Thiols can react with maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (See for example, Hermanson, G. T., Bioconjugate Techniques, Academic Press: San Diego, Calif. (1996)).

Suitable toxin moieties and toxins include, for example, a maytansinoid, a taxane, a calicheamicin, a duocarmycin, or derivatives thereof. The maytansinoid can be, for example, maytansinol or a maytansinol analogue. Examples of maytansinol analogs include those having a modified aromatic ring and those having modifications at other positions. Maytansinol and maytansinol analogs are described, for example, in U.S. Pat. Nos. 5,208,020 and 6,333,410, the contents of which are incorporated herein by reference. Maytansinol can be coupled to antibodies and antibody fragments using, e.g., an N-succinimidyl 3-(2-pyridyldithio) proprionate (also known as N-succinimidyl 4-(2-pyridyldithio)pentanoate (or SPP)), 4-succinimidyl-oxycarbonyl-a-(2-pyridyldithio)-toluene (SMPT), N-succinimidyl-3-(2-pyridyldithio)butyrate (SDPB), 2 iminothiolane, or S-acetylsuccinic anhydride. The taxane can be, for example, a taxol, taxotere, or novel taxane (See, e.g., WO 01/38318). The calicheamicin can be, for example, a bromo-complex calicheamicin, an iodo-complex calicheamicin, or analogs and mimics thereof. Bromo-complex calicheamicins include I1-BR, I2-BR, I3-BR, I4-BR, J1-BR, J2-BR and K1-BR. Iodo-complex calicheamicins include I1-I, I2-I, I3-I, J1-I, J2-I, L1-I and K1-BR. Calicheamicin and mutants, analogs and mimics thereof are described, for example, in U.S. Pat. Nos. 4,970,198, 5,264,586, 5,550,246, 5,712,374, and 5,714,586, the contents of each of which are incorporated herein by reference. Duocarmycin analogs are described, for example, in U.S. Pat. Nos. 5,070,092, 5,187,186, 5,641,780, 5,641,780, 4,923,990, and 5,101,038, the contents of each of which are incorporated herein by reference.

Examples of other toxins include, but are not limited to antimetabolites, alkylating agents, anthracyclines, antibiotics, and anti-mitotic agents. The toxin can also be a surface active toxin, such as a toxin that is a free radical generator, or radionuclide containing moiety. The toxin can be a protein, polypeptide or peptide, e.g., from bacterial sources or plant protein.

Antisense compounds of nucleic acids designed to bind, disable, promote degradation or prevent the production of the mRNA responsible for generating a particular target protein can also be used as a toxin. Antisense compounds include antisense RNA or DNA, single or double stranded, oligonucleotides, or their analogs, which can hybridize specifically to individual mRNA species and prevent transcription and/or RNA processing of the mRNA species and/or translation of the encoded polypeptide and thereby effect a reduction in the amount of the respective encoded polypeptide. Ching, et al., Proc. Natl. Acad. Sci. U.S.A. 86: 10006-10010 (1989); Broder, et al., Ann. Int. Med. 113: 604-618 (1990); Loreau, et al., FEBS Letters 274: 53-56 (1990).

Toxins can also be photoactive agents. Suitable photoactive agents include porphyrin-based materials such as porfimer sodium, the green porphyrins, chlorin E6, hematoporphyrin derivative itself, phthalocyanines, etiopurpurins, texaphrin, and the like.

The toxin can be an antibody or antibody fragment that binds an intracellular target. Such antibodies or antibody fragments can be directed to defined subcellular compartments or targets.

Therapeutic Methods and Compositions

A pharmaceutical composition comprises a therapeutically-effective amount of one or more antibody and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are well known in the art. See, e.g., Remington (2005), THE SCIENCE AND PRACTICE OF PHARMACY, A. Gennaro, et al., eds., 21st ed., Mack Publishing Co. The pharmaceutical composition further may comprise an immuno-suppressive/immunomodulatory and/or anti-inflammatory agent. A method of treating an immune disease in a patient in need of such treatment may comprise administering to the patient a therapeutically effective amount of the pharmaceutical composition. Antagonizing CD40-mediated T cell activation could inhibit undesired T cell responses occurring during autoimmunity, transplant rejection, or allergic responses, for example. Inhibiting CD40-mediated T cell activation could moderate the progression and/or severity of these diseases.

As used herein, a "patient" means an animal, e.g. mammal, including humans. The patient may be diagnosed with an immune disease or cancer. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, inflammation, allergy, autoimmune disease, or graft-related disease. The autoimmune disease may be selected from the group consisting of systemic lupus erythematosus, multiple sclerosis, rheumatoid arthritis, diabetes, psoriasis, scleroderma, atherosclerosis, inflammatory bowel disease, and ulcerative colitis.

The antibodies of this invention are useful in immunosuppression and immuno-ablation. The antibodies target CD52-expressing cells (e.g., T and B cells) and reduce (or "deplete" as used herein) their population in a subject in need thereof. Lymphocyte depletion may be useful in treating a variety of diseases and conditions such as inflammation, autoimmune diseases, and cancer (e.g., lymphocyte (either B or T cell) malignancy). See, e.g., Reiff, A., Hematology, 10(2):79-93 (2005). Examples of diseases and conditions that can be treated with the antibodies or antigen-binding portions of this invention include, without limitation, multiple sclerosis, lupus, rheumatoid arthritis, graft versus host disease (GVHD), inflammatory bowel disease, vasculitis, Behcet's disease, Wegener's granulomatosis, Sjogren's syndrome, uveitis, psoriasis, scleroderma, polymyositis, type I (autoimmune-based) diabetes, autoimmune cytopenias (e.g., autoimmune neutropenia, transfusion-dependent refractory PRCA, leukemia and lymphoma such as non-Hodgkin's lymphoma with bulky disease and B-cell chronic lymphocytic leukemia (CLL). The antibody also can be administered prophylactically to prevent onset of inflammation, or relapse of an autoimmune disease or cancer. For example, the antibody of this invention can be administered as part of a conditioning regimen to prepare a patient for a transplantation (e.g., a stem cell transplant, an infusion of autologous of allogeneic T cells, or a solid organ transplant). In some embodiments, the antibodies and antigen-binding portions of the invention are used to manufacture medicaments for the treatment of an immune disease or cancer.

Any suitable method or route can be used to administer the antibody polypeptide or the pharmaceutical composition. Routes of administration include, for example, parenteral (e.g., intravenous, intraarterial, intramuscular, intrathecal, intraperitoneal, subcutaneous injection), oral (e.g., dietary), locally, topical, inhalation (e.g., intrabronchial, intranasal or oral inhalation, intranasal drops), or rectal, depending on the disease or condition to be treated. A therapeutically effective dose of administered antibody polypeptide(s) depends on numerous factors, including, for example, the type and severity of the immune disease being treated, the use of combination therapy, the route of administration of the antibody polypeptide(s) or pharmaceutical composition, and the weight of the patient. A non-limiting range for a therapeutically effective amount of an antibody is 0.1-20 mg/kg, and in an aspect, 1-10 mg/kg, relative to the body weight of the patient. The dose of antibody polypeptide(s) can be further guided by the amount of antibody polypeptide(s) required for CD52 antagonism in in vitro and/or in vivo models of disease states.

The antibody of this invention can be administered in a single unit dose or multiple doses at any time point deemed appropriate by a health care provider. The dosage can be determined by methods known in the art and can be dependent, for example, upon the individual's age, sensitivity, tolerance and overall well-being. The antibody or portion can be administered in an infusion over a period of several hours, e.g., 3, 4, 5, or 6 hours. The antibody or portion can be administered in various regimens as appropriate, e.g., on two, three, four, five, or six consecutive days, in one or more cycles, separated by 3 or more months, e.g., 12 or 24 months. The total dose of the anti-CD52 antibody administered in any cycle may be 10-60 mg. In one embodiment, the antibodies or portions of the invention are administered to a patient using the same dosing regimens as Campath-1H®.

Antibodies of this invention can be administered to an individual (e.g., a human) alone or in conjunction with another agent (e.g., an immunosuppressant) in a combination therapy. The antibody can be administered before, along with or subsequent to administration of the additional agent. In some embodiments, the additional agent is, for example, an anti-inflammatory compound such as sulfasalazine, another non-steroidal anti-inflammatory compound, or a steroidal anti-inflammatory compound. In some embodiments, the additional agent is another lympho-depleting antibody such as another anti-CD52 antibody, an anti-CD20 antibody, an anti-BAFF antibody, an anti-BAFF-R antibody, and the like. In some embodiments, the additional agent is, e.g., a cytokine (e.g., IL-7), anti-cytokine receptor antibody, or a soluble receptor, that skews, manipulates, and/or augments the reconstitution process that occurs following lymphodepletion mediated by an anti-CD52 antibody (See, e.g., Sportes et al., "Cytokine Therapies: Ann. N.Y. Acad. Sci. 1182:28-38 (2009)). In another embodiment, a synthetic peptide mimetic can be administered in conjunction with an antibody of the present invention.

Because antibodies of this invention target CD52-expressing cells, the antibodies also can be used to deplete CD52+ cell types other than T cells and B cells. For example, studies have shown that vascular leukocytes (VLC) and Tie2+ monocytes—myeloid cells expressing high levels of CD52—promote tumor angiogenesis and contribute to tumor resistance to anti-VEGF therapy. Pulaski et al., *J. Translational Med.* 7:49 (2009). Anti-CD52 antibodies of this invention thus can be used to inhibit tumor angiogenesis by targeting VLC and Tie2+ monocytes. For this purpose, the anti-CD52 antibodies can be administered systemically, or locally at a site of neovascularization, such as a tumor site. Anti-CD52 antibody therapy can be used in conjunction with standard-of-care cancer treatment such as chemotherapy, surgery, or radiation, or with another targeted therapy such as anti-VEGF antibody therapy. Anti-CD52 antibody therapy can be used to treat, for example, breast cancer, lung cancer, glioma, colorectal cancer, and any other indications of anti-VEGF antibodies. Anti-CD52 antibody therapy also can be used in other neovascularization conditions including non-oncological neovascular conditions.

Studies have shown that lymphocyte depletion by alemtuzumab is mediated by neutrophils and NK cells (Hu et al., *Immunology* 128:260-270 (2009). Thus, in an embodiment of combination therapy, an agent that stimulates neutrophils and NK cells can be administered to a patient, before, during or after anti-CD52 antibody therapy, to augment the antibody therapy. Stimulating neutrophils and/or NK cells include, without limitation, (1) increasing their rates of division, (2) increasing their cell surface expression of the Fc receptors corresponding to the isotype of the anti-CD52 antibody (e.g., FcγRIIIa and FcγRIIIb, FcγRII, FcγRI, and FcαRI), (3) mobilizing and increasing the number of circulating cells, (4) recruiting the cells to target sites (e.g., sites of tumors, inflammation, or tissue damage), (5) and increasing their cytotoxic activity. Examples of agents that stimulate neutrophils and/or NK cells include, for example, granulocyte monocyte colony stimulating factor (GM-CSF) (e.g., LEUKINE® or sargramostim and molgramostim); granulocyte colony stimulating factor (G-CSF) (e.g., NEUPOGEN® or filgrastim, pegylated filgrastim, and lenograstim); interferon gamma (e.g., ACTIMMUNE®); CXC chemokine receptor 4 (CXCR4) antagonists (e.g., MOZOBIL™ or plerixafor); and CXC chemokine receptor 2 (CXCR2) agonists. The neutrophil count of the patient may be monitored periodically to ensure optimal treatment efficacy. The neutrophil count of the patient also can be measured prior to the start of the anti-CD52 antibody treatment. The stimulator's amount can be adjusted based on the patient's neutrophil count. A higher dose of the stimulator may be used if the patient has a lower than normal neutrophil count. During periods of neutropenia, which may be caused by treatment with the anti-CD52 antibody, a higher dose of the neutrophil stimulator may also be administered to maximize the effect of the anti-CD52 antibody.

Because neutrophil and/or NK stimulation improves the efficacy of anti-CD52 antibody therapy, this embodiment of combination therapy allows one to use less antibody in a patient while maintaining similar treatment efficacy. Using less anti-CD52 antibody while maintaining treatment efficacy may help reduce side effects of the anti-CD52 antibody, which include immune response in the patient against the administered antibody as well as development of secondary autoimmunity (autoimmunity that arises during or after anti-CD52 antibody treatment). This embodiment of combination of therapy is also useful in an oncology setting, e.g., when the patient has neutropenia.

In another embodiment of combination therapy, one can use a stimulator of regulatory T cells to augment anti-CD52 antibody therapy. It has been shown that anti-CD52 antibodies deplete $CD4^+CD25^+FoxP3^+$ regulatory T cells to a much lesser extent as compared to other $CD4^+$ T cells. Regulatory T cells (also known as "Treg" or suppressor T cells) are cells that are capable of inhibiting the proliferation and/or function of other lymphoid cells via contact-dependent or contact-independent (e.g., cytokine production) mechanisms. Several types of regulatory T cells have been described, including $\gamma\delta$ T cells, natural killer T (NKT) cells, $CD8^+$ T cells, $CD4^+$ T cells, and double negative $CD4^-CD8^-$ T cells. See, e.g., Bach et al., Immunol. 3:189-98 (2003). $CD4^+CD25^+FoxP3^+$ regulatory T cells have been referred as "naturally occurring" regulatory T cells; they express CD4, CD25 and forkhead family transcription factor FoxP3 (forkhead box p3). Thus, in this embodiment of combination therapy, one can administer an agent that stimulates $CD4^+CD25^+FoxP3^+$ regulatory T cells before, during or after the anti-CD52 antibody therapy, to skew the composition of the immune system following lymphodepletion. The agent may, for example, activate those T cells, stabilize and/or expand the population of the cells, mobilize and increase circulation of the cells, and/or recruit the cells to target sites. Examples of such agents are rapamycin, active or latent TGF-$\beta$ (e.g., TGF-$\beta$1, TGF-$\beta$2, TGF-$\beta$3, TGF-$\beta$4, and TGF-$\beta$5), IL-10, IL-4, IFN-$\alpha$, vitamin D (e.g., vitamin D3), dexamethasone, and mycophenolate mofetil (See, e.g., Banat et al., J. Exp. Med. 195:603-616 (2002); Gregori et al., J Immunol. 167: 1945-1953 (2001); Battaglia et al., Blood 105: 4743-4748 (2005); Battaglia et al., J. Immunol. 177:8338-8347 (2006)).

In this invention, an effective amount of anti-CD52 antibody for treating a disease is an amount that helps the treated subject to reach one or more desired clinical end points. For example, for lupus (whose manifestations include systemic lupus erythematosus, lupus nephritis, cutaneous lupus erythematosus, CNS lupus, cardiovascular manifestations, pulmonary manifestations, hepatic manifestations, haematological manifestations, gastrointestinal manifestations, musculoskeletal manifestations, neonatal lupus erythematosus, childhood systemic lupus erythematosus, drug-induced lupus erythematosus, anti-phospholipid syndrome, and complement deficiency syndromes resulting in lupus manifestations; See, e.g., Robert G. Lahita, Editor, Systemic Lupus Erythematosus, 4th Ed., Elsevier Academic Press, 2004), clinical endpoints can be measured by monitoring of an affected organ system (e.g., hematuria and/or proteinuria for lupus nephritis) and/or using a disease activity index that provides a composite score of disease severity across several organ systems (e.g., BILAG, SLAM, SLEDAI, ECLAM). See, e.g., Mandl et al., "Monitoring patients with systemic lupus erythematosus" in Systemic Lupus Erythematosus, $4^{th}$ edition, pp. 619-631, R. G. Lahita, Editor, Elsevier Academic Press, (2004).

The antibodies or portions thereof of the invention can be used to treat an individual who has previously been treated with Campath-1H® who has developed neutralizing antibodies to Campath-1H® (e.g., a Campath-1H®-refractory individual). For example, one could treat an individual having an autoimmune disease (e.g., multiple sclerosis, lupus, vasculitis) and/or a cancer (e.g., a leukemia (e.g., chronic lymphocytic leukemia), a lymphoma (e.g., non-Hodgkin's lymphoma)) who has previously been treated with Campath-1H® (e.g., with one or more courses of Campath-1H® treatment) and who has developed neutralizing antibodies to Campath-1H® that reduce the efficacy of further Campath-1H® treatment. In another embodiment, one could treat an individual who had become refractory to treatment with a particular humanized antibody described herein with one of the other humanized antibodies described herein.

By way of example, the antibodies or portions of this invention are useful therapeutic agents for treating multiple sclerosis (MS). MS includes relapsing-remitting, secondary progressive, primary progressive, and progressive relapsing multiple sclerosis ((Lublin et al., Neurology 46 (4), 907-11 (1996)), diagnosed is made by, for example, the history of symptoms and neurological examination with the help of tests such as magnetic resonance imaging (MRI), spinal taps, evoked potential tests, and laboratory analysis of blood samples. In MS, the goals of treatment are to reduce the risk, frequency, and/or severity of relapses, prevent or reduce disability arising from disease progression, and promote tissue repair. Thus, an amount of anti-CD52 antibody that helps achieve a clinical endpoint consistent with one or more of these goals is an effective amount of antibody for the treatment. For example, an anti-CD52 antibody or portion of this invention can be indicated for treating relapsing forms of MS to slow or reverse the accumulation of physical disability and reduce the frequency of clinical exacerbations. The antibody or portion may be tested in clinical trials for its efficacy in reducing the risk of relapse and the risk for progression of clinically significant disability. The antibody or portion can be administered to patients having an active relapse or at risk of developing a relapse, or to a patient experiencing progressive deterioration. See e.g., U.S. Pat. Publication 2008/0267954, the disclosure of which is herein incorporated by reference in its entirety.

The methods and compositions of this invention are useful in treating MS patients who have had a suboptimal response to prior MS-modifying therapy. The MS patient may be a relapsing-remitting (RRMS) patient who has previously received an MS-modifying therapy, for example, interferon beta-1a (e.g., AVONEX® and REBIF®), interferon beta-1b (e.g., BETASERON® and EXTAVIA®), glatiramer acetate (e.g., COPAXONE®), mitoxantrone (e.g., NOVANTRONE®), natalizumab (e.g., TYSABRI®), fingolimod (e.g., GILENYA®), and teriflunomide (e.g., AUBAGIO™). In one embodiment, the previous MS-modifying therapy is not alemtuzumab (e.g., CAMPATH, MABCAMPATH, or LEMTRADA™) or another anti-CD52 antibody. The previously treated patient may have had an MS relapse or renewed MS activity while being treated or shortly after being treated (e.g., within one year). Renewed MS activity may include new or worsening neurological symptoms attributable to MS, an increase in the patient's EDSS score (Kurtzke, Neurology 1983; 33:1444-52), a decrease in the patient's Multiple Sclerosis Functional Composite (MSFC) score (Cutter et al., Brain 1999; 122(Pt 5):871-82), new or enlarged cranial or spinal lesions, brain volume loss, and/or neurodegeneration determined by optical coherence tomography (OCT). For example, the patient may have had at least one previous relapse while being treated with interferon beta or glatiramer. The patient may also have at least one of the following characteristics: onset of symptoms 10 or fewer years before initiation of first cycle of anti-CD52 antibody treatment; at least two attacks in the two years before initiation of first cycle of anti-CD52 antibody treatment; at least one relapse while on interferon beta or glatiramer after at least six months of treatment; Expanded Disability Status Scale (EDSS) score of 5.0 or lower; and cranial and spinal magnetic resonance imaging (MRI) abnormalities.

In one embodiment, an antibody or portion of the invention is administered to an MS patient having an autoimmune disease (e.g., multiple sclerosis (MS)) in a regimen comprising administration of a first cycle of the antibody followed by at least one further cycle of the antibody, in which each treatment cycle comprises 1-5 doses that are applied on consecutive days, and wherein each treatment cycle is separated from the next cycle by at least 1-24 months (e.g., 12 months). For example, in one embodiment, a patient having multiple sclerosis is treated with a first cycle of the antibody comprising 5 daily doses of the antibody followed by at least one further cycle of antibody treatment, in which the treatment occurs one year after the first cycle and comprises 3 doses of the antibody applied on consecutive days. In one embodiment, an anti-CD52 antibody is administered to a patient having multiple sclerosis on five consecutive days at 12 mg/day in a first treatment cycle; and after one year, the anti-CD52 antibody is administered to the patient on three consecutive days at 12 mg/day in a second treatment cycle. In one embodiment, an anti-CD52 antibody is administered to a patient having multiple sclerosis at a total dose of 60 mg over five consecutive days in a first treatment cycle; and after one year, the anti-CD52 antibody is administered to the patient at a total dose of 36 mg over three consecutive days in a second treatment cycle.

In the methods and compositions of this invention, a "year" does not have to equal exactly 365 days or 12 months. For example, the second cycle of an anti-CD52 antibody does not have to be administered exactly 365 days or 12 months after the first cycle of an anti-CD52 antibody is administered. The second cycle may be initiated 365 days plus or minus up to 6 months, plus or minus up to 5 months, plus or minus up to 4 months, plus or minus up to 3 months, plus or minus up to 2 months, plus or minus up to one month, plus or minus up to 4 weeks, plus or minus up to 3 weeks, plus or minus up to 2 weeks, or plus or minus up to one week after the initiation of the first cycle.

In another embodiment, a patient having MS is only re-treated once evidence of renewed MS activity has been observed (See, e.g., WO 2008/031626; the disclosure of which are incorporated herein by reference in their entirety). In some embodiments, it may be necessary to administer more frequent courses of treatment (e.g., every four months, every six months) if patients with more advanced forms of MS or more progressive forms of other autoimmune diseases (such as vasculitis; See, e.g., Walsh et al., Ann Rheum Dis 67:1322-1327 (2008)) experience a relapse early on after their last course of treatment or show renewed MS activity. Evidence of renewed MS activity may be determined based on the professional judgment of the treating clinician, using any means that may be available to such clinician. A variety of techniques are currently available to clinicians to diagnose renewed MS activity including, without limitation, by clinical means (relapse or progression of neurological disability) or by magnetic resonance imaging (MRI) of the brain or spinal cord. As is well understood by medical practitioners, disease activity detected via MRI may be indicated by the occurrence of new cerebral or spinal lesions on Ti (enhanced or non-enhanced)- or T2-weighted images or by the increase of the volume of such lesions.

As diagnostic methods for MS are continually evolving, it is anticipated there may be additional methods in the future that will detect renewed MS activity (e.g., magnetization transfer ratio or MR-spectroscopy). The particular diagnostic method used to detect renewed MS activity is not a limitation of the claimed invention. In certain embodiments, repeated MRIs are performed in fixed intervals after a treatment cycle in order to determine whether re-treatment of any given patient is necessary and the optimal time point for re-treatment of such patient. In general, it is desirable for re-treatment to occur before the disease re-manifests clinically.

The methods and compositions of the invention may be used in combination with other MS-modifying therapies. Non-limiting examples of MS-modifying therapies include interferon beta-1a (e.g., AVONEX® and REBIF®), interferon beta-1b (e.g., BETASERON® and EXTAVIA®), glatiramer acetate (e.g., COPAXONE®), mitoxantrone (e.g., NOVANTRONE®), natalizumab (e.g., TYSABRI®), fingolimod (e.g., GILENYA®), and teriflunomide (e.g., AUBAGIO®).

In some embodiments, the methods and compositions of the invention may be used in combination with generalized or non-specific treatments or therapies, for example steroids (e.g., corticosteroids) or dalfampridine (e.g., AMPYRA®).

In one aspect, drugs known to those skilled in the art to be effective to manage infusion-related side effects may be administered before, during, or after infusion of the anti-CD52 antibody. Such drugs include corticosteroids (e.g., methylprednisolone), acetaminophen, and antihistamines (e.g., diphenhydramine). In some embodiments, patients receive 1 g/day of intravenous methylprednisolone on one, two, three, four, or five consecutive days during a cycle of treatment with an antibody of the invention.

In one embodiment of the invention, patients may additionally receive a drug that serves as a prophylaxis against herpes. For example, patients may receive 200 mg of acyclovir (e.g., ZOVIRAX®) twice daily during administration of an antibody of the invention and for 28 days thereafter.

Formulation will vary according to the route of administration selected (e.g., solution, emulsion). An appropriate composition comprising the antibody or antigen-binding fragment to be administered can be prepared in a physiologically acceptable vehicle or carrier. The composition can comprise multiple doses or be a single unit dose composition. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Sciences, 17th Edition, Mack Publishing Co., PA, 1985). For inhalation, the compound can be solubilized and loaded into a suitable dispenser for administration (e.g., an atomizer, nebulizer or pressurized aerosol dispenser).

Diagnostic Methods and Compositions

The antibodies of the present invention also are useful in a variety of processes with applications in research and diagnosis. For instance, they can be used to detect, isolate, and/or purify human CD52 or variants thereof (e.g., by affinity purification or other suitable methods such as flow cytometry, e.g., for cells, such as lymphocytes, in suspension), and to study human CD52 structure (e.g., conformation) and function. The antibodies of this invention will be useful for in vitro applications.

The antibodies of the present invention can be used in diagnostic applications (e.g., in vitro, ex vivo). For example, the humanized antibodies of the present invention can be used to detect and/or measure the level of human CD52 in a sample (e.g., on cells expressing human CD52 in tissues or body fluids, such as an inflammatory exudate, blood, serum, bowel fluid, tissues bearing human CD52). A sample (e.g., tissue and/or body fluid) can be obtained from an individual and an antibody described herein can be used in a suitable immunological method to detect and/or measure human CD52 expression, including methods such as flow cytometry (e.g., for cells in suspension such as lymphocytes), enzyme-linked immunosorbent assays (ELISA), including chemiluminescence assays, radioimmunoassay, and immunohistology. The invention encompasses kits (e.g., diagnostic kits) comprising the anti-CD52 antibodies described herein.

In one embodiment, a method of detecting human CD52 in a sample is provided, comprising contacting a sample with an antibody of the present invention under conditions suitable for specific binding of the antibody to human CD52 and detecting antibody-CD52 complexes which are formed. In an application of the method, the antibodies described herein can be used to analyze normal versus inflamed tissues (e.g., from a human) for human CD52 reactivity and/or expression (e.g., immunohistologically) to detect associations between e.g., inflammatory bowel disease (IBD), autoimmune diseases (such as multiple sclerosis and lupus), cancer (such as non-Hodgkin's lymphoma and chronic lymphocytic leukemia), or other conditions and increased expression of human CD52 (e.g., in affected tissues). Thus, the antibodies of the present invention permit immunological methods of assessment of the presence of human CD52 in normal and inflamed tissues, through which the presence of disease, disease progress and/or the efficacy of anti-human CD52 therapy in the treatment of disease, e.g., inflammatory disease can be assessed.

In addition, the antibodies can be used to examine tissues after treatment with a depleting anti-CD52 therapeutic antibody to gauge how effective the depletion has been as well as to determine whether there has been any downregulation in the expression of CD52 (Rawstrom et al., Br. J. Heam., 107:148-153 (1999)).

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and embodiments, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

The following examples are meant to illustrate the methods and materials of the present invention. Suitable modifications and adaptations of the described conditions and parameters normally encountered in the art which are obvious to those skilled in the art are within the spirit and scope of the present invention. The terms "antibody" and "immunoglobulin" are used interchangeably herein. The terms "antigen-binding fragment" and "antigen-binding portion" also are used interchangeably herein.

EXAMPLES

The following examples are meant to illustrate the methods and materials of the present invention. Suitable modifications and adaptations of the described conditions and parameters normally encountered in the art that are obvious to those skilled in the art are within the spirit and scope of the present invention.

Example 1

Expression and Characterization of Antibody Ab1

Antibody Ab1 was derived from Ab26 by changing residue 33 (within L-CDR1) in Ab26's light chain to Asp. Additionally, a variant antibody was generated wherein the first 33 amino acid residues of the light chain of Ab26 were deleted (the Del33 antibody). The variant light chain DNA was synthesized in pDONR221 Entry vectors by DNA2.0 in the light-chain backbone and subcloned into HEK293 expression vector pCEP4(-E+I)Dest by Gateway cloning. A large-scale DNA prep was then performed for HEK293-EBNA cell transfection. All variants and the parent Ab26 control light chain were co-transfected with the parent Ab26 heavy chain at 1:1 ratio.

For purification, 160-300 ml of transfected media were used to purify Ab26, Del33, and Ab1 antibodies using 1 ml HiTrap Protein A columns (GE) and a multichannel pump set up. A280 in collected fractions was measured by NanoDrop. Fractions #1 and #2, containing the majority of the protein, were combined, buffer-exchanged into 50 mM sodium phosphate, 150 mM sodium chloride, pH 6.0, and concentrated using Amicon-4 10 kD cutout columns. The protein purification yield is summarized in Table 3.

TABLE 3

Protein purification yields

| Antibody | CM volume (ml) | Protein concentration (mg/ml) | Volume of purified material (μl) | Total protein (μg) |
|---|---|---|---|---|
| Ab26 | 300 | 2.86 | 370 | 1058 |
| Del33 | 160 | 0.04 | 124 | 4 |
| Ab1 | 300 | 1.71 | 900 | 1539 |

The Del33 mutant was not expressed or purified at high levels, likely due to a misfolding problem linked to the deletion. Ab1 and Ab26 were successfully purified to homogeneity for further characterization. N-terminal sequencing of the first 15 amino acids confirmed that all three samples had the expected sequence.

Figure 17:
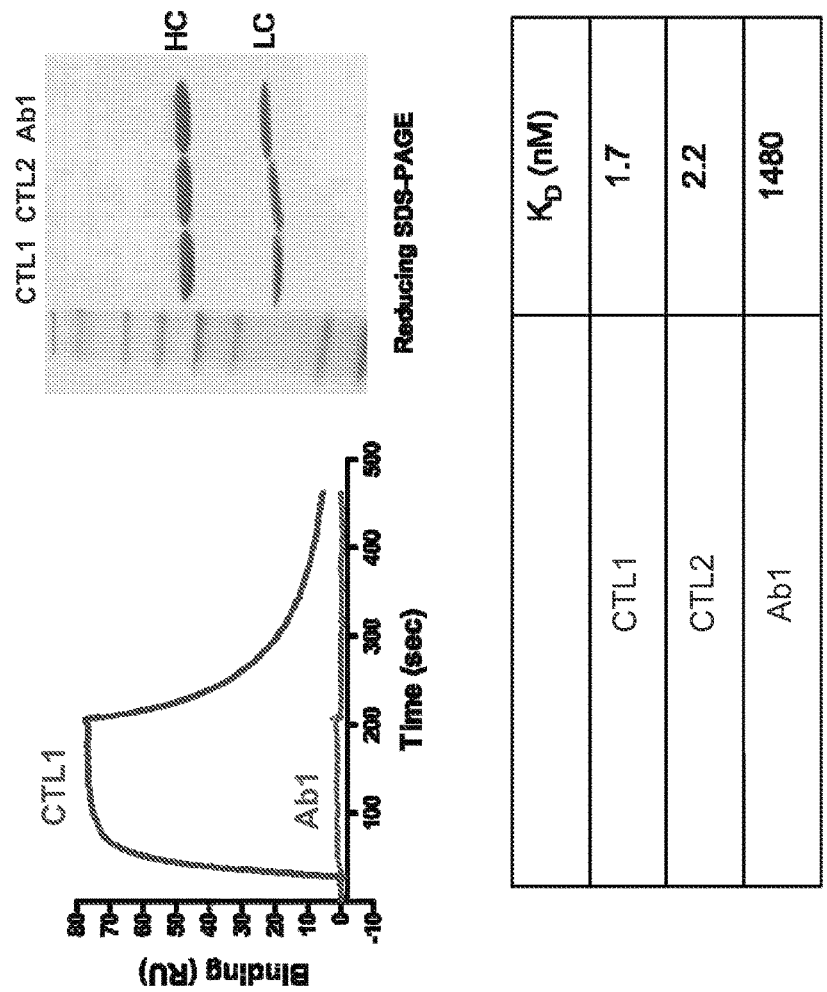
FIG. 17 depicts results from experiments characterizing the Ab1 antibody purified from HEK293 cells. The graph and table show results of BIACORE™ assays measuring affinity of the Ab1 and two preparations of Ab26 (CTL1 and CTL2) for a CD52 peptide. The upper right panel is a photograph of a reducing SDS-PAGE gel showing the heavy chain (HC) and light chain (LC) of two preparations of Ab26 (CTL1 and CTL2) and Ab1 antibodies.

Ab26 and Ab1 were also expressed in CHO cells and purified on protein A columns. The antibodies were characterized by BIACORE™ for their affinity for CD52 peptide. Results are shown in FIG. 17 and Table 4 for antibodies produced in HEK293 cells and in FIG. 18 and Table 5 for antibodies produced in CHO cells.

TABLE 4

Binding affinity results for antibodies expressed in HEK293 cells

| Antibody | $k_a$ (×10$^6$ M$^{-1}$ s$^{-1}$) | $k_d$ (s$^{-1}$) | $K_D$ (nM) |
|---|---|---|---|
| Ab26 (preparation 1) | 7.2 | 0.01 | 1.7 |
| Ab26 (preparation 2) | 5.4 | 0.01 | 2.2 |
| Ab1 | 0.4 | 0.58 | 1480 |

TABLE 5

Binding affinity results for antibodies expressed in CHO cells

| Antibody | $k_a$ (×10$^6$ M$^{-1}$ s$^{-1}$) | $k_d$ (s$^{-1}$) | $K_D$ (nM) |
|---|---|---|---|
| Ab26 | 6.2 | 1.6 | 2.6 |
| Ab1 | 0.3 | 38.3 | 1250 |

CD52 BIACORE™ binding assays were performed as follows: A low level of a CD52 peptide mimotope (CGQNDTSQTSSPSAD (SEQ ID NO: 87)) was immobilized on a CM5 chip via thiol chemistry using an N-terminal Cys. Several concentrations of anti-CD52 antibody made in HBS-EP running buffer (1 to 20 nM) were injected over the surface to monitor the binding. Kinetic analysis was performed using Scrubber2 software.

Antibody Ab1 demonstrated more than 400-fold reduction in affinity compared to Ab26. No clear binding signal was observed by the Ab1 antibody at 1-10 nM concentrations, where Ab26 displays high binding affinity (FIG. 17). Higher concentrations of Ab1 (up to 1900 nM) were used in an effort to get a quantitative measure for the loss of the binding affinity by the variant. The 1250 nM $K_D$ obtained from CHO-produced Ab1 was consistent with that of the HEK293-produced Ab1 (1480 nM). The decrease in affinity is reflected in both reduced on-rate and increased off-rate in the kinetic binding.

Figure 19:
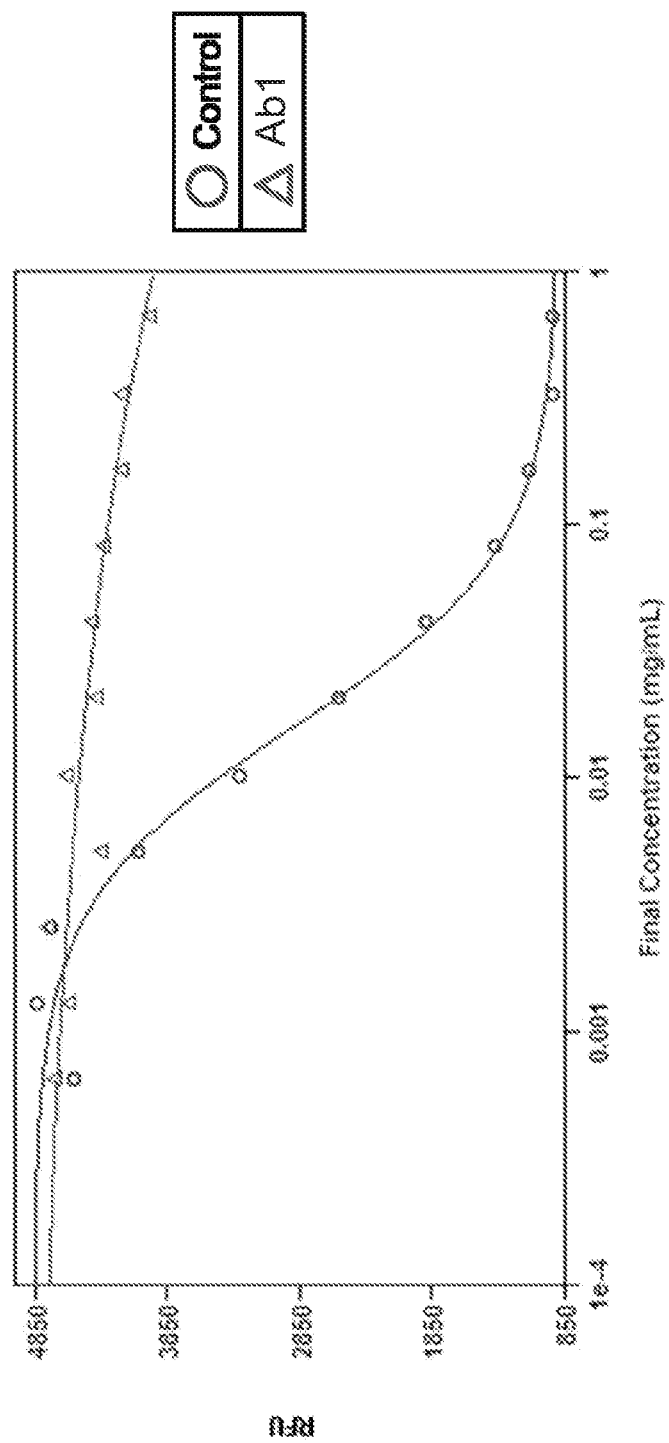
FIG. 19 is a graph depicting results from a CDC assay of the Ab1 antibody and Ab26 antibody (Control). The results are expressed in relative fluorescence units (RFU) as a function of final concentration in mg/ml of the antibody.

A CDC potency assay was performed to assess whether the affinity loss would affect effector function by measuring cell-killing via complement dependent cytotoxicity. All variant and control antibody materials were serially diluted 1:2 across one solid black 96-well plate from 2 mg/mL to 0.002 mg/mL in assay medium (phenol-red free IMDM medium+ 0.1% BSA). Materials with a stock concentration <2 mg/mL were tested neat. Normal human serum complement (Quidel Corporation) was added to all wells at a final concentration of 5% (v/v). Pfeiffer b-lymphocytes (ATCC) were then added at a final concentration of 0.6×10$^6$ cells/mL. A negative cell lysis control (assay medium+cells), a positive cell lysis control (assay medium+cells+2% (w/v) Triton X-100), and a positive dose response control (4 mg/mL control material) were included on the same plate. The reactions were incubated for one hour in a humidified, 37° C., 5% CO$_2$ incubator. Fifty microliters of pre-warmed alamarBlue® detection reagent (Life Technologies) were then added to all wells followed by incubation in reduced light for four hours. The relative reduction of alamarBlue® was measured using a fluorescent plate reader (ex: 530 nm, em: 590, cutoff: 570 nm). Softmax Pro, v. 5.3 (Molecular Devices) was used to generate dose-response curves fit to a four parameter model. The result is shown in FIG. 19. Ab26 (Control) demonstrated concentration dependent cell killing as expected. Antibody Ab1 produced in CHO cells demonstrated little detectable CDC activity in the concentration range tested. These experiments suggest that a single amino acid substitution may have a significant impact on Ab26 biological function.

Example 2

Analysis of CD52 binding affinity of Anti-CD52 Antibodies

Antibodies Ab4, Ab3, Ab24, Ab10, Ab12, and Ab25 (see Tables 1 and 2) were expressed in HEK293 cells. The light chain DNA was synthesized, subcloned, and transiently expressed in HEK293 cells as follows. The DNA molecules were synthesized in pDONR221 Entry vectors by DNA2.0 in the light-chain backbone and subcloned into HEK293 expression vector pCEP4(-E+I)Dest by Gateway cloning. The light chain-expressing vector was co-transfected with an Ab26 heavy chain-expressing vector into HEK293 cells. Ab26 DNA was used as a control for transfection. The conditioned media were screened for protein expression level by Octet using a protein A sensor and for CD52-binding affinity by BIACORE™ using a CD52 peptide chip. The results are shown in FIG. 1.

Figure 2:
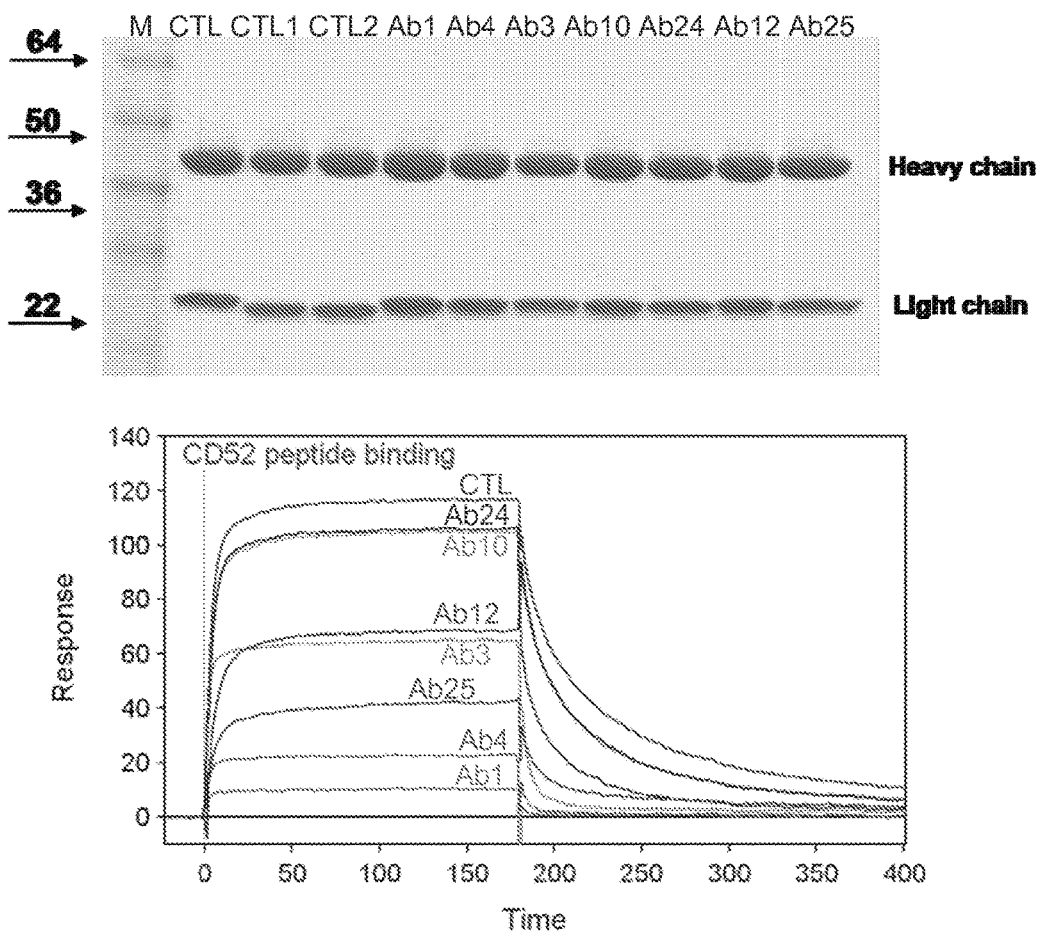
FIG. 2 depicts results from experiments characterizing purified anti-CD52 antibodies. The upper panel is a photograph of an SDS-PAGE gel showing the separation of the heavy chain and light chain of the anti-CD52 antibodies. Molecular weight markers are shown in the lane marked (M). The graph and table in the lower panels show the results of BIACORE™ binding assays.

Ab24 and Ab10 antibodies demonstrated strong CD52 binding affinity. Ab4 and Ab3 demonstrated lower CD52 binding affinity. To confirm this finding, Ab4 and Ab3 were purified using a protein A column for further characterization. An SDS-PAGE gel of Ab26 antibody (CTL), Ab26 antibody from two transfections (CTL1 and CTL2), Ab1, Ab4, Ab3, Ab10, Ab24, Ab12, and Ab25 and the BIACORE™ CD52 peptide binding results are shown in FIG. 2.

Results with the purified antibodies confirmed the initial media screening data. Ab4 and Ab3 demonstrated lower CD52 binding affinity.

Example 3

Large-Scale Preparation and Characterization of Ab24 and Ab10 Antibodies

Figure 3:
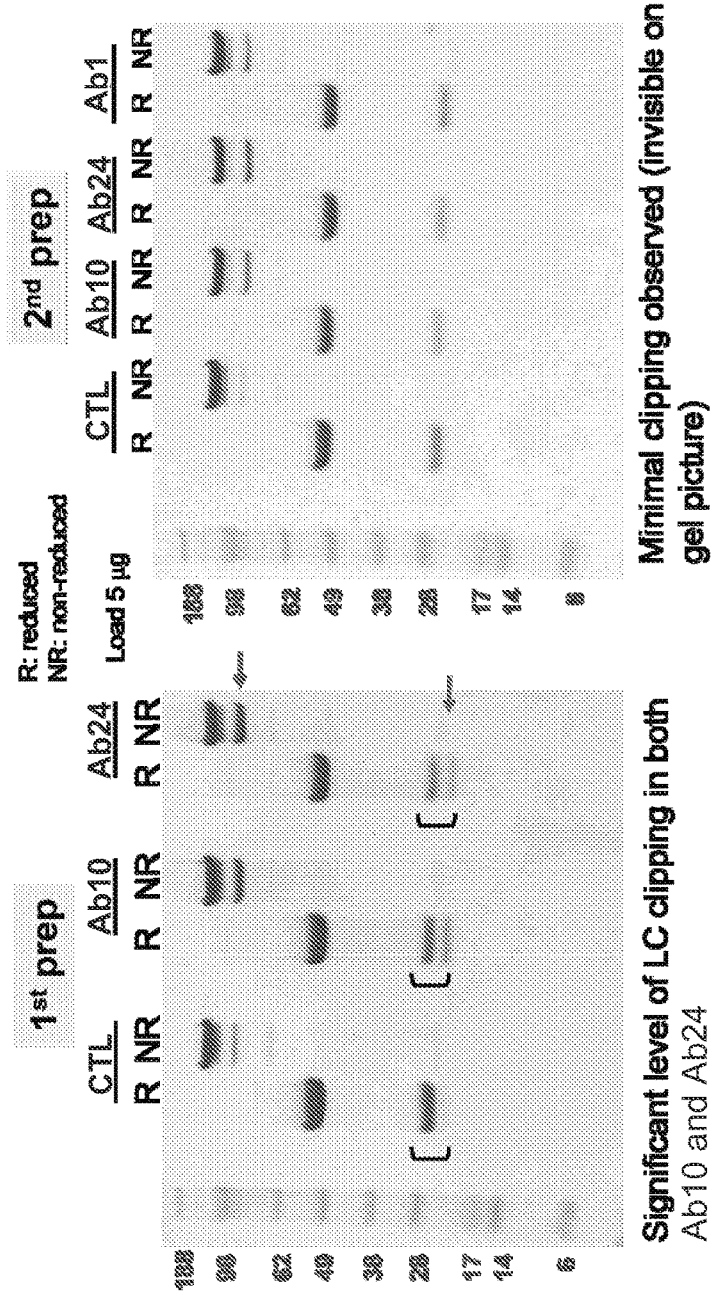
FIG. 3 depicts photographs of SDS-PAGE gels showing preparations of Ab24 and Ab10 antibodies produced in CHO cells. The gels also show a control anti-CD52 (CTL) antibody and the Ab1 antibody. The 100 kD species and LC clipping are indicated with arrows.

Ab24 and Ab10 antibodies were produced in larger scale in CHO K1 cells to determine their CD52 binding and inhibitory properties. Light chain clipping was observed in the two antibodies; and a band below 150 kD was observed in the non-reducing (NR) gel (designated here as the "100 kD species") (FIG. 3).

Figure 4:
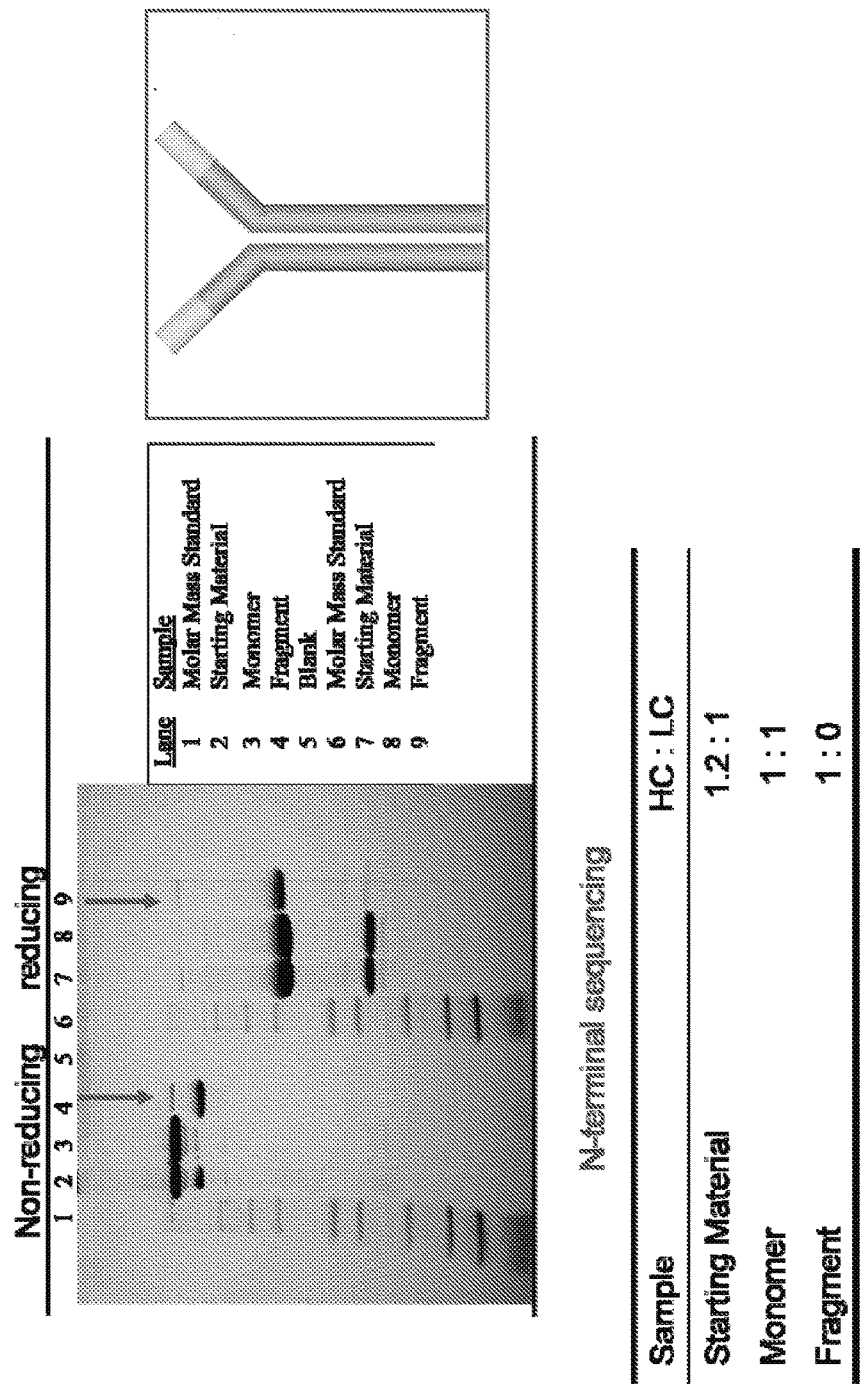
FIG. 4 depicts a photograph of an SDS-PAGE gel showing the 100 kD species found in Ab24 and Ab10 antibodies with a "heavy-chain only" dimer illustration on the right. N-terminal sequencing results are also shown.

The light chain clipping issue was minimized by optimizing the tissue culture conditions and by omitting the media storage step at 4° C. There seemed to be a small amount of 100 kD species (below 150KD) produced despite these improvements (FIG. 3). The two antibodies were further characterized. There were 9-12% and 18-20% of 100 kD species found in two larger scale preps of Ab24 and Ab10, respectively, by SEC-HPLC. An intact mass spectrometry experiment confirmed the sequences of the antibodies. N-terminal sequencing of the low molecular weight species suggested only the N-terminal sequence of the heavy chain was present. When the 100 kD species was collected and analyzed on an SDS-PAGE gel, only the heavy chain was observed. These results suggest that the 100 kD species contained only heavy chain (FIG. 4).

Example 4

Preparation and Screening of Additional Anti-CD52 Antibodies

The expression vectors for antibodies Ab2, Ab6, Ab7, Ab5, Ab13, Ab15, Ab 17, Ab 18, Ab 19, Ab23, Ab22, Ab11, Ab20, Ab 16, Ab21, and Ab14 (see Tables 1 and 2) were transfected into HEK293 cells. All antibodies were expressed at >0.2 µg/ml when the conditioned media was analyzed with a protein A sensor on Octet (FIG. 5, upper panel). BIACORE™ CD52 affinity screening of these media samples was then used to identify lead candidates (FIG. 5, middle and lower panels).

Antibodies Ab2, Ab6, Ab7, and Ab5 had low binding affinity for CD52. Several other antibodies demonstrated higher binding affinity for CD52. These antibodies included Ab22, Ab20, Ab21, Ab14, Ab14, and Ab11. Antibodies Ab22, Ab20, Ab21, Ab14, Ab14, and Ab11 were studied further.

Figure 6:
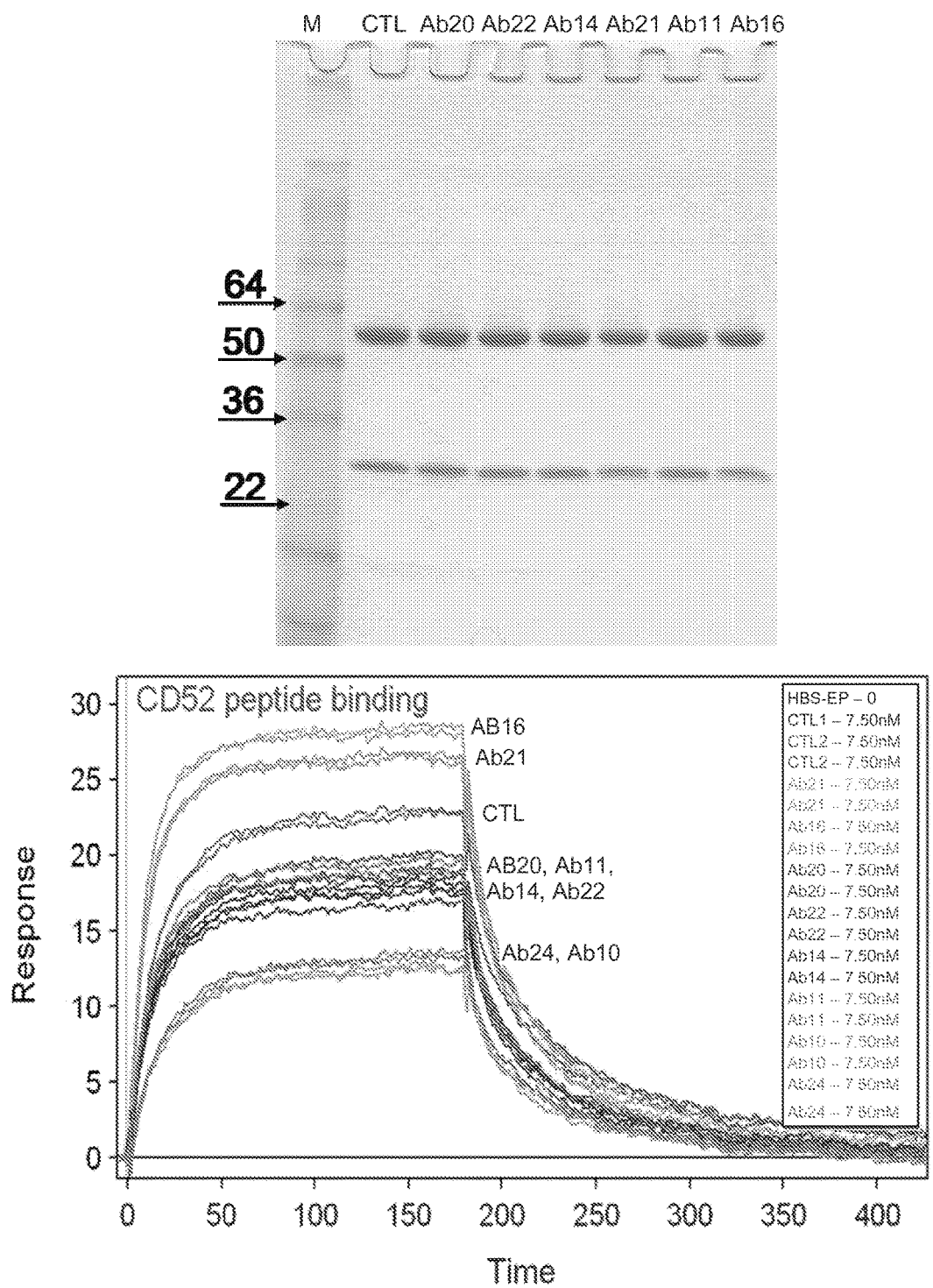
FIG. 6 depicts results from experiments characterizing CD52 binding of purified anti-CD52 antibodies. The left panel is a photograph of an SDS-PAGE gel showing the heavy chain and light chain of the wild-type (CTL) and other antibodies. Molecular weight markers are shown in the lane marked (M). The right panel graph shows the results of BIACORE™ binding assays.

These six antibodies (Ab22, Ab20, Ab21, Ab14, Ab14, and Ab11) were scaled-up to one TripleFlask/antibody transient expression. (This flask has three parallel growth surfaces to provide a total culture area of 500 cm². ) The antibodies were purified from 160 ml of conditioned media using 1 ml HiTrap protein A affinity columns (GE Healthcare). The reducing SDS-PAGE gel showed successful purification and reasonable antibody purity (FIG. 6). For CD52 binding comparison on BIACORE™, the purified samples were diluted to 60 and 7.5 nM in HBS-EP and injected over a CD52 peptide #741 chip (the results are shown in FIG. 6 for 7.5 nM). The BIACORE™ binding analysis confirmed the initial media screening result that these antibodies have tight binding to CD52 peptide. A kinetics binding experiment indicated the following affinity rank:
(Ab16, Ab21)>Ab26>(Ab20, Ab11, Ab14, Ab22)>(Ab24, Ab10)

Ab16 and Ab21 were shown to have affinities higher than Ab26.

Example 5

Analysis of Stability of Anti-CD52 Antibodies

Figure 20:
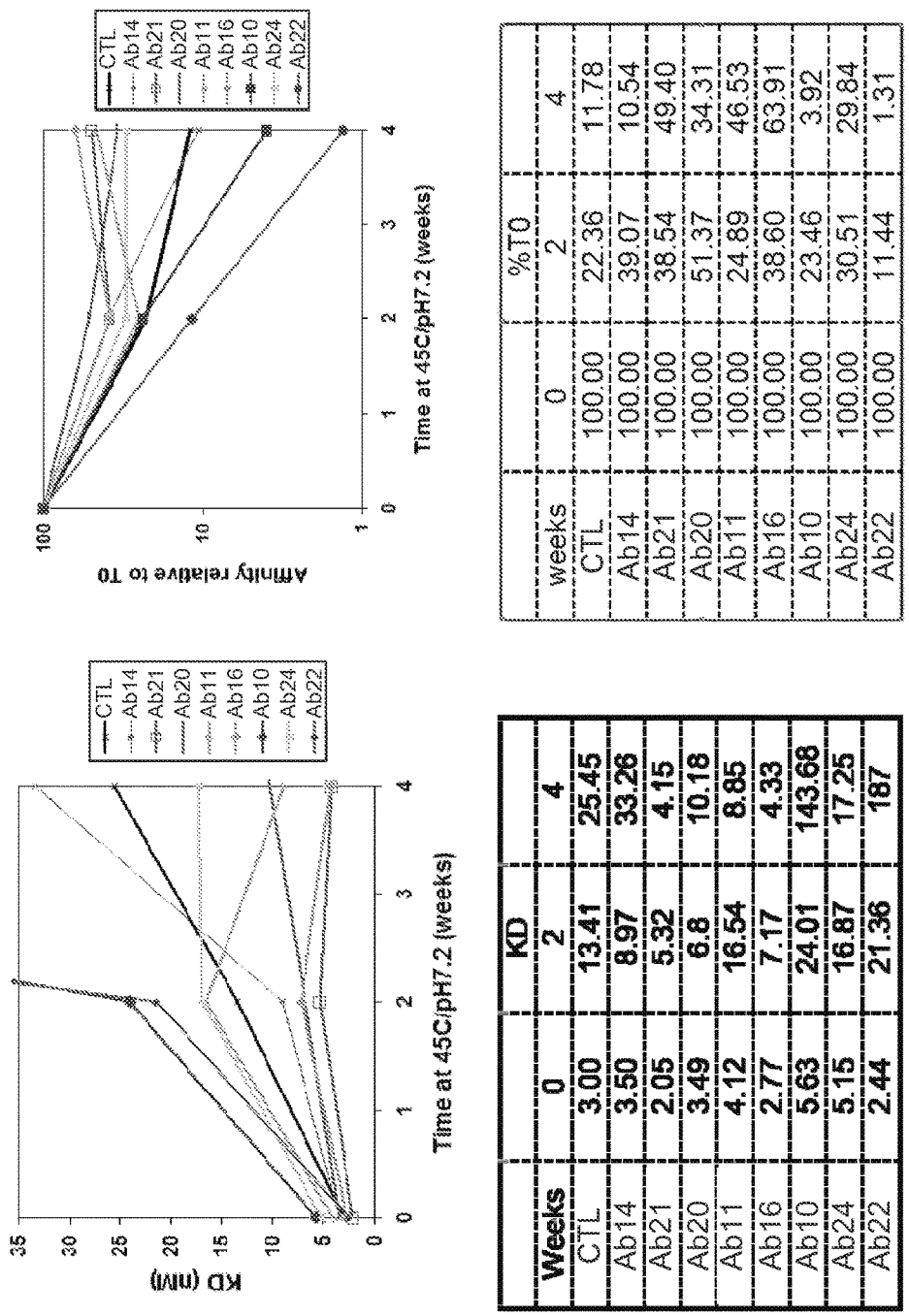
FIG. 20 depicts results from stability screening of anti-CD52 antibodies. The upper left panel graph shows $K_D$ (nM) as a function of time (weeks) at 45° C. and pH 7.2 for Ab26 (CTL) and variant antibodies. The upper right panel graph shows affinity relative to T0 as a function of time (weeks) at 45° C. and pH 7.2 for Ab26 (CTL) and variant antibodies.

To determine whether stability of the anti-CD52 antibody variants had been affected, high temperature conditions were used to compare and to screen the anti-CD52 antibody variants. Ab26 and select variants purified from HEK293 cells were used for the initial screening. The proteins (85 µg) were diluted in PBS, pH 7.2, to 0.4 mg/ml, and incubated at 45° C. for 4 weeks. Their binding affinity to CD52 peptide was measured on BIACORE™. One microgram of each variant taken at Week #2 and Week #4 was serially diluted in HBS-EP to 7.5, 2.5, and 0.8 nM, and injected over a CD52 peptide #741 chip. The preliminary binding constants were calculated using Scrubber software and are shown in FIG. 20 (Ab26 is labeled as "CTL").

The results indicate that Ab21, Ab16 and Ab20 antibodies retain significant CD52 binding affinity over 4 weeks of incubation, suggesting that they are more stable than antibody Ab26. In contrast, the Ab10 and Ab22 antibodies lost most of their binding affinity to antigen over the incubation timeframe.

Figure 21:
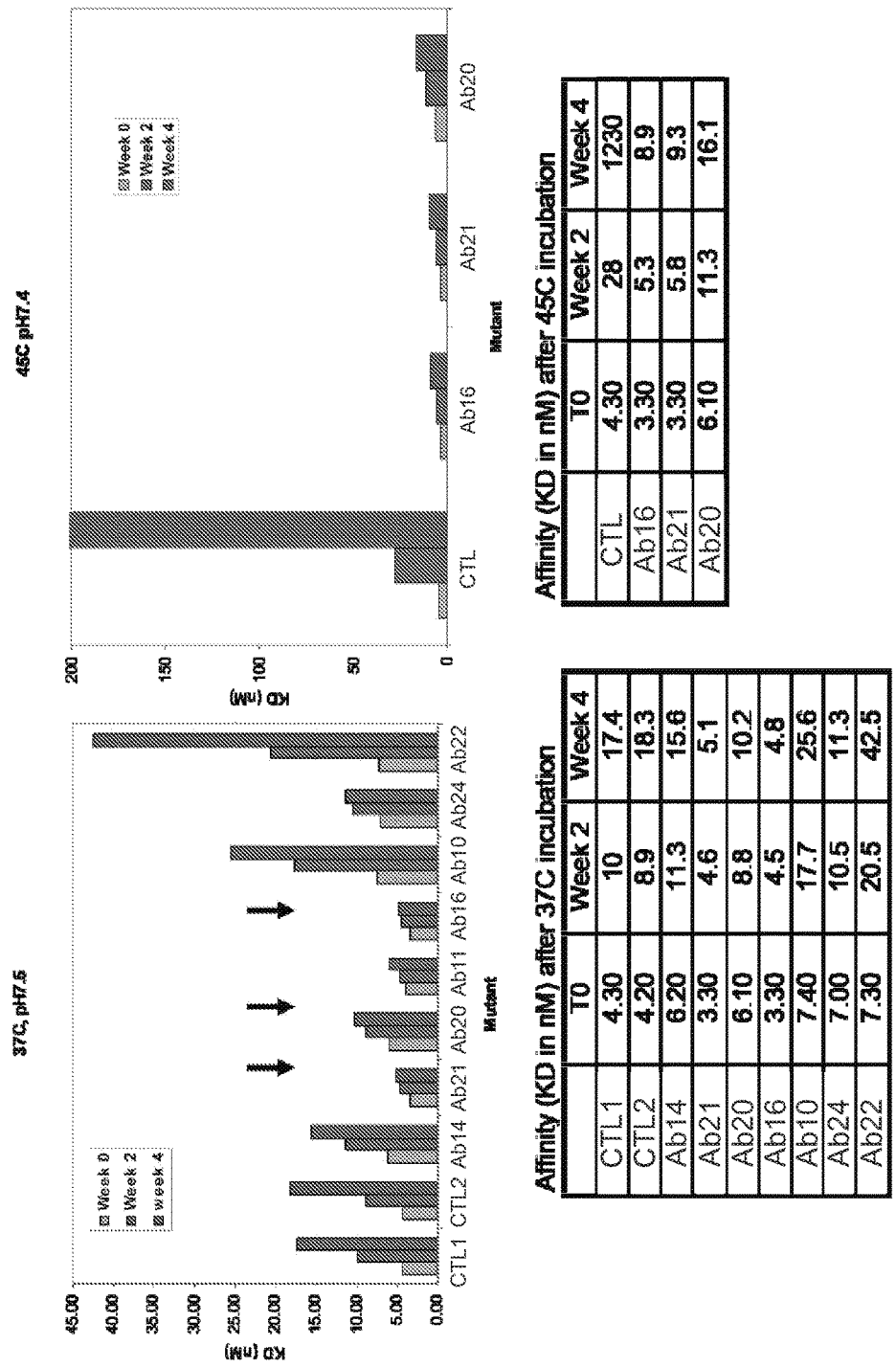
FIG. 21 depicts results from experiments testing the effect of incubation in three component buffer on stability of anti-CD52 antibodies. The upper left panel graph shows $K_D$ (nM) at Week 0, Week 2, and Week 4 at 37° C. and pH 7.5 for two preparations of Ab26 (CTL1 and CTL2) and variant antibodies. The upper right panel graph shows $K_D$ (nM) at Week 0, Week 2, and Week 4 at 45° C. and pH 7.4 for Ab26 (CTL) and variant antibodies.

To confirm the result obtained in the incubation experiment, a new preparation of the variants was generated and incubated in "3 component" buffer (10 mM succinate, 10 mM histidine, 10 mM sodium phosphate, pH 7.5) along with Ab26 antibody at 37° C. or 45° C. for 4 weeks. The "3 component" buffer is typically utilized in antibody manufacturability tests. The amount of incubated material is listed in Table 6. The Ab21, Ab16 and Ab20 antibodies were also incubated at 45° C. in the same buffer. Aliquots were taken at Week 2 and Week 4 (T2 and T4) to assess their affinity to CD52 peptide by BIACORE™. Each sample was diluted to 7.5, 3.75, and 1.875 nM in HBS-EP and injected over a CD52 peptide #741 chip for 3 min, followed by 3 min dissociation in buffer. The apparent $K_D$'s are shown in FIG. 21.

TABLE 6

Amount of Incubated Material in Three Component Buffer Experiment

| Mutant | Concentration (mg/ml) | 37° C. incubation (µg) | 45° C. incubation (µg) |
|---|---|---|---|
| Ab20 | 0.363 | 75 | 75 |
| Ab22 | 0.350 | 75 | — |
| Ab16 | 0.366 | 75 | 75 |
| Ab21 | 0.391 | 75 | 75 |
| Ab14 | 0.359 | 75 | — |
| Ab24 | 0.361 | 75 | — |
| Ab10 | 0.382 | 75 | — |
| Ab11 | 0.401 | 75 | — |
| CTL1 | 0.354 | 75 | — |
| CTL2 | 0.375 | 75 | 75 |

Results suggested that the binding affinity of the Ab21, Ab16 and Ab20 antibodies remained the same or only slightly decreased at 37° C. and 45° C. after 4 weeks of incubation, whereas Ab26 (CTL, CTL1, and CTL2) lost binding affinity over time. The $K_D$ of Ab26 (CTL) changed from 4.3 nM to 1230 nM after incubation at 45° C. after 4 weeks, indicating a decrease in binding to CD52. This suggests that these mutants are indeed more resistant to instability over time at the L-CDR1 site.

Figure 22:
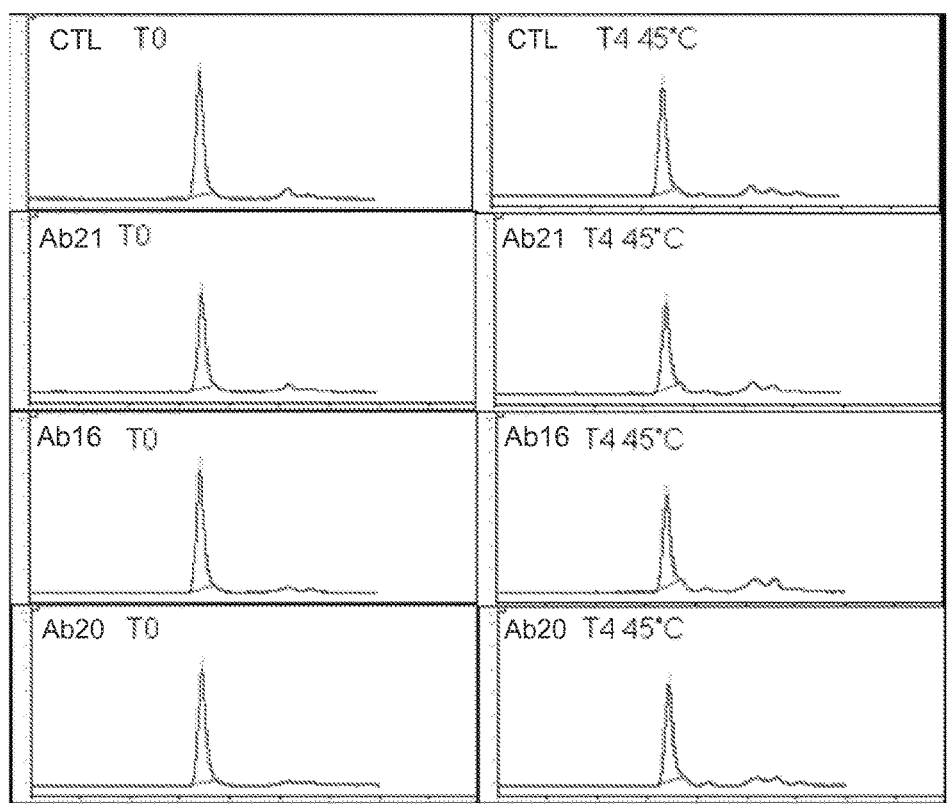
FIG. 22 depicts results from a size-exclusion chromatography (SEC)-HPLC analysis of Ab26 (CTL), Ab21, Ab16, and Ab20 after incubation at 45° C.

To verify the structural integrity of the Ab21, Ab16 and Ab20 antibodies, aggregation and fragmentation of the variants that were diluted in PBS, pH 7.2, to ~0.4 mg/ml and incubated at 45° C. for 4 weeks was assessed by SEC-HPLC. Five micrograms of protein were diluted in the mobile phase (40 mM sodium phosphate, 500 mM sodium chloride, pH 6.0) to 100 µl total volume and injected onto TSK Gel G3000 SW×1 column at 0.5 ml/min for 35 min. No significant aggregation and limited fragmentation were detected in Ab21, Ab16, Ab20, and Ab26 (CTL) (FIG. 22). Therefore, the loss of affinity in Ab26 is likely not to be caused by loss of structural integrity.

Example 6

Biological Activity of Anti-CD52 Antibodies in In Vitro Potency Assay (CDC Potency)

Figure 7:
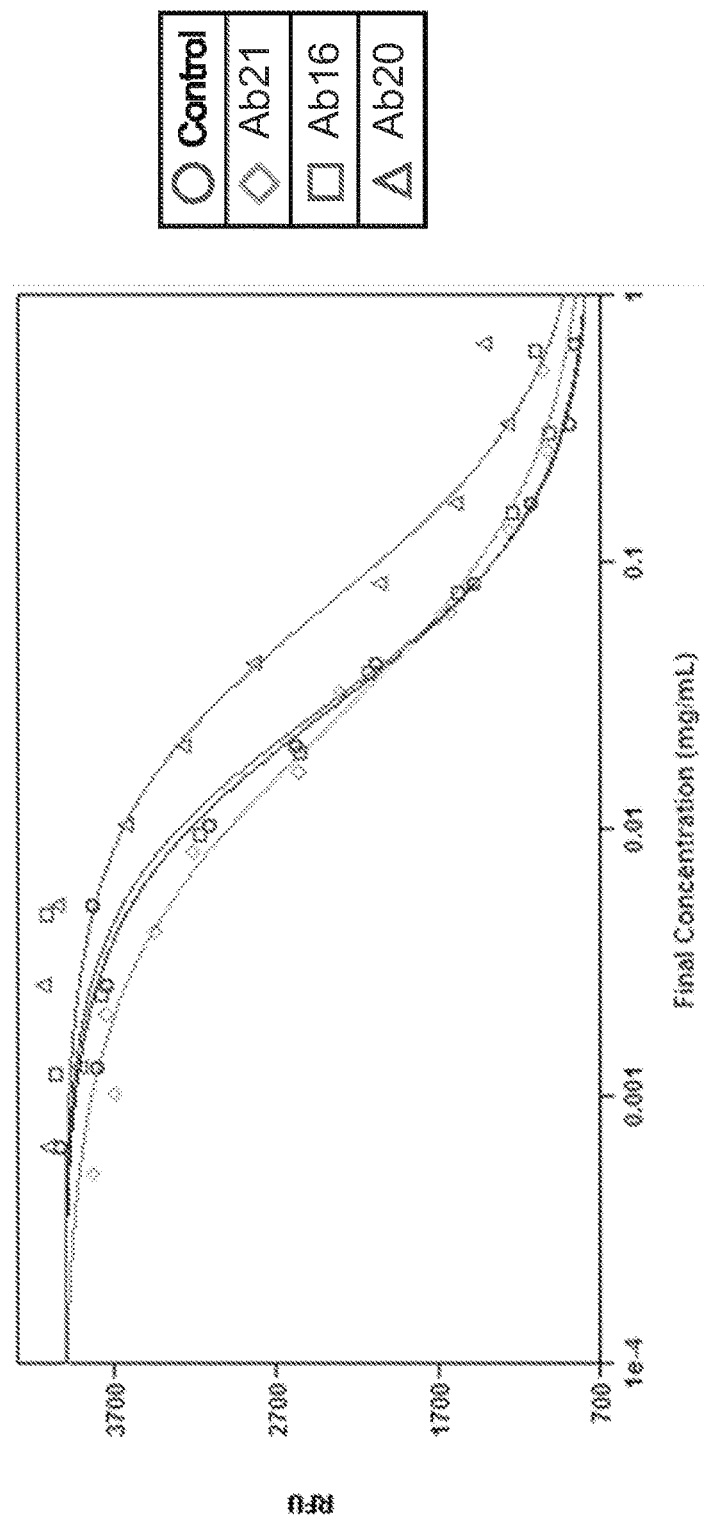
FIG. 7 is a graph depicting results from a CDC assay of a control anti-CD52 antibody and antibodies Ab21, Ab16, and Ab20.

Three anti-CD52 antibodies (Ab21, Ab20 and Ab16) were evaluated in a CDC assay. This assay was used to measure the ability of the antibodies to lyse Pfeiffer B-lymphocytes in the presence of complement. Antibodies were assayed in singlicate on the same plate and qualitatively compared to Ab26 (Control) (See, FIG. 7).

The results suggested that the potency of Ab21 and Ab16 was comparable to or improved over Ab26. Ab20 had slightly lower potency in this test.

Example 7

Biological Activity of Anti-CD52 Antibodies in HuCD52-Transgenic Mice

Figure 8:
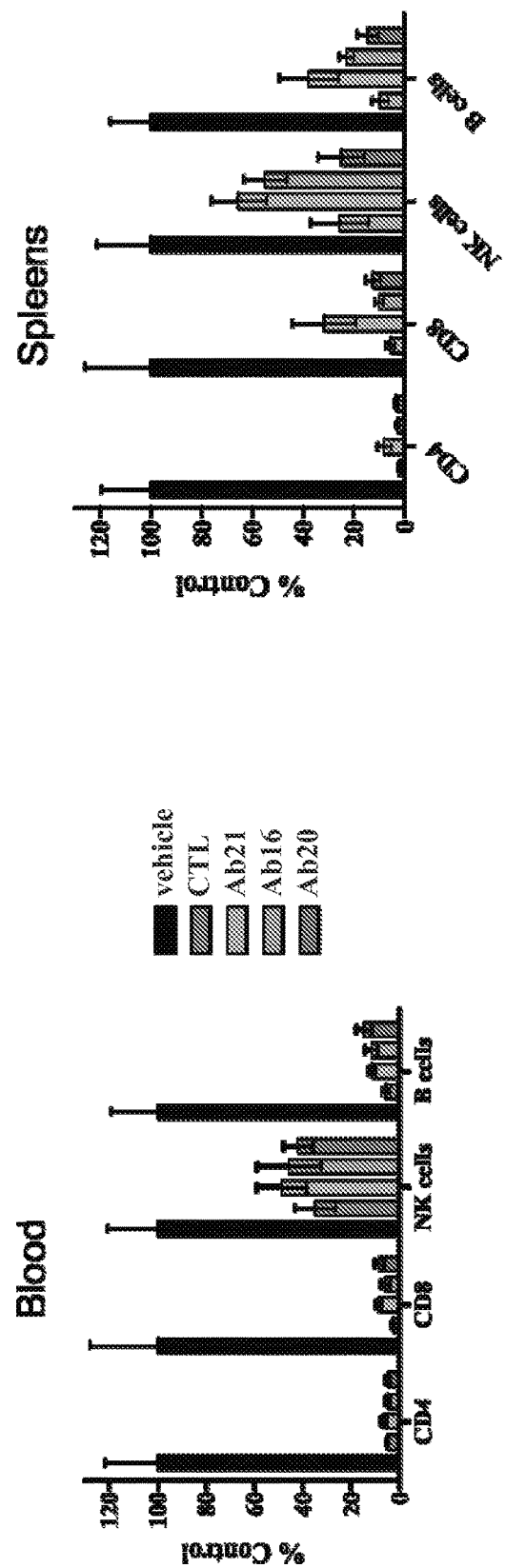
FIG. 8 depicts results of assays for CD52+ cell-depleting activity of a control anti-CD52 antibody (CTL) and antibodies Ab21, Ab16, and Ab20 in human CD52 transgenic mice. The graph on the left shows results from blood samples. The graph on the right shows results from spleen samples.

Three anti-CD52 antibodies (Ab21, Ab20 and Ab16) were also evaluated in vivo in huCD52 transgenic mice. HuCD52 transgenic mice were injected with Ab26, Ab21, Ab20 or Ab16 intravenously at 1 mg/kg (5 animals/group). On day 3 post-injection, blood and spleens were analyzed for lymphocyte depletion by flow cytometry. The extent of lymphocyte depletion in blood and spleen by flow cytometry analysis is shown in FIG. 8 (Ab26 is labeled as "CTL").

The results suggested that the lymphocyte depletion induced by antibodies Ab21, Ab20 and Ab16 in blood and spleens appeared to be similar to or improved over antibody Ab26. Taken together, these data confirm that these anti-CD52 antibodies are biologically active in vivo.

Table 7 lists the SEQ ID NOs used herein.

TABLE 7

SEQ ID NOs

| SEQ ID NO | TYPE | DESCRIPTION |
|---|---|---|
| 1 | Full-length protein | Wild-type CD52 protein |
| 2 | LC | KGN |
| 3 | HC | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN |
| 4 | LC | Ab26 |
| 5 | HC (nucleic acid) | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN |
| 6 | LC (nucleic acid) | Ab26 |
| 7 | H-CDR1 | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 |
| 8 | H-CDR2 | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 |
| 9 | H-CDR3 | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 |
| 10 | L-CDR1 | Ab26 |
| 11 | L-CDR1 | Ab1 |
| 12 | L-CDR1 | Ab2 |
| 13 | L-CDR1 | Ab3 |
| 14 | L-CDR1 | Ab4 |
| 15 | L-CDR1 | Ab5 |
| 16 | L-CDR1 | Ab6 |
| 17 | L-CDR1 | Ab7 |
| 18 | L-CDR1 | Ab10 |

TABLE 7-continued

SEQ ID NOs

| SEQ ID NO | TYPE | DESCRIPTION |
|---|---|---|
| 19 | L-CDR1 | Ab11 |
| 20 | L-CDR1 | Ab12 |
| 21 | L-CDR1 | Ab13 |
| 22 | L-CDR1 | Ab14 |
| 23 | L-CDR1 | Ab15 |
| 24 | L-CDR1 | Ab16 |
| 25 | L-CDR1 | Ab17 |
| 26 | L-CDR1 | Ab18 |
| 27 | L-CDR1 | Ab19 |
| 28 | L-CDR1 | Ab20 |
| 29 | L-CDR1 | Ab21 |
| 30 | L-CDR1 | Ab22 |
| 31 | L-CDR1 | Ab23 |
| 32 | L-CDR1 | Ab24 |
| 33 | L-CDR1 | Ab25 |
| 34 | L-CDR2 | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 |
| 35 | L-CDR3 | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, and Ab25 |
| 36 | LC | Ab1 |
| 37 | LC | Ab2 |
| 38 | LC | Ab3 |
| 39 | LC | Ab4 |
| 40 | LC | Ab5 |
| 41 | LC | Ab6 |
| 42 | LC | Ab7 |
| 43 | LC | Ab10 |
| 44 | LC | Ab11 |
| 45 | LC | Ab12 |
| 46 | LC | Ab13 |
| 47 | LC | Ab14 |
| 48 | LC | Ab15 |
| 49 | LC | Ab16 |
| 50 | LC | Ab17 |
| 51 | LC | Ab18 |
| 52 | LC | Ab19 |
| 53 | LC | Ab20 |
| 54 | LC | Ab21 |
| 55 | LC | Ab22 |
| 56 | LC | Ab23 |
| 57 | LC | Ab24 |
| 58 | LC | Ab25 |
| 59 | $V_H$ | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN |
| 60 | $V_L$ | Ab26 |
| 61 | $V_L$ | Ab1 |
| 62 | $V_L$ | Ab2 |
| 63 | $V_L$ | Ab3 |
| 64 | $V_L$ | Ab4 |
| 65 | $V_L$ | Ab5 |
| 66 | $V_L$ | Ab6 |
| 67 | $V_L$ | Ab7 |
| 68 | $V_L$ | Ab10 |
| 69 | $V_L$ | Ab11 |
| 70 | $V_L$ | Ab12 |
| 71 | $V_L$ | Ab13 |
| 72 | $V_L$ | Ab14 |
| 73 | $V_L$ | Ab15 |
| 74 | $V_L$ | Ab16 |
| 75 | $V_L$ | Ab17 |
| 76 | $V_L$ | Ab18 |
| 77 | $V_L$ | Ab19 |
| 78 | $V_L$ | Ab20 |
| 79 | $V_L$ | Ab21 |
| 80 | $V_L$ | Ab22 |
| 81 | $V_L$ | Ab23 |
| 82 | $V_L$ | Ab24 |
| 83 | $V_L$ | Ab25 |
| 84 | $V_H$ (nucleic acid) | Ab26, Ab1, Ab2, Ab3, Ab4, Ab5, Ab6, Ab7, Ab10, Ab11, Ab12, Ab13, Ab14, Ab15, Ab16, Ab17, Ab18, Ab19, Ab20, Ab21, Ab22, Ab23, Ab24, Ab25, and KGN |
| 85 | $V_L$ (nucleic acid) | Ab26 |
| 86 | L-CDR1 | KSSQSLLYSNXKTYLN, wherein X is not glycine. |
| 87 | Peptide | CD52 peptide mimotope. |
| 88 | $V_L$ (nucleic acid) | Ab1 |
| 89 | $V_L$ (nucleic acid) | Ab2 |
| 90 | $V_L$ (nucleic acid) | Ab3 |
| 91 | $V_L$ (nucleic acid) | Ab4 |
| 92 | $V_L$ (nucleic acid) | Ab5 |
| 93 | $V_L$ (nucleic acid) | Ab6 |
| 94 | $V_L$ (nucleic acid) | Ab7 |
| 95 | $V_L$ (nucleic acid) | Ab10 |
| 96 | $V_L$ (nucleic acid) | Ab11 |
| 97 | $V_L$ (nucleic acid) | Ab12 |
| 98 | $V_L$ (nucleic acid) | Ab13 |
| 99 | $V_L$ (nucleic acid) | Ab14 |
| 100 | $V_L$ (nucleic acid) | Ab15 |
| 101 | $V_L$ (nucleic acid) | Ab16 |
| 102 | $V_L$ (nucleic acid) | Ab17 |
| 103 | $V_L$ (nucleic acid) | Ab18 |
| 104 | $V_L$ (nucleic acid) | Ab19 |
| 105 | $V_L$ (nucleic acid) | Ab20 |
| 106 | $V_L$ (nucleic acid) | Ab21 |
| 107 | $V_L$ (nucleic acid) | Ab22 |
| 108 | $V_L$ (nucleic acid) | Ab23 |
| 109 | $V_L$ (nucleic acid) | Ab24 |
| 110 | $V_L$ (nucleic acid) | Ab25 |
| 111 | $V_L$ (nucleic acid) | KGN |
| 112 | LC (nucleic acid) | Ab1 |
| 113 | LC (nucleic acid) | Ab2 |
| 114 | LC (nucleic acid) | Ab3 |
| 115 | LC (nucleic acid) | Ab4 |
| 116 | LC (nucleic acid) | Ab5 |
| 117 | LC (nucleic acid) | Ab6 |
| 118 | LC (nucleic acid) | Ab7 |
| 119 | LC (nucleic acid) | Ab10 |
| 120 | LC (nucleic acid) | Ab11 |
| 121 | LC (nucleic acid) | Ab12 |
| 122 | LC (nucleic acid) | Ab13 |
| 123 | LC (nucleic acid) | Ab14 |
| 124 | LC (nucleic acid) | Ab15 |
| 125 | LC (nucleic acid) | Ab16 |
| 126 | LC (nucleic acid) | Ab17 |
| 127 | LC (nucleic acid) | Ab18 |
| 128 | LC (nucleic acid) | Ab19 |
| 129 | LC (nucleic acid) | Ab20 |
| 130 | LC (nucleic acid) | Ab21 |
| 131 | LC (nucleic acid) | Ab22 |
| 132 | LC (nucleic acid) | Ab23 |
| 133 | LC (nucleic acid) | Ab24 |
| 134 | LC (nucleic acid) | Ab25 |
| 135 | LC (nucleic acid) | KGN |

What is claimed is:

1. An anti-human CD52 antibody or an antigen-binding fragment thereof, wherein said antibody comprises a heavy chain variable region and a light chain variable region,
   wherein said heavy chain variable region comprises the heavy chain CDR1-CDR3 amino acid sequences of SEQ ID NOs: 7-9, respectively, and
   wherein said light chain variable region comprises the light chain CDR1-CDR3 amino acid sequences of SEQ ID NO: 86, SEQ ID NO: 34, and SEQ ID NO: 35, respectively;
   wherein residue 11 in SEQ ID NO: 86 is K, R, Q, H, S, Y, A, D, E, F, I, L, M, N, T, or V.

2. The antibody or fragment according to claim 1, wherein said antibody or fragment demonstrates increased stability relative to an antibody comprising the heavy chain amino acid sequence of SEQ ID NO: 3 without the signal sequence and the light chain amino acid sequence of SEQ ID NO: 4 without the signal sequence.

3. The antibody or fragment according to claim 1, wherein residue 11 in SEQ ID NO: 86 is: (a) K (SEQ ID NO: 24); (b) R (SEQ ID NO: 29); or (c) Q (SEQ ID NO: 28).

4. The antibody or fragment according to claim 1, wherein:
   (a) said heavy chain variable region comprises SEQ ID NO: 59;
   (b) said light chain variable region comprises a sequence selected from the group consisting of SEQ ID NOs: 68-83; or
   (c) said heavy chain variable region comprises SEQ ID NO: 59 and said light chain variable region comprises a sequence selected from the group consisting of SEQ ID NOs: 68-83.

5. The antibody according to claim 1, comprising:
   (a) a heavy chain of SEQ ID NO: 3 without the signal sequence;
   (b) a light chain selected from the group consisting of SEQ ID NOs: 43-58; or
   (c) a heavy chain of SEQ ID NO: 3 without the signal sequence and a light chain selected from the group consisting of SEQ ID NOs: 43-58.

6. An antibody comprising:
   (a) a heavy chain amino acid sequence of SEQ ID NO: 3 without the signal sequence and a light chain amino acid sequence of SEQ ID NO: 49;
   (b) a heavy chain amino acid sequence of SEQ ID NO: 3 without the signal sequence and a light chain amino acid sequence of SEQ ID NO: 53; or
   (c) a heavy chain amino acid sequence of SEQ ID NO: 3 without the signal sequence and a light chain amino acid sequence of SEQ ID NO: 54.

7. The antibody according to claim 1 that is an immunoglobulin G (IgG).

8. The fragment according to claim 1, wherein said fragment is selected from the group consisting of an scFv fragment, an Fab fragment, an Fv fragment, an F(ab')$_2$ fragment, a minibody, a diabody, a triabody, and a tetrabody.

9. The antibody or fragment according to claim 4, wherein said antibody comprises a human IgG1, IgG2, IgG3, or IgG4 Fc region.

10. The antibody or fragment according to claim 6, wherein the heavy chain C-terminal lysine is cleaved.

11. An isolated nucleic acid molecule comprising a nucleotide sequence that encodes the light chain or an antigen-binding fragment thereof, or both the heavy chain or an antigen-binding portion fragment thereof and the light chain or an antigen-binding fragment thereof, of the antibody or fragment according to claim 1.

12. A recombinant expression vector comprising the nucleic acid molecule of claim 11.

13. An isolated host cell comprising the vector according to claim 12.

14. An isolated cell line that produces the antibody or fragment according to claim 1 or the light chain of the antibody or fragment.

15. A method of making an anti-human CD52 antibody or an antigen-binding fragment thereof, comprising (1) maintaining a cell comprising a nucleotide sequence encoding the heavy chain or an antigen-binding fragment thereof, and a nucleotide sequence encoding the light chain or an antigen-binding fragment thereof, of the antibody or fragment according to claim 1 under conditions appropriate for expression of the antibody or fragment; and (2) recovering the antibody or fragment.

16. A composition comprising the antibody or antigen-binding fragment according to claim 1 and a pharmaceutically acceptable vehicle or carrier.

17. A method for targeting CD52$^+$ cells in a human patient in need thereof, comprising administering to the patient an effective amount of the antibody or antigen-binding fragment according to claim 1.

18. The method of claim 17, wherein the patient has an autoimmune disease.

19. The method according to claim 18, wherein said autoimmune disease is multiple sclerosis.

20. The method according to claim 17, wherein the patient has cancer.

21. The method according to claim 20, wherein the cancer is chronic lymphocytic leukemia.

22. The method according to claim 17, wherein the patient is in need of inhibition of angiogenesis.

23. A method of inducing immunosuppression in a patient in need thereof, comprising administering to the patient an effective amount of the antibody or antigen-binding fragment according to claim 1.

24. A method for targeting CD52$^+$ cells in a human patient in need thereof, comprising administering to the patient an effective amount of the antibody or antigen-binding fragment according to claim 3.

25. The method of claim 24, wherein the patient has an autoimmune disease.

26. The method according to claim 25, wherein said autoimmune disease is multiple sclerosis.

27. The method according to claim 24, wherein the patient has cancer.

28. The method according to claim 27, wherein the cancer is chronic lymphocytic leukemia.

29. The method according to claim 24, wherein the patient is in need of inhibition of angiogenesis.

30. A method of inducing immunosuppression in a patient in need thereof, comprising administering to the patient an effective amount of the antibody or antigen-binding fragment according to claim 3.

31. The antibody or fragment according to claim 1, wherein said heavy chain variable region comprises SEQ ID NO: 59 and said light chain variable region comprises SEQ ID NO: 74, 78, or 79.

32. A method for targeting $CD52^+$ cells in a human patient in need thereof, comprising administering to the patient an effective amount of the antibody or antigen-binding fragment according to claim 31.

33. The method of claim 32, wherein the patient has an autoimmune disease.

34. The method according to claim 33, wherein said autoimmune disease is multiple sclerosis.

35. The method according to claim 32, wherein the patient has cancer.

36. The method according to claim 35, wherein the cancer is chronic lymphocytic leukemia.

37. The method according to claim 32, wherein the patient is in need of inhibition of angiogenesis.

38. A method of inducing immunosuppression in a patient in need thereof, comprising administering to the patient an effective amount of the antibody or antigen-binding fragment according to claim 31.

39. A method for targeting $CD52^+$ cells in a human patient in need thereof, comprising administering to the patient an effective amount of the antibody according to claim 6.

40. The method of claim 39, wherein the patient has an autoimmune disease.

41. The method according to claim 40, wherein said autoimmune disease is multiple sclerosis.

42. The method according to claim 39, wherein the patient has cancer.

43. The method according to claim 42, wherein the cancer is chronic lymphocytic leukemia.

44. The method according to claim 39, wherein the patient is in need of inhibition of angiogenesis.

45. A method of inducing immunosuppression in a patient in need thereof, comprising administering to the patient an effective amount of the antibody according to claim 6.

* * * * *

SEQUENCE LISTING

<160> NUMBER OF SEQ ID NOS: 136

<210> SEQ ID NO 1
<211> LENGTH: 61
<212> TYPE: PRT
<213> ORGANISM: Homo sapiens

<400> SEQUENCE: 1

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Met Ser Gly Gly Ile Phe Leu Phe
        35                  40                  45

Phe Val Ala Asn Ala Ile Ile His Leu Phe Cys Phe Ser
    50                  55                  60

<210> SEQ ID NO 2
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Lys Gly Asn Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 464

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

Met Glu Ala Pro Ala Gln Leu Leu Phe Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Pro
        35                  40                  45

Phe Ser Asn Tyr Trp Met Asn Trp Val Arg Gln Ala Pro Gly Lys Gly
50                  55                  60

Leu Glu Trp Val Gly Gln Ile Arg Leu Lys Ser Asn Asn Tyr Ala Thr
65                  70                  75                  80

His Tyr Ala Glu Ser Val Lys Gly Arg Phe Thr Ile Ser Arg Asp Asp
                85                  90                  95

Ser Lys Asn Ser Leu Tyr Leu Gln Met Asn Ser Leu Lys Thr Glu Asp
            100                 105                 110

Thr Ala Val Tyr Tyr Cys Thr Pro Ile Asp Tyr Trp Gly Gln Gly Thr
        115                 120                 125

Thr Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys

```
                    370                 375                 380
Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
                450                 455                 460

<210> SEQ ID NO 4
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Met Glu Ala Pro Ala Gln Leu Leu Phe Leu Leu Leu Leu Trp Leu Pro
1               5                   10                  15

Asp Thr Thr Gly Asp Ile Val Met Thr Gln Thr Pro Leu Ser Leu Ser
                20                  25                  30

Val Thr Pro Gly Gln Pro Ala Ser Ile Ser Cys Lys Ser Ser Gln Ser
                35                  40                  45

Leu Leu Tyr Ser Asn Gly Lys Thr Tyr Leu Asn Trp Val Leu Gln Lys
    50                  55                  60

Pro Gly Gln Ser Pro Gln Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
                100                 105                 110

Cys Val Gln Gly Ser His Phe His Thr Phe Gly Gln Gly Thr Lys Leu
                115                 120                 125

Glu Ile Lys Arg Thr Val Ala Ala Pro Ser Val Phe Ile Phe Pro Pro
                130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
                210                 215                 220

Leu Ser Ser Pro Val Thr Lys Ser Phe Asn Arg Gly Glu Cys
225                 230                 235

<210> SEQ ID NO 5
<211> LENGTH: 1404
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 5
cccaccatgg aagccccagc gcagcttctc ttcctcctgc tactctggct ccctgatacc    60
accggagagg tacagctggt ggagtcggga ggaggcttgg tacagcctgg gggttctctg   120
agactctcct gtgcagcttc tggattccca ttcagtaact actggatgaa ctgggtccgc   180
caggctccag ggaagggact gagtgggtg gtcaaatta gattgaaatc taataattat   240
gcaacacatt atgcggagtc tgtgaaaggg cggttcacca tctccagaga tgattccaaa   300
aacagcctct atcttcaaat gaattccctg aaaactgaag acactgccgt ttattactgt   360
accccaattg actattgggg ccaaggcacc actgtcacag tctcctcagc tccaccaag    420
ggcccatcgg tcttcccct ggcaccctcc tccaagagca cctctggggg tacagcggcc    480
ctgggctgcc tggtcaagga ctacttcccc gaaccggtga cggtgtcgtg aactcaggc    540
gccctgacca gcggcgtgca caccttcccg gctgtcctac agtcctcagg actctactcc   600
ctcagcagcg tggtgaccgt gccctccagc agcttgggca cccagaccta catctgcaac   660
gtgaatcaca agcccagcaa caccaaggtg gacaagaaag ttgagcccaa atcttgtgac   720
aaaactcaca catgcccacc gtgcccagca cctgaactcc tggggggacc gtcagtcttc   780
ctcttccccc caaaacccaa ggacaccctc atgatctccc ggacccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaaaggg  1080
cagccccgag aaccacaggt gtacaccctg cccccatccc gggatgagct gaccaagaac  1140
caggtcagcc tgacatgcct ggtcaaaggc ttctatccca gcgacatcgc cgtggagtgg  1200
gagagcaatg ggcagccgga gaacaactac aagaccacgc ctcccgtgct ggactccgac  1260
ggctccttct tcctctacag caagctcacc gtggacaagt ccaggtggca gcaggggaac  1320
gtcttctcat gctccgtgat gcatgaggct ctgcacaacc actacacgca gaagagcctc  1380
tccctgtctc cgggtaaatg atga                                         1404

<210> SEQ ID NO 6
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
cccaccatgg aagccccagc gcagcttctc ttcctcctgc tactctggct ccctgatacc    60
accggagaca ttgtgatgac ccagactcca ctcagtttgt cagttacccc tgggcaacca   120
gcctctatct cttgcaagtc aagtcagagc ctcttatata gtaatggaaa aacctatttg   180
aactgggttt tacagaagcc aggccagtct ccacagcgcc taatctatct ggtgtctaaa   240
ctggactctg gagtccctga caggttctct ggcagtggat caggaacaga ttttacactg   300
aaaatcagca gagtggaggc tgaggatgtg ggagtttatt actgcgtgca aggttcacat   360

```
tttcacacgt tcggtcaagg gaccaagctg gagattaaac gaactgtggc agcaccaagc    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tagtga                                                               726
```

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Phe Pro Phe Ser Asn Tyr Trp Met Asn
1               5                   10

<210> SEQ ID NO 8
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Ile Arg Leu Lys Ser Asn Asn Tyr Ala Thr His Tyr Ala Glu Ser
1               5                   10                  15

Val Lys Gly

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Thr Pro Ile Asp Tyr
1               5

<210> SEQ ID NO 10
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Lys Ser Ser Gln Ser Leu Leu Tyr Ser Asn Gly Lys Thr Tyr Leu Asn
1               5                   10                  15

<210> SEQ ID NO 11
<211> LENGTH: 16

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Lys Ser Ser Gln Ser Leu Leu Tyr Ser Asp Gly Lys Thr Tyr Leu Asn
1               5                   10                  15

<210> SEQ ID NO 12
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Lys Ser Ser Gln Ser Leu Leu Tyr Ser His Gly Lys Thr Tyr Leu Asn
1               5                   10                  15

<210> SEQ ID NO 13
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Lys Ser Ser Gln Ser Leu Leu Tyr Ser Lys Gly Lys Thr Tyr Leu Asn
1               5                   10                  15

<210> SEQ ID NO 14
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Lys Ser Ser Gln Ser Leu Leu Tyr Ser Gln Gly Lys Thr Tyr Leu Asn
1               5                   10                  15

<210> SEQ ID NO 15
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Lys Ser Ser Gln Ser Leu Leu Tyr Ser Arg Gly Lys Thr Tyr Leu Asn
1               5                   10                  15

<210> SEQ ID NO 16
<211> LENGTH: 16
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 16

Lys Ser Ser Gln Ser Leu Leu Tyr Ser Thr Gly Lys Thr Tyr Leu Asn
1               5                   10                  15

<210> SEQ ID NO 17
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Lys Ser Ser Gln Ser Leu Leu Tyr Ser Tyr Gly Lys Thr Tyr Leu Asn
1               5                   10                  15

<210> SEQ ID NO 18
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Lys Ser Ser Gln Ser Leu Leu Tyr Ser Asn Ala Lys Thr Tyr Leu Asn
1               5                   10                  15

<210> SEQ ID NO 19
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Lys Ser Ser Gln Ser Leu Leu Tyr Ser Asn Asp Lys Thr Tyr Leu Asn
1               5                   10                  15

<210> SEQ ID NO 20
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Lys Ser Ser Gln Ser Leu Leu Tyr Ser Asn Glu Lys Thr Tyr Leu Asn
1               5                   10                  15

<210> SEQ ID NO 21
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21
```

Lys Ser Ser Gln Ser Leu Leu Tyr Ser Asn Phe Lys Thr Tyr Leu Asn
1               5                   10                  15

<210> SEQ ID NO 22
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Lys Ser Ser Gln Ser Leu Leu Tyr Ser Asn His Lys Thr Tyr Leu Asn
1               5                   10                  15

<210> SEQ ID NO 23
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Lys Ser Ser Gln Ser Leu Leu Tyr Ser Asn Ile Lys Thr Tyr Leu Asn
1               5                   10                  15

<210> SEQ ID NO 24
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Lys Ser Ser Gln Ser Leu Leu Tyr Ser Asn Lys Lys Thr Tyr Leu Asn
1               5                   10                  15

<210> SEQ ID NO 25
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Lys Ser Ser Gln Ser Leu Leu Tyr Ser Asn Leu Lys Thr Tyr Leu Asn
1               5                   10                  15

<210> SEQ ID NO 26
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Lys Ser Ser Gln Ser Leu Leu Tyr Ser Asn Met Lys Thr Tyr Leu Asn
1               5                   10                  15

```
<210> SEQ ID NO 27
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Lys Ser Ser Gln Ser Leu Leu Tyr Ser Asn Asn Lys Thr Tyr Leu Asn
1               5                   10                  15

<210> SEQ ID NO 28
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Lys Ser Ser Gln Ser Leu Leu Tyr Ser Asn Gln Lys Thr Tyr Leu Asn
1               5                   10                  15

<210> SEQ ID NO 29
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Lys Ser Ser Gln Ser Leu Leu Tyr Ser Asn Arg Lys Thr Tyr Leu Asn
1               5                   10                  15

<210> SEQ ID NO 30
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Lys Ser Ser Gln Ser Leu Leu Tyr Ser Asn Ser Lys Thr Tyr Leu Asn
1               5                   10                  15

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Lys Ser Ser Gln Ser Leu Leu Tyr Ser Asn Thr Lys Thr Tyr Leu Asn
1               5                   10                  15

<210> SEQ ID NO 32
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Lys Ser Ser Gln Ser Leu Leu Tyr Ser Asn Val Lys Thr Tyr Leu Asn
1               5                   10                  15

<210> SEQ ID NO 33
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Lys Ser Ser Gln Ser Leu Leu Tyr Ser Asn Tyr Lys Thr Tyr Leu Asn
1               5                   10                  15

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Leu Val Ser Lys Leu Asp Ser
1               5

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Val Gln Gly Ser His Phe His Thr
1               5

<210> SEQ ID NO 36
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 37
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

His Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 38
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Lys Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 39
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Gln Gly Lys Thr Tyr Leu Asn Trp Val Leu Gln Lys Pro Gly Gln Ser

```
            35                  40                  45
Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 40
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
                 20                  25                  30

Arg Gly Lys Thr Tyr Leu Asn Trp Val Leu Gln Lys Pro Gly Gln Ser
            35                  40                  45

Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 41
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Thr Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 42
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

```
Asp Ile Val Met Thr Gln Thr Pro Leu Ser Leu Ser Val Thr Pro Gly
1               5                   10                  15
```

```
Gln Pro Ala Ser Ile Ser Cys Lys Ser Ser Gln Ser Leu Leu Tyr Ser
            20                  25                  30

Tyr Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 43
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Ala Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
```

```
                145                 150                 155                 160
Gly Asn Ser Gln Glu Ser Val Thr Glu Gln Asp Ser Lys Asp Ser Thr
                    165                 170                 175
Tyr Ser Leu Ser Ser Thr Leu Thr Leu Ser Lys Ala Asp Tyr Glu Lys
                180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys
        210                 215

<210> SEQ ID NO 44
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu Tyr Ser
            20                  25                  30
Asn Asp Lys Thr Tyr Leu Asn Trp Val Leu Gln Lys Pro Gly Gln Ser
        35                  40                  45
Pro Gln Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Val Gln Gly
                85                  90                  95
Ser His Phe His Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 45
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45
```

-continued

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Glu Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 46
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Phe Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

-continued

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 47
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn His Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 48
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Ile Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 49
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Lys Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110
```

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 50
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Leu Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Ser Asp Glu Gln
        115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 51
<211> LENGTH: 218

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Met Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Asn Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly

```
Ser His Phe His Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 53
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gln Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 54
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 54

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Arg Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 55
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 55

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Ser Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 56
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
             20                  25                  30

Asn Thr Lys Thr Tyr Leu Asn Trp Val Leu Gln Lys Pro Gly Gln Ser
         35                  40                  45

Pro Gln Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
```

Val Thr Lys Ser Phe Asn Arg Gly Glu Cys
    210                 215

<210> SEQ ID NO 57
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Val Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 58
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Tyr Lys Thr Tyr Leu Asn Trp Val Leu Gln Lys Pro Gly Gln Ser
        35                  40                  45

```
Pro Gln Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Val Gln Gly
                 85                  90                  95
Ser His Phe His Thr Phe Gly Gln Gly Thr Lys Leu Glu Ile Lys Arg
                100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 59
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Pro Phe Ser Asn Tyr
             20                  25                  30
Trp Met Asn Trp Val Arg Gln Ala Pro Gly Lys Gly Leu Glu Trp Val
         35                  40                  45
Gly Gln Ile Arg Leu Lys Ser Asn Asn Tyr Ala Thr His Tyr Ala Glu
     50                  55                  60
Ser Val Lys Gly Arg Phe Thr Ile Ser Arg Asp Asp Ser Lys Asn Ser
 65                  70                  75                  80
Leu Tyr Leu Gln Met Asn Ser Leu Lys Thr Glu Asp Thr Ala Val Tyr
                 85                  90                  95
Tyr Cys Thr Pro Ile Asp Tyr Trp Gly Gln Gly Thr Thr Val Thr Val
                100                 105                 110
Ser Ser

<210> SEQ ID NO 60
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 60

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 61
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 62
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

His Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys
            100                 105                 110
```

<210> SEQ ID NO 63
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

```
Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
                 20                  25                  30

Lys Gly Lys Thr Tyr Leu Asn Trp Val Leu Gln Lys Pro Gly Gln Ser
             35                  40                  45

Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys
            100                 105                 110
```

<210> SEQ ID NO 64
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
                 20                  25                  30

Gln Gly Lys Thr Tyr Leu Asn Trp Val Leu Gln Lys Pro Gly Gln Ser
             35                  40                  45

Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Ser His Phe His Thr Phe Gly Gln Gly Thr Lys Leu Glu Ile Lys
            100                 105                 110
```

<210> SEQ ID NO 65
<211> LENGTH: 111

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 66
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Thr Gly Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 67
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser

```
                20                  25                  30

Tyr Gly Lys Thr Tyr Leu Asn Trp Val Leu Gln Lys Pro Gly Gln Ser
            35                  40                  45

Pro Gln Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 68
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
            20                  25                  30

Asn Ala Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 69
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ser
            20                  25                  30

Asn Asp Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Val Gln Gly
                85                  90                  95
```

Ser His Phe His Thr Phe Gly Gln Gly Thr Lys Leu Glu Ile Lys
            100                 105                 110

<210> SEQ ID NO 70
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Glu Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 71
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Phe Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 72
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn His Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 73
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Ile Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 74
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Lys Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                     85                  90                  95

Ser His Phe His Thr Phe Gly Gln Gly Thr Lys Leu Glu Ile Lys
                    100                 105                 110

<210> SEQ ID NO 75
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu Tyr Ser
                 20                  25                  30

Asn Leu Lys Thr Tyr Leu Asn Trp Val Leu Gln Lys Pro Gly Gln Ser
             35                  40                  45

Pro Gln Arg Leu Ile Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                     85                  90                  95

Ser His Phe His Thr Phe Gly Gln Gly Thr Lys Leu Glu Ile Lys
                    100                 105                 110

<210> SEQ ID NO 76
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu Tyr Ser
                 20                  25                  30

Asn Met Lys Thr Tyr Leu Asn Trp Val Leu Gln Lys Pro Gly Gln Ser
             35                  40                  45

Pro Gln Arg Leu Ile Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                     85                  90                  95

Ser His Phe His Thr Phe Gly Gln Gly Thr Lys Leu Glu Ile Lys
                    100                 105                 110

<210> SEQ ID NO 77
```

<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Asn Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 78
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gln Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 79
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 79

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Arg Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 80
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Ser Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110

<210> SEQ ID NO 81
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Thr Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly

```
                    85                  90                  95
Ser His Phe His Thr Phe Gly Gln Gly Thr Lys Leu Glu Ile Lys
            100                 105                 110
```

<210> SEQ ID NO 82
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Val Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110
```

<210> SEQ ID NO 83
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Tyr Lys Thr Tyr Leu Asn Trp Val Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Ser His Phe His Thr Phe Gly Gln Gly Thr Lys Leu Glu Ile Lys
            100                 105                 110
```

<210> SEQ ID NO 84
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:

```
Synthetic polynucleotide"

<400> SEQUENCE: 84
gaggtacagc tggtggagtc gggaggaggc ttggtacagc ctgggggttc tctgagactc    60
tcctgtgcag cttctggatt cccattcagt aactactgga tgaactgggt ccgccaggct   120
ccagggaagg gacttgagtg ggtgggtcaa attagattga aatctaataa ttatgcaaca   180
cattatgcgg agtctgtgaa agggcggttc accatctcca gagatgattc caaaaacagc   240
ctctatcttc aaatgaattc cctgaaaact gaagacactg ccgtttatta ctgtacccca   300
attgactatt ggggccaagg caccactgtc acagtctcct ca                      342

<210> SEQ ID NO 85
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
gacattgtga tgacccagac tccactcagt ttgtcagtta cccctgggca accagcctct    60
atctcttgca gtcaagtca gagcctctta tatagtaatg gaaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333

<210> SEQ ID NO 86
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Any amino acid except Gly

<400> SEQUENCE: 86

Lys Ser Ser Gln Ser Leu Leu Tyr Ser Asn Xaa Lys Thr Tyr Leu Asn
1               5                   10                  15

<210> SEQ ID NO 87
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Cys Gly Gln Asn Asp Thr Ser Gln Thr Ser Ser Pro Ser Ala Asp
1               5                   10                  15

<210> SEQ ID NO 88
<211> LENGTH: 333
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 88
gacattgtga tgacccagac tccactcagt ttgtcagtta ccctgggca accagcctct      60 atctcttgca agtcaagtca gagcctctta tatagtgatg gaaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 89
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 89
gacattgtga tgacccagac tccactcagt ttgtcagtta ccctgggca accagcctct      60 atctcttgca agtcaagtca gagcctctta tatagtcacg gaaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 90
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 90
gacattgtga tgacccagac tccactcagt ttgtcagtta ccctgggca accagcctct      60 atctcttgca agtcaagtca gagcctctta tatagtaaag gaaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 91
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
```

```
gacattgtga tgacccagac tccactcagt ttgtcagtta ccctgggca accagcctct    60 atctcttgca agtcaagtca gagcctctta tatagtcaag gaaaaaccta tttgaactgg   120
gttttacaga agccaggcca gtctccacag cgcctaatct atctggtgtc taaactggac  180
tctggagtcc ctgacaggtt ctctggcagt ggatcaggaa cagattttac actgaaaatc  240
agcagagtgg aggctgagga tgtgggagtt tattactgcg tgcaaggttc acattttcac  300
acgttcggtc aagggaccaa gctggagatt aaa                               333
```

<210> SEQ ID NO 92
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
gacattgtga tgacccagac tccactcagt ttgtcagtta ccctgggca accagcctct    60 atctcttgca agtcaagtca gagcctctta tatagtcgcg gaaaaaccta tttgaactgg   120
gttttacaga agccaggcca gtctccacag cgcctaatct atctggtgtc taaactggac  180
tctggagtcc ctgacaggtt ctctggcagt ggatcaggaa cagattttac actgaaaatc  240
agcagagtgg aggctgagga tgtgggagtt tattactgcg tgcaaggttc acattttcac  300
acgttcggtc aagggaccaa gctggagatt aaa                               333
```

<210> SEQ ID NO 93
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
gacattgtga tgacccagac tccactcagt ttgtcagtta ccctgggca accagcctct    60 atctcttgca agtcaagtca gagcctctta tatagtaccg gaaaaaccta tttgaactgg   120
gttttacaga agccaggcca gtctccacag cgcctaatct atctggtgtc taaactggac  180
tctggagtcc ctgacaggtt ctctggcagt ggatcaggaa cagattttac actgaaaatc  240
agcagagtgg aggctgagga tgtgggagtt tattactgcg tgcaaggttc acattttcac  300
acgttcggtc aagggaccaa gctggagatt aaa                               333
```

<210> SEQ ID NO 94
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 94

```
gacattgtga tgacccagac tccactcagt ttgtcagtta ccctgggca accagcctct    60 atctcttgca agtcaagtca gagcctctta tatagttatg gaaaaaccta tttgaactgg   120
gttttacaga agccaggcca gtctccacag cgcctaatct atctggtgtc taaactggac  180
tctggagtcc ctgacaggtt ctctggcagt ggatcaggaa cagattttac actgaaaatc  240
```

```
agcagagtgg aggctgagga tgtgggagtt tattactgcg tgcaaggttc acattttcac    300
acgttcggtc aagggaccaa gctggagatt aaa                                 333

<210> SEQ ID NO 95
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
gacattgtga tgacccagac tccactcagt ttgtcagtta cccctgggca accagcctct    60
atctcttgca agtcaagtca gagcctctta tatagtaatg caaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 96
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
gacattgtga tgacccagac tccactcagt ttgtcagtta cccctgggca accagcctct    60
atctcttgca agtcaagtca gagcctctta tatagtaatg ataaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 97
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
gacattgtga tgacccagac tccactcagt ttgtcagtta cccctgggca accagcctct    60
atctcttgca agtcaagtca gagcctctta tatagtaatg aaaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 98
```

```
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
gacattgtga tgacccagac tccactcagt ttgtcagtta ccoctgggca accagcctct    60 atctcttgca agtcaagtca gagcctctta tatagtaatt ttaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333

<210> SEQ ID NO 99
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
gacattgtga tgacccagac tccactcagt ttgtcagtta ccoctgggca accagcctct    60 atctcttgca agtcaagtca gagcctctta tatagtaatc ataaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333

<210> SEQ ID NO 100
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
gacattgtga tgacccagac tccactcagt ttgtcagtta ccoctgggca accagcctct    60 atctcttgca agtcaagtca gagcctctta tatagtaata ttaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333

<210> SEQ ID NO 101
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 101

```
gacattgtga tgacccagac tccactcagt ttgtcagtta cccctgggca accagcctct    60
atctcttgca agtcaagtca gagcctctta tatagtaata agaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333
```

<210> SEQ ID NO 102
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 102

```
gacattgtga tgacccagac tccactcagt ttgtcagtta cccctgggca accagcctct    60
atctcttgca agtcaagtca gagcctctta tatagtaatt tgaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333
```

<210> SEQ ID NO 103
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 103

```
gacattgtga tgacccagac tccactcagt ttgtcagtta cccctgggca accagcctct    60
atctcttgca agtcaagtca gagcctctta tatagtaatg ataaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333
```

<210> SEQ ID NO 104
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104

```
gacattgtga tgacccagac tccactcagt ttgtcagtta cccctgggca accagcctct    60
atctcttgca agtcaagtca gagcctctta tatagtaata ataaaaccta tttgaactgg   120
```

```
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 105
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105
gacattgtga tgacccagac tccactcagt ttgtcagtta ccctgggca accagcctct     60 atctcttgca gtcaagtca gagcctctta tatagtaatc agaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 106
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 106
gacattgtga tgacccagac tccactcagt ttgtcagtta ccctgggca accagcctct     60 atctcttgca gtcaagtca gagcctctta tatagtaatc gtaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333

<210> SEQ ID NO 107
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107
gacattgtga tgacccagac tccactcagt ttgtcagtta ccctgggca accagcctct     60 atctcttgca gtcaagtca gagcctctta tatagtaata gtaaaaccta tttgaactgg    120
gttttacaga agccaggcca gtctccacag cgcctaatct atctggtgtc taaactggac    180
tctggagtcc ctgacaggtt ctctggcagt ggatcaggaa cagattttac actgaaaatc    240
agcagagtgg aggctgagga tgtgggagtt tattactgcg tgcaaggttc acattttcac    300
acgttcggtc aagggaccaa gctggagatt aaa                                 333
```

<210> SEQ ID NO 108
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108

```
gacattgtga tgacccagac tccactcagt ttgtcagtta ccccctgggca accagcctct    60 atctcttgca agtcaagtca gagcctctta tatagtaata ccaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333
```

<210> SEQ ID NO 109
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109

```
gacattgtga tgacccagac tccactcagt ttgtcagtta ccccctgggca accagcctct    60 atctcttgca agtcaagtca gagcctctta tatagtaatt tgaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333
```

<210> SEQ ID NO 110
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110

```
gacattgtga tgacccagac tccactcagt ttgtcagtta ccccctgggca accagcctct    60 atctcttgca agtcaagtca gagcctctta tatagtaatg ttaaaaccta tttgaactgg   120
gttttacaga agccaggcca gtctccacag cgcctaatct atctggtgtc taaactggac   180
tctggagtcc ctgacaggtt ctctggcagt ggatcaggaa cagattttac actgaaaatc   240
agcagagtgg aggctgagga tgtgggagtt tattactgcg tgcaaggttc acattttcac   300
acgttcggtc aagggaccaa gctggagatt aaa                                333
```

<210> SEQ ID NO 111
<211> LENGTH: 333
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 111

| | | | | | |
|---|---|---|---|---|---|
| gacattgtga | tgacccagac | tccactcagt | ttgtcagtta | ccctgggca | accagcctct | 60 |
| atctcttgca | agtcaagtca | gagcctctta | tatagtaaag | gaaataccta | tttgaactgg | 120 |
| gttttacaga | agccaggcca | gtctccacag | cgcctaatct | atctggtgtc | taaactggac | 180 |
| tctggagtcc | ctgacaggtt | ctctggcagt | ggatcaggaa | cagattttac | actgaaaatc | 240 |
| agcagagtgg | aggctgagga | tgtgggagtt | tattactgcg | tgcaaggttc | acattttcac | 300 |
| acgttcggtc | aagggaccaa | gctggagatt | aaa | | | 333 |

<210> SEQ ID NO 112
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 112

| | | | | | |
|---|---|---|---|---|---|
| cccaccatgg | aagccccagc | gcagcttctc | ttcctcctgc | tactctggct | ccctgatacc | 60 |
| accggagaca | ttgtgatgac | ccagactcca | ctcagtttgt | cagttacccc | tgggcaacca | 120 |
| gcctctatct | cttgcaagtc | aagtcagagc | ctcttatata | gtgatggaaa | aacctatttg | 180 |
| aactgggttt | tacagaagcc | aggccagtct | ccacagcgcc | taatctatct | ggtgtctaaa | 240 |
| ctggactctg | gagtccctga | caggttctct | ggcagtggat | caggaacaga | ttttacactg | 300 |
| aaaatcagca | gagtggaggc | tgaggatgtg | ggagtttatt | actgcgtgca | aggttcacat | 360 |
| tttcacacgt | tcggtcaagg | gaccaagctg | gagattaaac | gaactgtggc | agcaccaagc | 420 |
| gtcttcatct | tcccgccatc | tgatgagcag | ttgaaatctg | gaactgcctc | tgttgtgtgc | 480 |
| ctgctgaata | acttctatcc | cagagaggcc | aaagtacagt | ggaaggtgga | taacgccctc | 540 |
| caatcgggta | actcccagga | gagtgtcaca | gagcaggaca | gcaaggacag | cacctacagc | 600 |
| ctcagcagca | ccctgacgct | gagcaaagca | gactacgaga | aacacaaagt | ctacgcctgc | 660 |
| gaagtcaccc | atcagggcct | gagctcgccc | gtcacaaaga | gcttcaacag | gggagagtgt | 720 |
| tagtga | | | | | | 726 |

<210> SEQ ID NO 113
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113

| | | | | | |
|---|---|---|---|---|---|
| cccaccatgg | aagccccagc | gcagcttctc | ttcctcctgc | tactctggct | ccctgatacc | 60 |
| accggagaca | ttgtgatgac | ccagactcca | ctcagtttgt | cagttacccc | tgggcaacca | 120 |
| gcctctatct | cttgcaagtc | aagtcagagc | ctcttatata | gtcacggaaa | aacctatttg | 180 |
| aactgggttt | tacagaagcc | aggccagtct | ccacagcgcc | taatctatct | ggtgtctaaa | 240 |
| ctggactctg | gagtccctga | caggttctct | ggcagtggat | caggaacaga | ttttacactg | 300 |
| aaaatcagca | gagtggaggc | tgaggatgtg | ggagtttatt | actgcgtgca | aggttcacat | 360 |

```
tttcacacgt tcggtcaagg gaccaagctg gagattaaac gaactgtggc agcaccaagc    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tagtga                                                              726

<210> SEQ ID NO 114
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
cccaccatgg aagccccagc gcagcttctc ttcctcctgc tactctggct ccctgatacc     60
accggagaca ttgtgatgac ccagactcca ctcagtttgt cagttacccc tgggcaacca    120
gcctctatct cttgcaagtc aagtcagagc ctcttatata gtaaaggaaa aacctatttg    180
aactgggttt tacagaagcc aggccagtct ccacagcgcc taatctatct ggtgtctaaa    240
ctggactctg gagtccctga caggttctct ggcagtggat caggaacaga ttttacactg    300
aaaatcagca gagtggaggc tgaggatgtg ggagtttatt actgcgtgca aggttcacat    360
tttcacacgt tcggtcaagg gaccaagctg gagattaaac gaactgtggc agcaccaagc    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tagtga                                                              726

<210> SEQ ID NO 115
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115
cccaccatgg aagccccagc gcagcttctc ttcctcctgc tactctggct ccctgatacc     60
accggagaca ttgtgatgac ccagactcca ctcagtttgt cagttacccc tgggcaacca    120
gcctctatct cttgcaagtc aagtcagagc ctcttatata gtcaaggaaa aacctatttg    180
aactgggttt tacagaagcc aggccagtct ccacagcgcc taatctatct ggtgtctaaa    240
ctggactctg gagtccctga caggttctct ggcagtggat caggaacaga ttttacactg    300
aaaatcagca gagtggaggc tgaggatgtg ggagtttatt actgcgtgca aggttcacat    360
tttcacacgt tcggtcaagg gaccaagctg gagattaaac gaactgtggc agcaccaagc    420
```

```
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga acacaaaagt ctacgcctgc    660
gaagtcaccc atcagggcct gagctcgccc gtcacaaaga gcttcaacag gggagagtgt    720
tagtga                                                               726
```

<210> SEQ ID NO 116
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116

```
cccaccatgg aagcccagc gcagcttctc ttcctcctgc tactctggct ccctgatacc     60
accggagaca ttgtgatgac ccagactcca ctcagtttgt cagttacccc tgggcaacca   120
gcctctatct cttgcaagtc aagtcagagc ctcttatata gtcgcggaaa aacctatttg   180
aactgggttt tacagaagcc aggccagtct ccacagcgcc taatctatct ggtgtctaaa   240
ctggactctg gagtccctga caggttctct ggcagtggat caggaacaga ttttacactg   300
aaaatcagca gagtggaggc tgaggatgtg ggagtttatt actgcgtgca aggttcacat   360
tttcacacgt tcggtcaagg gaccaagctg gagattaaac gaactgtggc agcaccaagc   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga acacaaaagt ctacgcctgc   660
gaagtcaccc atcagggcct gagctcgccc gtcacaaaga gcttcaacag gggagagtgt   720
tagtga                                                               726
```

<210> SEQ ID NO 117
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 117

```
cccaccatgg aagcccagc gcagcttctc ttcctcctgc tactctggct ccctgatacc     60
accggagaca ttgtgatgac ccagactcca ctcagtttgt cagttacccc tgggcaacca   120
gcctctatct cttgcaagtc aagtcagagc ctcttatata gtaccggaaa aacctatttg   180
aactgggttt tacagaagcc aggccagtct ccacagcgcc taatctatct ggtgtctaaa   240
ctggactctg gagtccctga caggttctct ggcagtggat caggaacaga ttttacactg   300
aaaatcagca gagtggaggc tgaggatgtg ggagtttatt actgcgtgca aggttcacat   360
tttcacacgt tcggtcaagg gaccaagctg gagattaaac gaactgtggc agcaccaagc   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
```

```
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tagtga                                                               726
```

<210> SEQ ID NO 118
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 118

```
cccaccatgg aagccccagc gcagcttctc ttcctcctgc tactctggct ccctgatacc     60
accggagaca ttgtgatgac ccagactcca ctcagtttgt cagttacccc tgggcaacca    120
gcctctatct cttgcaagtc aagtcagagc ctcttatata gttatggaaa aacctatttg    180
aactgggttt tacagaagcc aggccagtct ccacagcgcc taatctatct ggtgtctaaa    240
ctggactctg gagtccctga caggttctct ggcagtggat caggaacaga ttttacactg    300
aaaatcagca gagtggaggc tgaggatgtg gagtttatt actgcgtgca aggttcacat    360
tttcacacgt tcggtcaagg gaccaagctg gagattaaac gaactgtggc agcaccaagc    420
gtcttcatct cccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga aacacaaagt ctacgcctgc    660
gaagtcaccc atcagggcct gagctcgccc gtcacaaaga gcttcaacag gggagagtgt    720
tagtga                                                               726
```

<210> SEQ ID NO 119
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 119

```
cccaccatgg aagccccagc gcagcttctc ttcctcctgc tactctggct ccctgatacc     60
accggagaca ttgtgatgac ccagactcca ctcagtttgt cagttacccc tgggcaacca    120
gcctctatct cttgcaagtc aagtcagagc ctcttatata gtaatgcaaa aacctatttg    180
aactgggttt tacagaagcc aggccagtct ccacagcgcc taatctatct ggtgtctaaa    240
ctggactctg gagtccctga caggttctct ggcagtggat caggaacaga ttttacactg    300
aaaatcagca gagtggaggc tgaggatgtg gagtttatt actgcgtgca aggttcacat    360
tttcacacgt tcggtcaagg gaccaagctg gagattaaac gaactgtggc agcaccaagc    420
gtcttcatct cccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
```

| ctcagcagca ccctgacgct gagcaaagca gactacgaga aacacaaagt ctacgcctgc | 660 |
| gaagtcaccc atcagggcct gagctcgccc gtcacaaaga gcttcaacag gggagagtgt | 720 |
| tagtga | 726 |

<210> SEQ ID NO 120
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120

| cccaccatgg aagccccagc gcagcttctc ttcctcctgc tactctggct ccctgatacc | 60 |
| accggagaca ttgtgatgac ccagactcca ctcagtttgt cagttacccc tgggcaacca | 120 |
| gcctctatct cttgcaagtc aagtcagagc ctcttatata gtaatgataa aacctatttg | 180 |
| aactgggttt tacagaagcc aggccagtct ccacagcgcc taatctatct ggtgtctaaa | 240 |
| ctggactctg gagtccctga caggttctct ggcagtggat caggaacaga ttttacactg | 300 |
| aaaatcagca gtggaggc tgaggatgtg ggagtttatt actgcgtgca aggttcacat | 360 |
| tttcacacgt tcggtcaagg gaccaagctg gagattaaac gaactgtggc agcaccaagc | 420 |
| gtcttcatct tcccgccatc tgatgagcag ttgaaatctg gaactgcctc tgttgtgtgc | 480 |
| ctgctgaata acttctatcc cagagaggcc aaagtacagt ggaaggtgga taacgccctc | 540 |
| caatcgggta actcccagga gagtgtcaca gagcaggaca gcaaggacag cacctacagc | 600 |
| ctcagcagca ccctgacgct gagcaaagca gactacgaga aacacaaagt ctacgcctgc | 660 |
| gaagtcaccc atcagggcct gagctcgccc gtcacaaaga gcttcaacag gggagagtgt | 720 |
| tagtga | 726 |

<210> SEQ ID NO 121
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 121

| cccaccatgg aagccccagc gcagcttctc ttcctcctgc tactctggct ccctgatacc | 60 |
| accggagaca ttgtgatgac ccagactcca ctcagtttgt cagttacccc tgggcaacca | 120 |
| gcctctatct cttgcaagtc aagtcagagc ctcttatata gtaatgaaaa aacctatttg | 180 |
| aactgggttt tacagaagcc aggccagtct ccacagcgcc taatctatct ggtgtctaaa | 240 |
| ctggactctg gagtccctga caggttctct ggcagtggat caggaacaga ttttacactg | 300 |
| aaaatcagca gtggaggc tgaggatgtg ggagtttatt actgcgtgca aggttcacat | 360 |
| tttcacacgt tcggtcaagg gaccaagctg gagattaaac gaactgtggc agcaccaagc | 420 |
| gtcttcatct tcccgccatc tgatgagcag ttgaaatctg gaactgcctc tgttgtgtgc | 480 |
| ctgctgaata acttctatcc cagagaggcc aaagtacagt ggaaggtgga taacgccctc | 540 |
| caatcgggta actcccagga gagtgtcaca gagcaggaca gcaaggacag cacctacagc | 600 |
| ctcagcagca ccctgacgct gagcaaagca gactacgaga aacacaaagt ctacgcctgc | 660 |
| gaagtcaccc atcagggcct gagctcgccc gtcacaaaga gcttcaacag gggagagtgt | 720 |

```
tagtga                                                              726

<210> SEQ ID NO 122
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 122
cccaccatgg aagccccagc gcagcttctc ttcctcctgc tactctggct ccctgatacc    60
accggagaca ttgtgatgac ccagactcca ctcagtttgt cagttacccc tgggcaacca   120
gcctctatct cttgcaagtc aagtcagagc ctcttatata gtaattttaa aacctatttg   180
aactgggttt tacagaagcc aggccagtct ccacagcgcc taatctatct ggtgtctaaa   240
ctggactctg gagtccctga caggttctct ggcagtggat caggaacaga ttttacactg   300
aaaatcagca gagtggaggc tgaggatgtg ggagtttatt actgcgtgca aggttcacat   360
tttcacacgt tcggtcaagg gaccaagctg gagattaaac gaactgtggc agcaccaagc   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga acacaaaagt ctacgcctgc   660
gaagtcaccc atcagggcct gagctcgccc gtcacaaaga gcttcaacag gggagagtgt   720
tagtga                                                              726

<210> SEQ ID NO 123
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123
cccaccatgg aagccccagc gcagcttctc ttcctcctgc tactctggct ccctgatacc    60
accggagaca ttgtgatgac ccagactcca ctcagtttgt cagttacccc tgggcaacca   120
gcctctatct cttgcaagtc aagtcagagc ctcttatata gtaatcataa aacctatttg   180
aactgggttt tacagaagcc aggccagtct ccacagcgcc taatctatct ggtgtctaaa   240
ctggactctg gagtccctga caggttctct ggcagtggat caggaacaga ttttacactg   300
aaaatcagca gagtggaggc tgaggatgtg ggagtttatt actgcgtgca aggttcacat   360
tttcacacgt tcggtcaagg gaccaagctg gagattaaac gaactgtggc agcaccaagc   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga acacaaaagt ctacgcctgc   660
gaagtcaccc atcagggcct gagctcgccc gtcacaaaga gcttcaacag gggagagtgt   720
tagtga                                                              726
```

<210> SEQ ID NO 124
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 124

```
cccaccatgg aagccccagc gcagcttctc ttcctcctgc tactctggct ccctgatacc      60
accggagaca ttgtgatgac ccagactcca ctcagtttgt cagttacccc tgggcaacca     120
gcctctatct cttgcaagtc aagtcagagc ctcttatata gtaatattaa aacctatttg     180
aactgggttt tacagaagcc aggccagtct ccacagcgcc taatctatct ggtgtctaaa     240
ctggactctg gagtccctga caggttctct ggcagtggat caggaacaga ttttacactg     300
aaaatcagca gagtggaggc tgaggatgtg ggagtttatt actgcgtgca aggttcacat     360
tttcacacgt tcggtcaagg gaccaagctg gagattaaac gaactgtggc agcaccaagc     420
gtcttcatct cccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
tagtga                                                               726
```

<210> SEQ ID NO 125
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125

```
cccaccatgg aagccccagc gcagcttctc ttcctcctgc tactctggct ccctgatacc      60
accggagaca ttgtgatgac ccagactcca ctcagtttgt cagttacccc tgggcaacca     120
gcctctatct cttgcaagtc aagtcagagc ctcttatata gtaataagaa aacctatttg     180
aactgggttt tacagaagcc aggccagtct ccacagcgcc taatctatct ggtgtctaaa     240
ctggactctg gagtccctga caggttctct ggcagtggat caggaacaga ttttacactg     300
aaaatcagca gagtggaggc tgaggatgtg ggagtttatt actgcgtgca aggttcacat     360
tttcacacgt tcggtcaagg gaccaagctg gagattaaac gaactgtggc agcaccaagc     420
gtcttcatct cccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
tagtga                                                               726
```

<210> SEQ ID NO 126
<211> LENGTH: 726

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126

| | | | | | |
|---|---|---|---|---|---|
| cccaccatgg | aagccccagc | gcagcttctc | ttcctcctgc | tactctggct | ccctgatacc | 60 |
| accggagaca | ttgtgatgac | ccagactcca | ctcagtttgt | cagttacccc | tgggcaacca | 120 |
| gcctctatct | cttgcaagtc | aagtcagagc | ctcttatata | gtaatttgaa | aacctatttg | 180 |
| aactgggttt | tacagaagcc | aggccagtct | ccacagcgcc | taatctatct | ggtgtctaaa | 240 |
| ctggactctg | gagtccctga | caggttctct | ggcagtggat | caggaacaga | ttttacactg | 300 |
| aaaatcagca | gagtggaggc | tgaggatgtg | ggagtttatt | actgcgtgca | aggttcacat | 360 |
| tttcacacgt | tcggtcaagg | gaccaagctg | gagattaaac | gaactgtggc | agcaccaagc | 420 |
| gtcttcatct | tcccgccatc | tgatgagcag | ttgaaatctg | gaactgcctc | tgttgtgtgc | 480 |
| ctgctgaata | acttctatcc | cagagaggcc | aaagtacagt | ggaaggtgga | taacgccctc | 540 |
| caatcgggta | actcccagga | gagtgtcaca | gagcaggaca | gcaaggacag | cacctacagc | 600 |
| ctcagcagca | ccctgacgct | gagcaaagca | gactacgaga | aacacaaagt | ctacgcctgc | 660 |
| gaagtcaccc | atcagggcct | gagctcgccc | gtcacaaaga | gcttcaacag | gggagagtgt | 720 |
| tagtga | | | | | | 726 |

<210> SEQ ID NO 127
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127

| | | | | | |
|---|---|---|---|---|---|
| cccaccatgg | aagccccagc | gcagcttctc | ttcctcctgc | tactctggct | ccctgatacc | 60 |
| accggagaca | ttgtgatgac | ccagactcca | ctcagtttgt | cagttacccc | tgggcaacca | 120 |
| gcctctatct | cttgcaagtc | aagtcagagc | ctcttatata | gtaatgataa | aacctatttg | 180 |
| aactgggttt | tacagaagcc | aggccagtct | ccacagcgcc | taatctatct | ggtgtctaaa | 240 |
| ctggactctg | gagtccctga | caggttctct | ggcagtggat | caggaacaga | ttttacactg | 300 |
| aaaatcagca | gagtggaggc | tgaggatgtg | ggagtttatt | actgcgtgca | aggttcacat | 360 |
| tttcacacgt | tcggtcaagg | gaccaagctg | gagattaaac | gaactgtggc | agcaccaagc | 420 |
| gtcttcatct | tcccgccatc | tgatgagcag | ttgaaatctg | gaactgcctc | tgttgtgtgc | 480 |
| ctgctgaata | acttctatcc | cagagaggcc | aaagtacagt | ggaaggtgga | taacgccctc | 540 |
| caatcgggta | actcccagga | gagtgtcaca | gagcaggaca | gcaaggacag | cacctacagc | 600 |
| ctcagcagca | ccctgacgct | gagcaaagca | gactacgaga | aacacaaagt | ctacgcctgc | 660 |
| gaagtcaccc | atcagggcct | gagctcgccc | gtcacaaaga | gcttcaacag | gggagagtgt | 720 |
| tagtga | | | | | | 726 |

<210> SEQ ID NO 128
<211> LENGTH: 726
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 128

| | | | | |
|---|---|---|---|---|
| cccaccatgg | aagccccagc | gcagcttctc | ttcctcctgc | tactctggct | ccctgatacc | 60 |
| accggagaca | ttgtgatgac | ccagactcca | ctcagtttgt | cagttacccc | tgggcaacca | 120 |
| gcctctatct | cttgcaagtc | aagtcagagc | ctcttatata | gtaataataa | aacctatttg | 180 |
| aactgggttt | tacagaagcc | aggccagtct | ccacagcgcc | taatctatct | ggtgtctaaa | 240 |
| ctggactctg | gagtccctga | caggttctct | ggcagtggat | caggaacaga | ttttacactg | 300 |
| aaaatcagca | gagtggaggc | tgaggatgtg | ggagtttatt | actgcgtgca | aggttcacat | 360 |
| tttcacacgt | tcggtcaagg | gaccaagctg | gagattaaac | gaactgtggc | agcaccaagc | 420 |
| gtcttcatct | tcccgccatc | tgatgagcag | ttgaaatctg | gaactgcctc | tgttgtgtgc | 480 |
| ctgctgaata | acttctatcc | cagagaggcc | aaagtacagt | ggaaggtgga | taacgccctc | 540 |
| caatcgggta | actcccagga | gagtgtcaca | gagcaggaca | gcaaggacag | cacctacagc | 600 |
| ctcagcagca | ccctgacgct | gagcaaagca | gactacgaga | aacacaaagt | ctacgcctgc | 660 |
| gaagtcaccc | atcagggcct | gagctcgccc | gtcacaaaga | gcttcaacag | gggagagtgt | 720 |
| tagtga | | | | | | 726 |

<210> SEQ ID NO 129
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 129

| | | | | |
|---|---|---|---|---|
| cccaccatgg | aagccccagc | gcagcttctc | ttcctcctgc | tactctggct | ccctgatacc | 60 |
| accggagaca | ttgtgatgac | ccagactcca | ctcagtttgt | cagttacccc | tgggcaacca | 120 |
| gcctctatct | cttgcaagtc | aagtcagagc | ctcttatata | gtaatcagaa | aacctatttg | 180 |
| aactgggttt | tacagaagcc | aggccagtct | ccacagcgcc | taatctatct | ggtgtctaaa | 240 |
| ctggactctg | gagtccctga | caggttctct | ggcagtggat | caggaacaga | ttttacactg | 300 |
| aaaatcagca | gagtggaggc | tgaggatgtg | ggagtttatt | actgcgtgca | aggttcacat | 360 |
| tttcacacgt | tcggtcaagg | gaccaagctg | gagattaaac | gaactgtggc | agcaccaagc | 420 |
| gtcttcatct | tcccgccatc | tgatgagcag | ttgaaatctg | gaactgcctc | tgttgtgtgc | 480 |
| ctgctgaata | acttctatcc | cagagaggcc | aaagtacagt | ggaaggtgga | taacgccctc | 540 |
| caatcgggta | actcccagga | gagtgtcaca | gagcaggaca | gcaaggacag | cacctacagc | 600 |
| ctcagcagca | ccctgacgct | gagcaaagca | gactacgaga | aacacaaagt | ctacgcctgc | 660 |
| gaagtcaccc | atcagggcct | gagctcgccc | gtcacaaaga | gcttcaacag | gggagagtgt | 720 |
| tagtga | | | | | | 726 |

<210> SEQ ID NO 130
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130

```
cccaccatgg aagccccagc gcagcttctc ttcctcctgc tactctggct ccctgatacc      60
accggagaca ttgtgatgac ccagactcca ctcagtttgt cagttacccc tgggcaacca     120
gcctctatct cttgcaagtc aagtcagagc ctcttatata gtaatcgtaa aacctatttg     180
aactgggttt tacagaagcc aggccagtct ccacagcgcc taatctatct ggtgtctaaa     240
ctggactctg gagtccctga caggttctct ggcagtggat caggaacaga ttttacactg     300
aaaatcagca gagtggaggc tgaggatgtg ggagtttatt actgcgtgca aggttcacat     360
tttcacacgt tcggtcaagg gaccaagctg gagattaaac gaactgtggc agcaccaagc     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga acacaaagt ctacgcctgc      660
gaagtcaccc atcagggcct gagctcgccc gtcacaaaga gcttcaacag gggagagtgt     720
tagtga                                                                726
```

<210> SEQ ID NO 131
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 131

```
cccaccatgg aagccccagc gcagcttctc ttcctcctgc tactctggct ccctgatacc      60
accggagaca ttgtgatgac ccagactcca ctcagtttgt cagttacccc tgggcaacca     120
gcctctatct cttgcaagtc aagtcagagc ctcttatata gtaatagtaa aacctatttg     180
aactgggttt tacagaagcc aggccagtct ccacagcgcc taatctatct ggtgtctaaa     240
ctggactctg gagtccctga caggttctct ggcagtggat caggaacaga ttttacactg     300
aaaatcagca gagtggaggc tgaggatgtg ggagtttatt actgcgtgca aggttcacat     360
tttcacacgt tcggtcaagg gaccaagctg gagattaaac gaactgtggc agcaccaagc     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga acacaaagt ctacgcctgc      660
gaagtcaccc atcagggcct gagctcgccc gtcacaaaga gcttcaacag gggagagtgt     720
tagtga                                                                726
```

<210> SEQ ID NO 132
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 132

| | |
|---|---|
| cccaccatgg aagccccagc gcagcttctc ttcctcctgc tactctggct ccctgatacc | 60 |
| accggagaca ttgtgatgac ccagactcca ctcagtttgt cagttacccc tgggcaacca | 120 |
| gcctctatct cttgcaagtc aagtcagagc ctcttatata gtaataccaa aacctatttg | 180 |
| aactgggttt tacagaagcc aggccagtct ccacagcgcc taatctatct ggtgtctaaa | 240 |
| ctggactctg gagtccctga caggttctct ggcagtggat caggaacaga ttttacactg | 300 |
| aaaatcagca gagtggaggc tgaggatgtg ggagtttatt actgcgtgca aggttcacat | 360 |
| tttcacacgt tcggtcaagg gaccaagctg gagattaaac gaactgtggc agcaccaagc | 420 |
| gtcttcatct cccgccatc tgatgagcag ttgaaatctg gaactgcctc tgttgtgtgc | 480 |
| ctgctgaata acttctatcc cagagaggcc aaagtacagt ggaaggtgga taacgccctc | 540 |
| caatcgggta actcccagga gagtgtcaca gagcaggaca gcaaggacag cacctacagc | 600 |
| ctcagcagca ccctgacgct gagcaaagca gactacgaga aacacaaagt ctacgcctgc | 660 |
| gaagtcaccc atcagggcct gagctcgccc gtcacaaaga gcttcaacag gggagagtgt | 720 |
| tagtga | 726 |

<210> SEQ ID NO 133
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133

| | |
|---|---|
| cccaccatgg aagccccagc gcagcttctc ttcctcctgc tactctggct ccctgatacc | 60 |
| accggagaca ttgtgatgac ccagactcca ctcagtttgt cagttacccc tgggcaacca | 120 |
| gcctctatct cttgcaagtc aagtcagagc ctcttatata gtaatttgaa aacctatttg | 180 |
| aactgggttt tacagaagcc aggccagtct ccacagcgcc taatctatct ggtgtctaaa | 240 |
| ctggactctg gagtccctga caggttctct ggcagtggat caggaacaga ttttacactg | 300 |
| aaaatcagca gagtggaggc tgaggatgtg ggagtttatt actgcgtgca aggttcacat | 360 |
| tttcacacgt tcggtcaagg gaccaagctg gagattaaac gaactgtggc agcaccaagc | 420 |
| gtcttcatct cccgccatc tgatgagcag ttgaaatctg gaactgcctc tgttgtgtgc | 480 |
| ctgctgaata acttctatcc cagagaggcc aaagtacagt ggaaggtgga taacgccctc | 540 |
| caatcgggta actcccagga gagtgtcaca gagcaggaca gcaaggacag cacctacagc | 600 |
| ctcagcagca ccctgacgct gagcaaagca gactacgaga aacacaaagt ctacgcctgc | 660 |
| gaagtcaccc atcagggcct gagctcgccc gtcacaaaga gcttcaacag gggagagtgt | 720 |
| tagtga | 726 |

<210> SEQ ID NO 134
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 134

| | |
|---|---|
| cccaccatgg aagccccagc gcagcttctc ttcctcctgc tactctggct ccctgatacc | 60 |
| accggagaca ttgtgatgac ccagactcca ctcagtttgt cagttacccc tgggcaacca | 120 |

```
gcctctatct cttgcaagtc aagtcagagc ctcttatata gtaatgttaa aacctatttg    180
aactgggttt tacagaagcc aggccagtct ccacagcgcc taatctatct ggtgtctaaa    240
ctggactctg gagtccctga caggttctct ggcagtggat caggaacaga ttttacactg    300
aaaatcagca gagtggaggc tgaggatgtg ggagtttatt actgcgtgca aggttcacat    360
tttcacacgt tcggtcaagg gaccaagctg gagattaaac gaactgtggc agcaccaagc    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga acacaaaagt ctacgcctgc    660
gaagtcaccc atcagggcct gagctcgccc gtcacaaaga gcttcaacag gggagagtgt    720
tagtga    726
```

`<210>` SEQ ID NO 135
`<211>` LENGTH: 726
`<212>` TYPE: DNA
`<213>` ORGANISM: Artificial Sequence
`<220>` FEATURE:
`<221>` NAME/KEY: source
`<223>` OTHER INFORMATION: /note="Description of Artificial Sequence: Synthetic polynucleotide"

`<400>` SEQUENCE: 135

```
cccaccatgg aagccccagc gcagcttctc ttcctcctgc tactctggct ccctgatacc     60
accggagaca ttgtgatgac ccagactcca ctcagtttgt cagttacccc tgggcaacca    120
gcctctatct cttgcaagtc aagtcagagc ctcttatata gtaaaggaaa tacctatttg    180
aactgggttt tacagaagcc aggccagtct ccacagcgcc taatctatct ggtgtctaaa    240
ctggactctg gagtccctga caggttctct ggcagtggat caggaacaga ttttacactg    300
aaaatcagca gagtggaggc tgaggatgtg ggagtttatt actgcgtgca aggttcacat    360
tttcacacgt tcggtcaagg gaccaagctg gagattaaac gaactgtggc agcaccaagc    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgaga acacaaaagt ctacgcctgc    660
gaagtcaccc atcagggcct gagctcgccc gtcacaaaga gcttcaacag gggagagtgt    720
tagtga    726
```

`<210>` SEQ ID NO 136
`<211>` LENGTH: 16
`<212>` TYPE: PRT
`<213>` ORGANISM: Artificial Sequence
`<220>` FEATURE:
`<221>` NAME/KEY: source
`<223>` OTHER INFORMATION: /note="Description of Artificial Sequence: Synthetic peptide"
`<220>` FEATURE:
`<221>` NAME/KEY: VARIANT
`<222>` LOCATION: (11)..(11)
`<223>` OTHER INFORMATION: /replace="Arg" or "Gln" or "His" or "Ser" or "Tyr" or "Ala" or "Asp" or "Glu" or "Phe" or "Ile" or "Leu" or "Met" or "Asn" or "Thr" or "Val"
`<220>` FEATURE:
`<221>` NAME/KEY: misc_feature
`<222>` LOCATION: (1)..(16)

```
<223> OTHER INFORMATION: /note="Variant residue given in the sequence
      has no preference with respect to those in the annotation
      for the variant position"

<400> SEQUENCE: 136

Lys Ser Ser Gln Ser Leu Leu Tyr Ser Asn Lys Lys Thr Tyr Leu Asn
1               5                   10                  15
```